US011639369B2

(12) United States Patent
Brik et al.

(10) Patent No.: US 11,639,369 B2
(45) Date of Patent: May 2, 2023

(54) UBIQUITIN HIGH AFFINITY CYCLIC PEPTIDES AND METHODS OF USE THEREOF

(71) Applicants: TECHNION RESEARCH & DEVELOPMENT FOUNDATION LIMITED, Haifa (IL); THE UNIVERSITY OF TOKYO, Tokyo (JP)

(72) Inventors: Ashraf Brik, Haifa (IL); Mickal Nawatha, Reine (IL); Hiroaki Suga, Tokyo (JP); Joseph Rogers, Tokyo (JP)

(73) Assignees: TECHNION RESEARCH & DEVELOPMENT FOUNDATION LIMITED, Haifa (IL); THE UNIVERSITY OF TOKYO, Tokyo (JP)

( * ) Notice: Subject to any disclaimer, the term of this patent is extended or adjusted under 35 U.S.C. 154(b) by 59 days.

(21) Appl. No.: 16/972,764

(22) PCT Filed: Jun. 6, 2019

(86) PCT No.: PCT/IL2019/050654
§ 371 (c)(1),
(2) Date: Dec. 7, 2020

(87) PCT Pub. No.: WO2019/234751
PCT Pub. Date: Dec. 12, 2019

(65) Prior Publication Data
US 2021/0238231 A1    Aug. 5, 2021

Related U.S. Application Data

(60) Provisional application No. 62/793,470, filed on Jan. 17, 2019, provisional application No. 62/681,389, filed on Jun. 6, 2018.

(51) Int. Cl.
| | |
|---|---|
| *C07K 7/64* | (2006.01) |
| *A61P 35/00* | (2006.01) |
| *C07K 19/00* | (2006.01) |
| *A61K 38/00* | (2006.01) |

(52) U.S. Cl.
CPC .............. *C07K 7/64* (2013.01); *A61P 35/00* (2018.01); *C07K 19/00* (2013.01); *A61K 38/00* (2013.01)

(58) Field of Classification Search
CPC ........... C07K 7/64; C07K 19/00; A61P 35/00; A61K 38/00
See application file for complete search history.

(56) References Cited

FOREIGN PATENT DOCUMENTS

WO    2012040527 A2    3/2012

OTHER PUBLICATIONS

Rogers et al. "In vivo modulation of ubiquitin chains by N-methylated non-proteinogenic cyclic peptides" RSC Chemical Biology 2: 513-522. (Year: 2021).*
Nawatha et al. "De novo macrocyclic peptides that specifically modulate Lys48-linked ubiquitin chains" Nature Chemistry 11:644-652. (Year: 2019).*
Ito et al. "Technologies for the Synthesis of mRNA-Encoding Libraries and Discovery of Bioactive Natural Product-Inspired Non-Traditional Macrocyclic Peptides" Molecules 18:3502-3528 (Year: 2013).*
D'Arcy, P., Brnjic, S., Olofsson, M. et al. Inhibition of proteasome deubiquitinating activity as a new cancer therapy. Nat Med 17, 1636-1640 (2011). https://doi.org/10.1038/nm.2536.
Pushparathinam, Gopinath & Ohayon, Shimrit & Nawatha, Mickal & Brik, Ashraf. (2016). Chemical and semisynthetic approaches to study and target deubiquitinases Chemical Society reviews. 45. DOI: 10.1039/c6cs00083e.
Zorzi, A., Deyle, K. & Heinis, C. Cyclic peptide therapeutics: past, present and future. Curr. Opin. Chem. Biol. 38, 24-29 (2017). DOI: 10.1016/j.cbpa.2017.02.006.
Zhang, Y., Zhou, L., Rouge, L. et al. (2012). Conformational stabilization of ubiquitin yields potent and selective inhibitors of USP7. Nature Chemical Biology, 9(1), 51-58 DOI: 10.1038/nchembio. 1134.
Nawatha, M., Rogers, J.M., Bonn, S.M et al. De novo macrocyclic peptides that specifically modulate Lys48-linked ubiquitin chains. Nat. Chem. 11, 644-652 (2019). https://doi.org/10.1038/s41557-019-0278-x.
White CJ, Yudin AK. Contemporary strategies for peptide macrocyclization. Nat Chem. Jun. 23, 2011;3(7):509-24. https://doi.org/10.1038/nchem.1062.
Pickart, C. M., & Raasi, S. (2005). Controlled synthesis of polyubiquitin chains. Methods in enzymology, 399, 21-36. https://doi.org/10.1016/S0076-6879(05)99002-2.
Varadan R, Walker O, Pickart C, Fushman D. Structural properties of polyubiquitin chains in solution. J Mol Biol. Dec. 6, 2002;324(4):637-47. DOI: 10.1016/s0022-2836(02)01198-1.
Varadan R, Assfalg M, Haririnia A, Raasi S, Pickart C, Fushman D. Solution conformation of Lys63-linked di-ubiquitin chain provides clues to functional diversity of polyubiquitin signaling. J Biol Chem. Feb. 20, 2004;279(8):7055-63. Epub Nov. 25, 2003. DOI: 10.1074/jbc.M309184200.
Ranjani Varadan, Assfalg M, Fushman D. Using NMR spectroscopy to monitor ubiquitin chain conformation and interactions with ubiquitin-binding domains. Methods Enzymol. 2005;399:177-92. DOI: 10.1016/50076-6879(05) 99012-5.

(Continued)

*Primary Examiner* — Sudhakar Katakam
*Assistant Examiner* — Zachary J Miknis
(74) *Attorney, Agent, or Firm* — The Roy Gross Law Firm, LLC; Roy Gross

(57) ABSTRACT

The present invention is directed to a cyclic polypeptide having ubiquitin binding affinity ($K_D$) of 0.1-100 nM. Further provided are methods for reducing deubiquitination activity of a cell, and for treating cancer in a subject in need thereof.

9 Claims, 43 Drawing Sheets
Specification includes a Sequence Listing.

(56) References Cited

OTHER PUBLICATIONS

Verma R, Peters NR, D'Onofrio M, Tochtrop GP, Sakamoto KM, Varadan R, Zhang M, Coffino P, Fushman D, Deshaies RJ, King RW. Ubistatins inhibit proteasome-dependent degradation by binding the ubiquitin chain. Science. Oct. 1, 2004;306(5693):117-20. doi: 10.1126/science.1100946. Erratum in: Science. May 16, 2008;320(5878):874. PMID:15459393.
Roth G, Freund S, Möhrle B, Wöllner K, Brünjes J, Gauglitz G, Wiesmüller KH, Jung G. Ubiquitin binds to a short peptide segment of hydrolase UCH-L3: a study by FCS, RIfS, ITC and NMR. Chembiochem. Feb. 12, 2007;8(3):323-31. doi: 10.1002/cbic. 200600254. PMID: 17211910.
Bondalapati S, Jbara M, Brik A. Expanding the chemical toolbox for the synthesis of large and uniquely modified proteins. Nat Chem. Apr. 22, 2016;8(5):407-18. doi: 10.1038/nchem.2476. PMID: 27102674.
PCT International Search Report for International Application No. PCT/IL2019/050654, dated Sep. 26, 2019, 5pp.
PCT Written Opinion for International Application No. PCT/IL2019/050654, dated Sep. 26, 2019, 6pp.
PCT International Preliminary Report on Patentability for International Application No. PCT/IL2019/050654, dated Dec. 8, 2020, 7pp.

\* cited by examiner

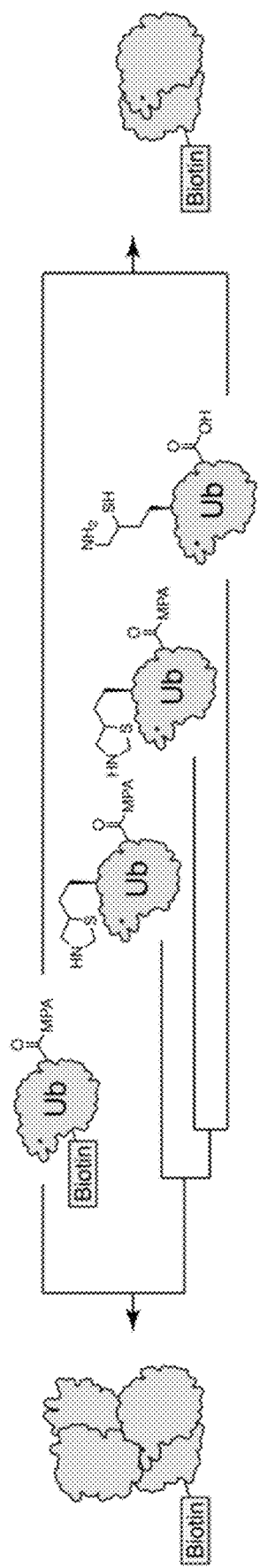
FIGURE 1A
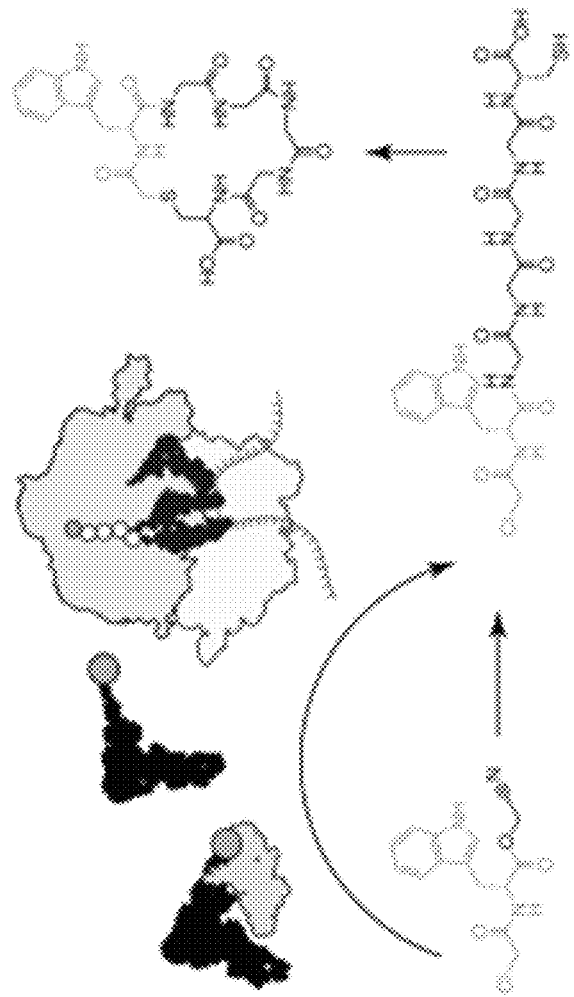
FIGURE 1B
FIGURE 1C

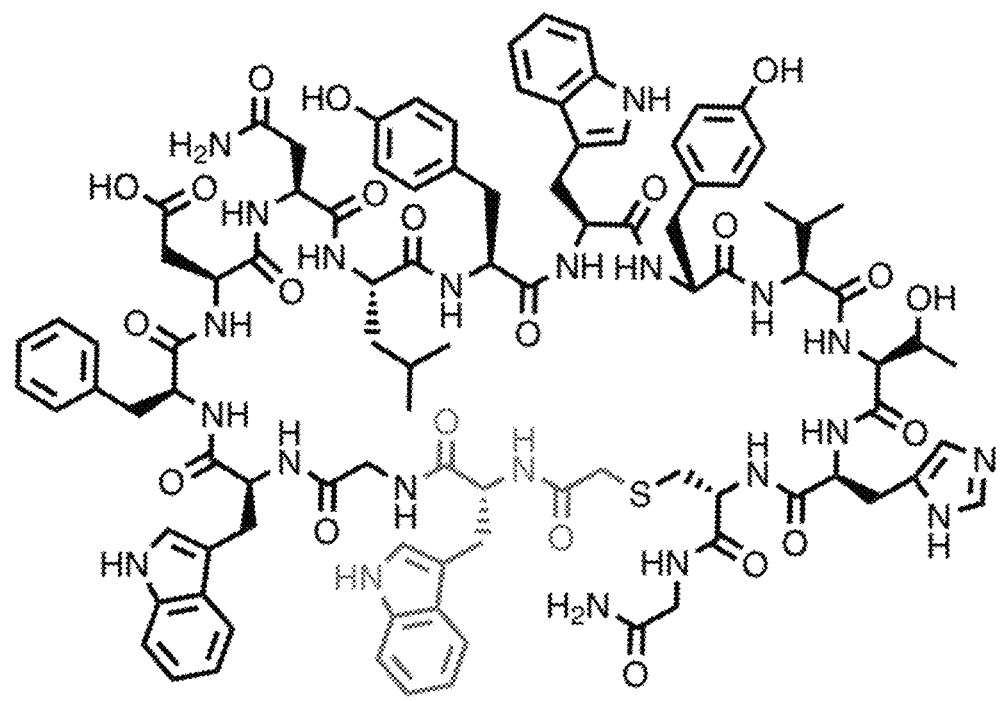
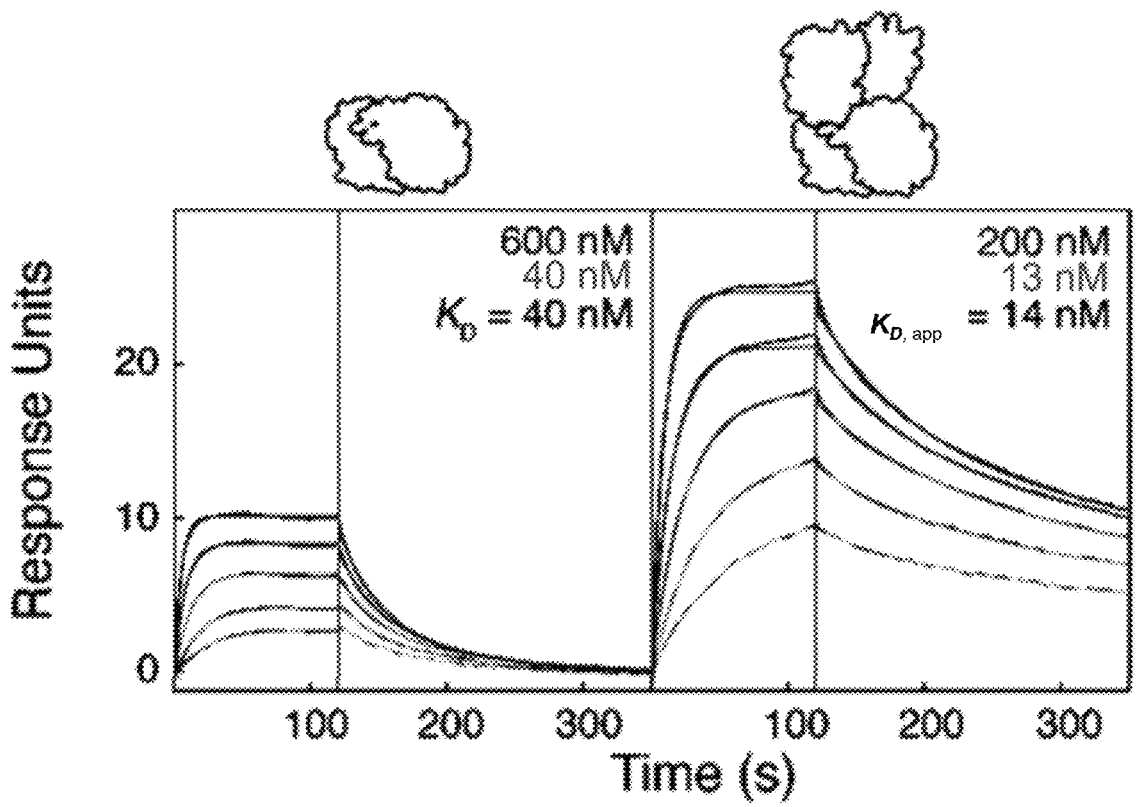
FIGURE 1E

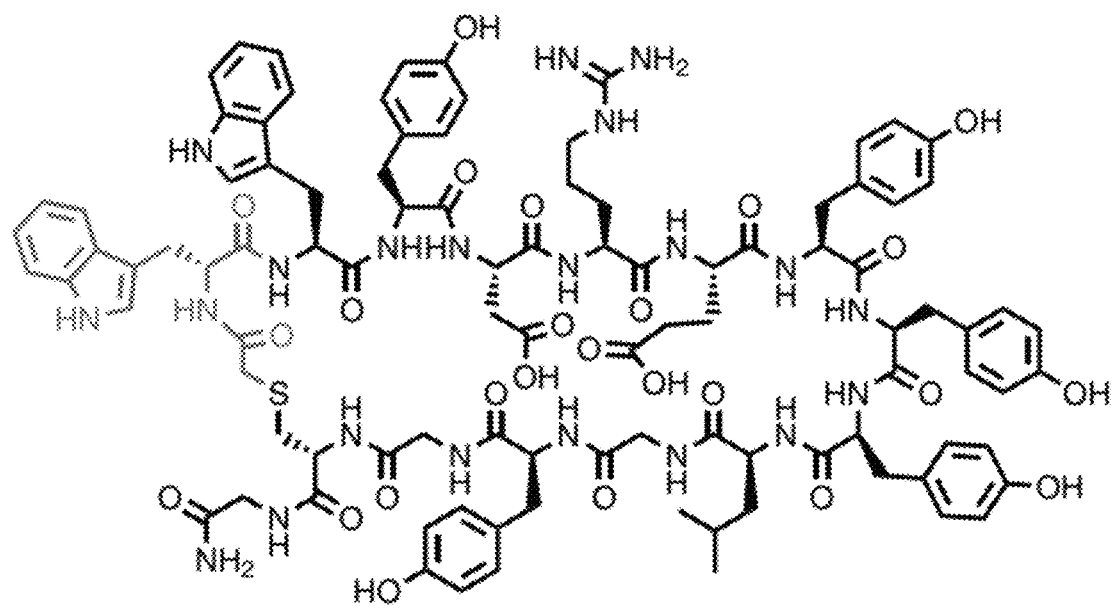
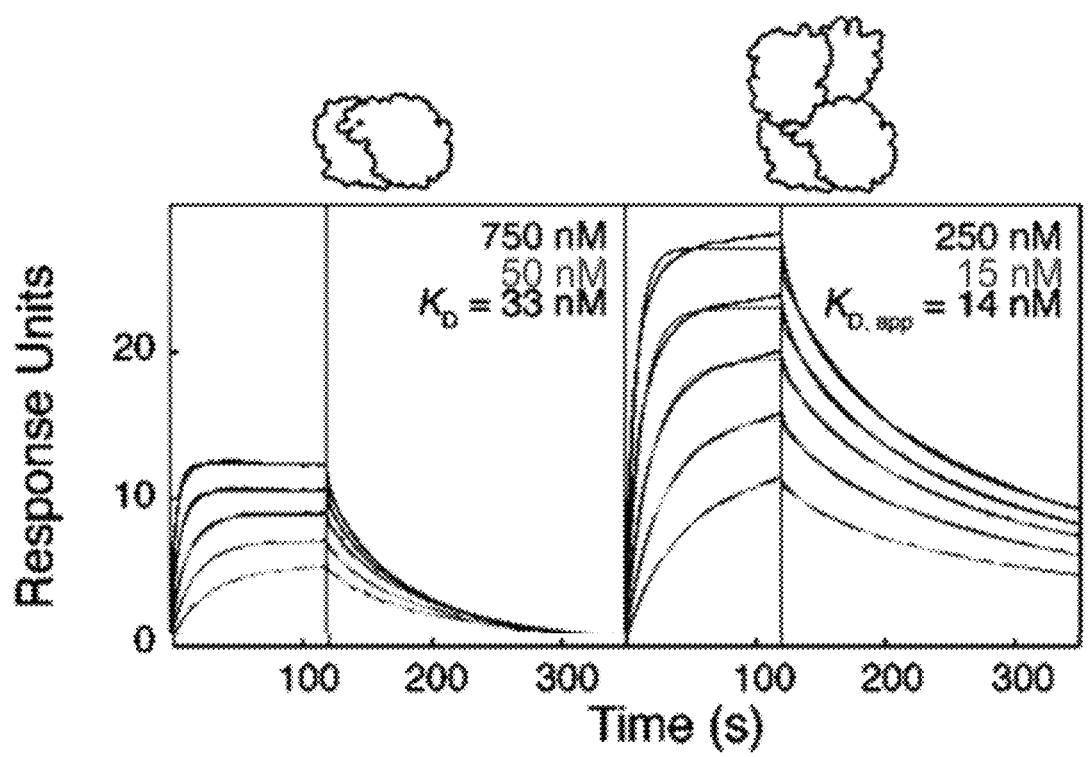
FIGURE 1F

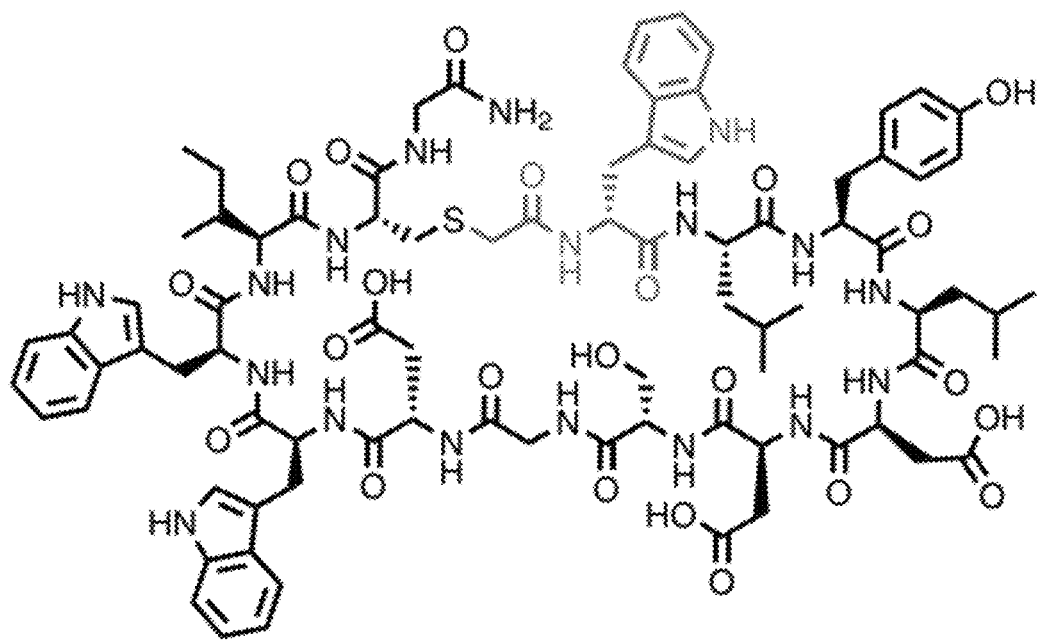
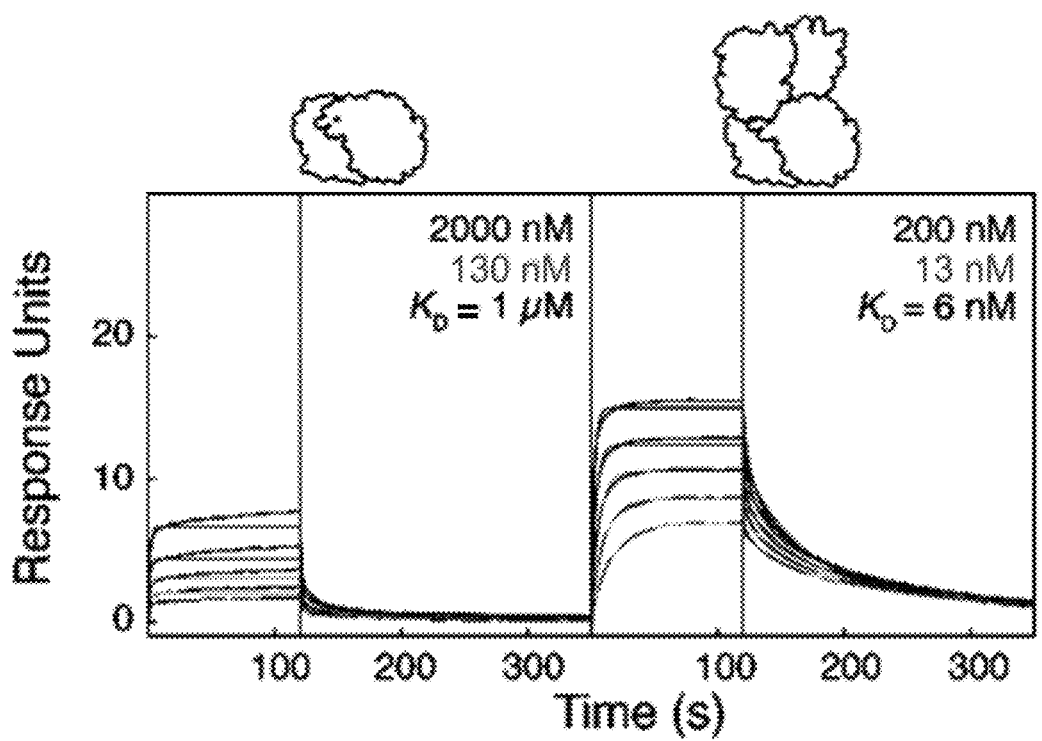
FIGURE 1H

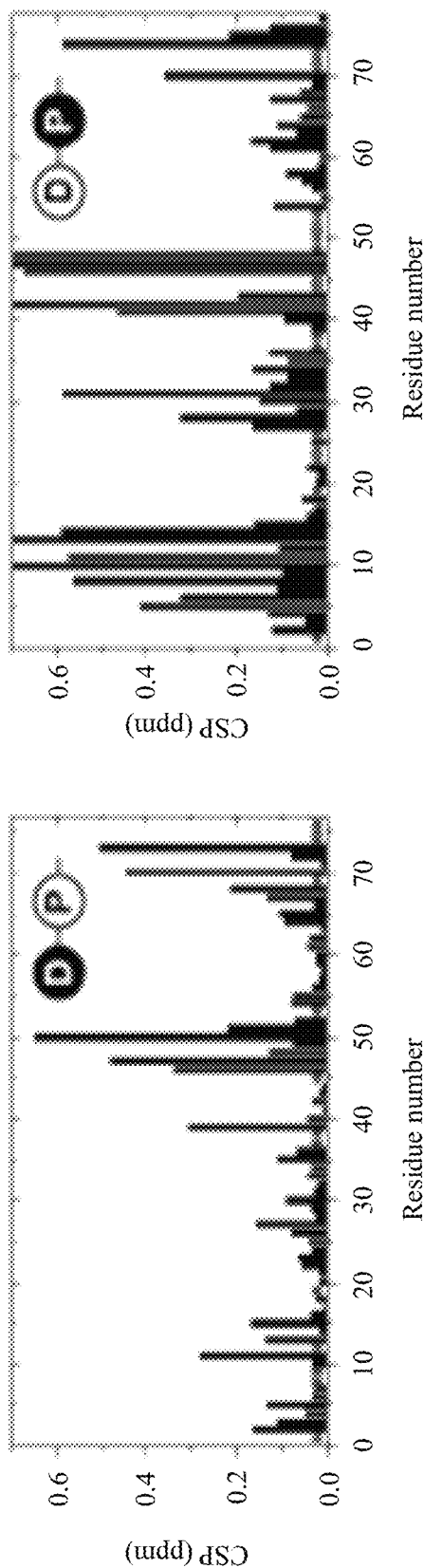
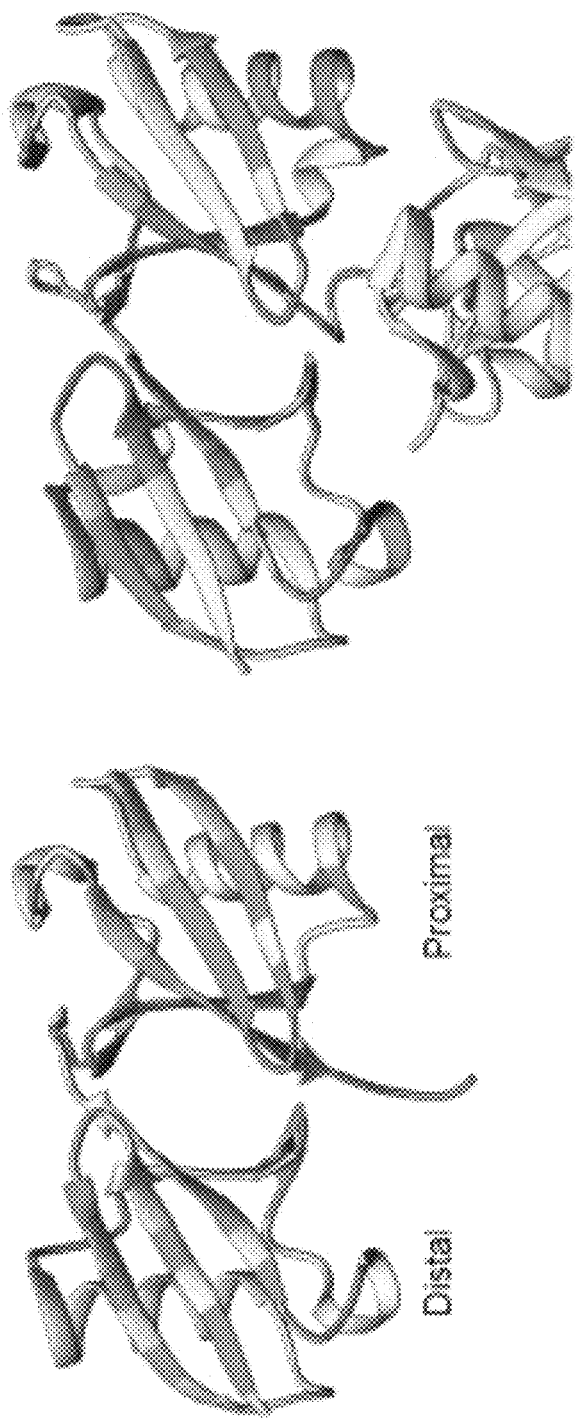
FIGURE 2B
FIGURE 2C
FIGURE 2E

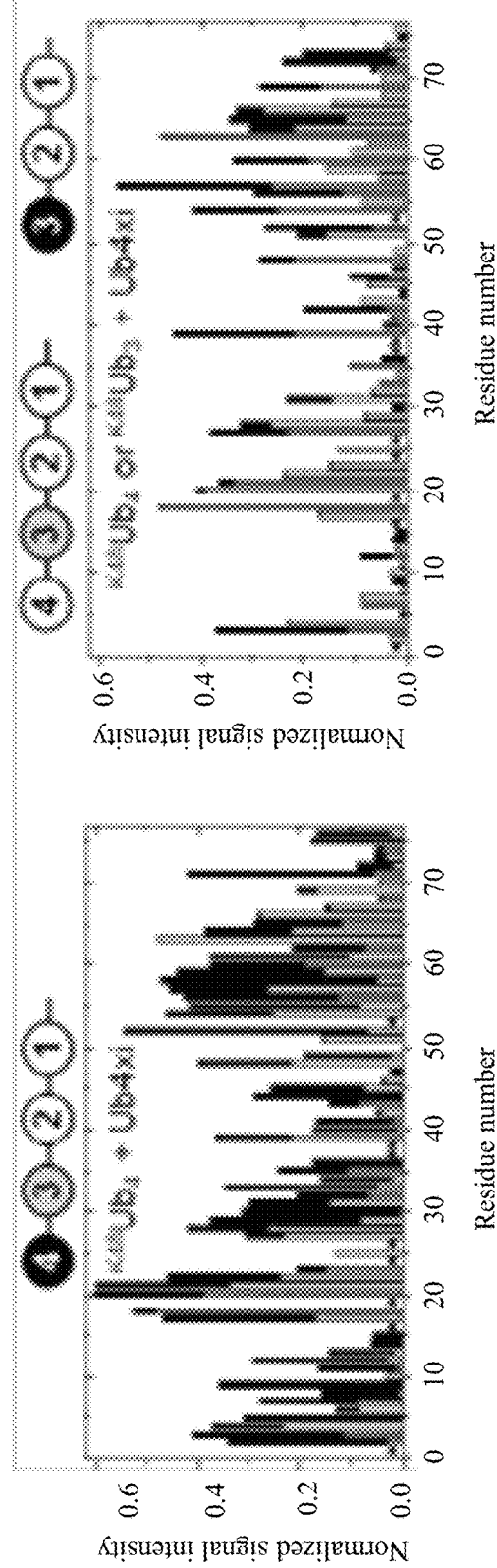
FIGURE 2D
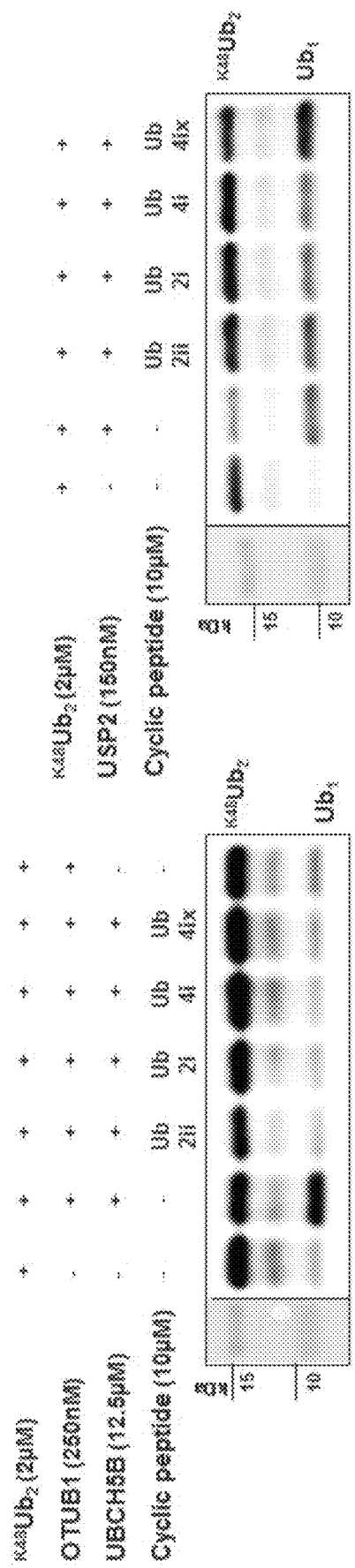
FIGURE 3A
FIGURE 3C

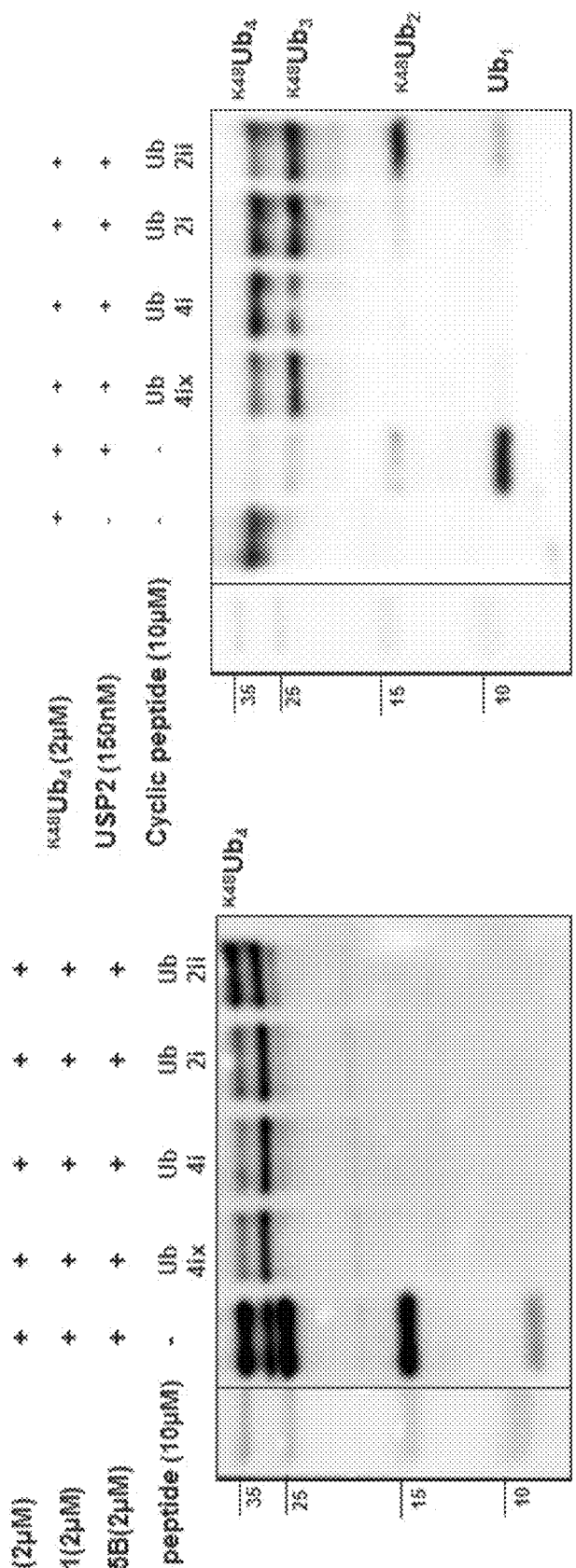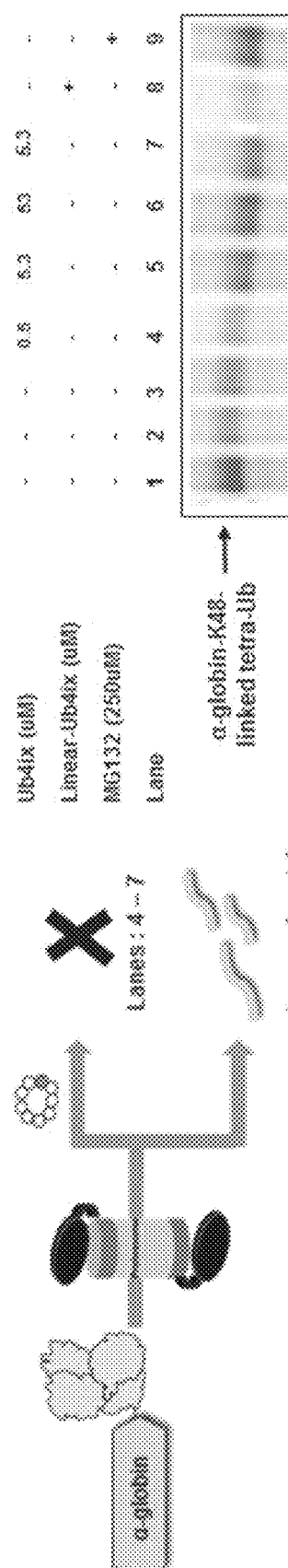
FIGURE 3B
FIGURE 3D
FIGURE 4A
FIGURE 4B

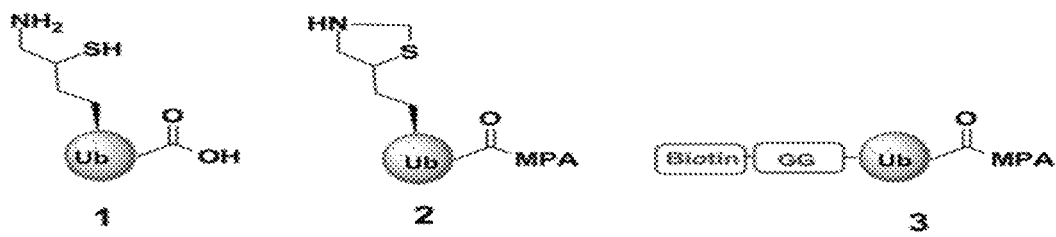
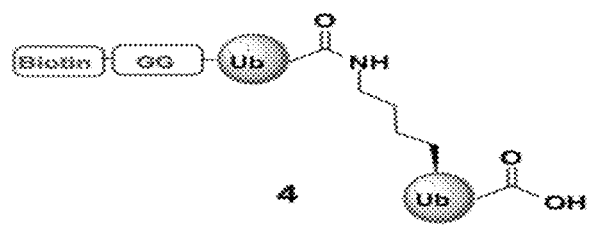
MPA=3-mercaptopropionic acid
MPAA=4-mercaptophenylacetic acid
FIGURE 7

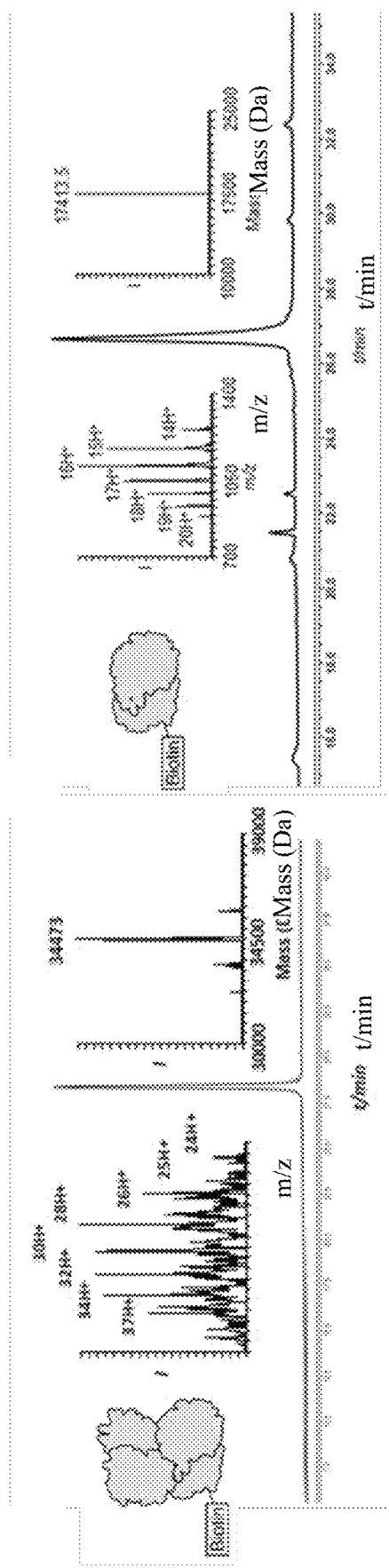
FIGURE 8A
FIGURE 8B
FIGURE 8D
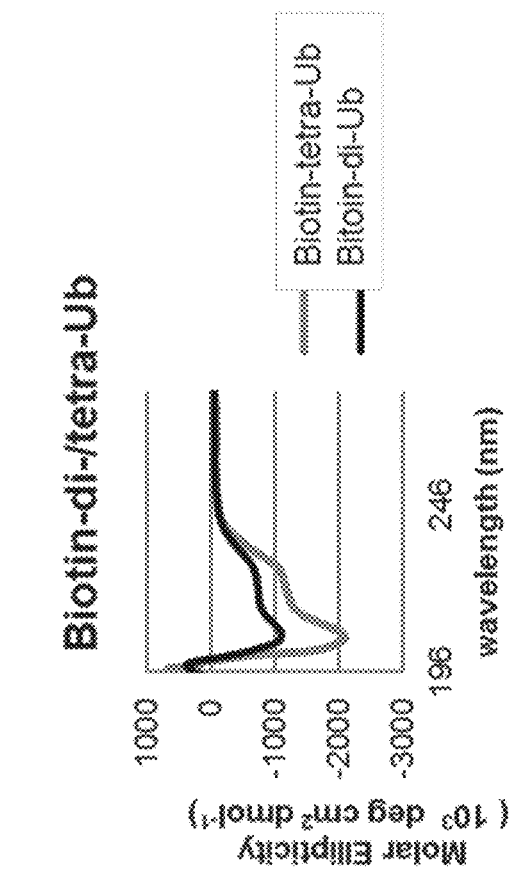
FIGURE 8C

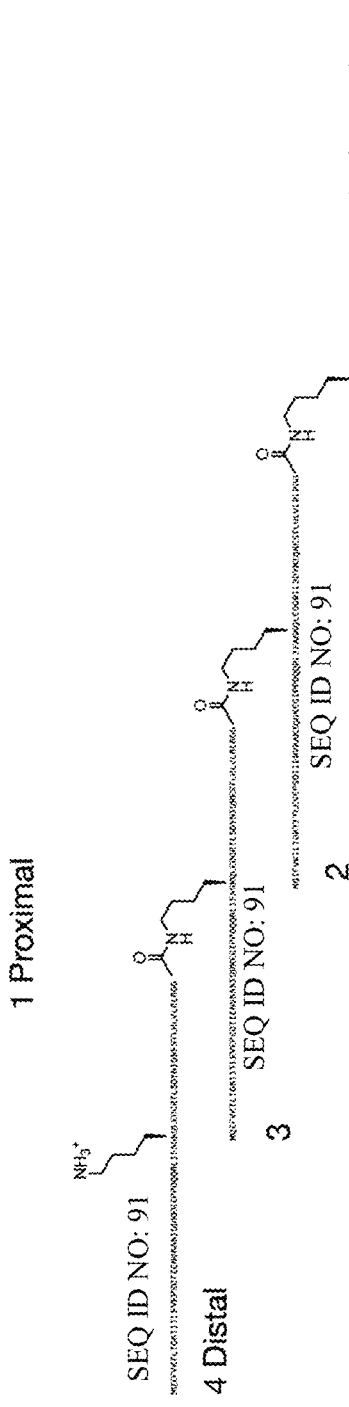
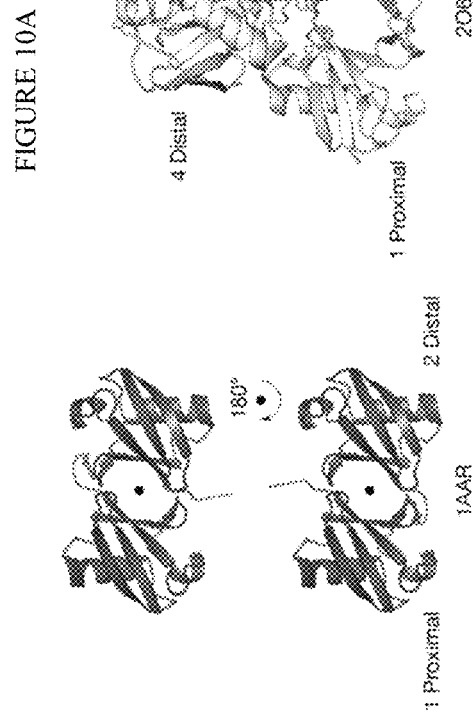
FIGURE 10A
FIGURE 10B

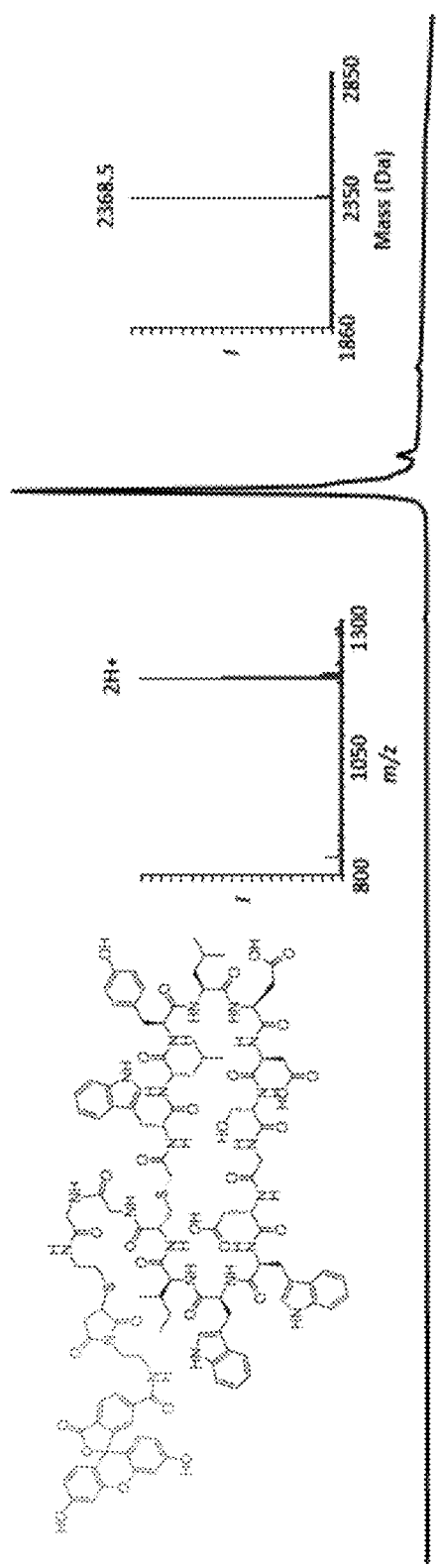
FIGURE 13
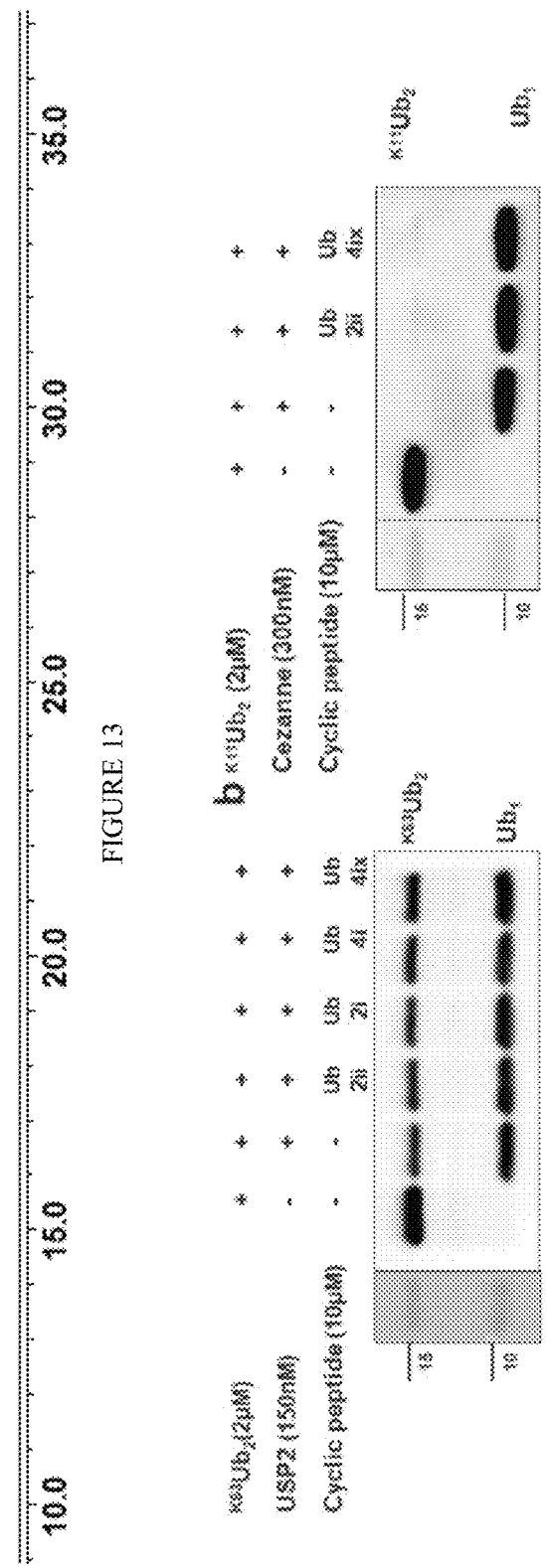
FIGURE 14A
FIGURE 14B

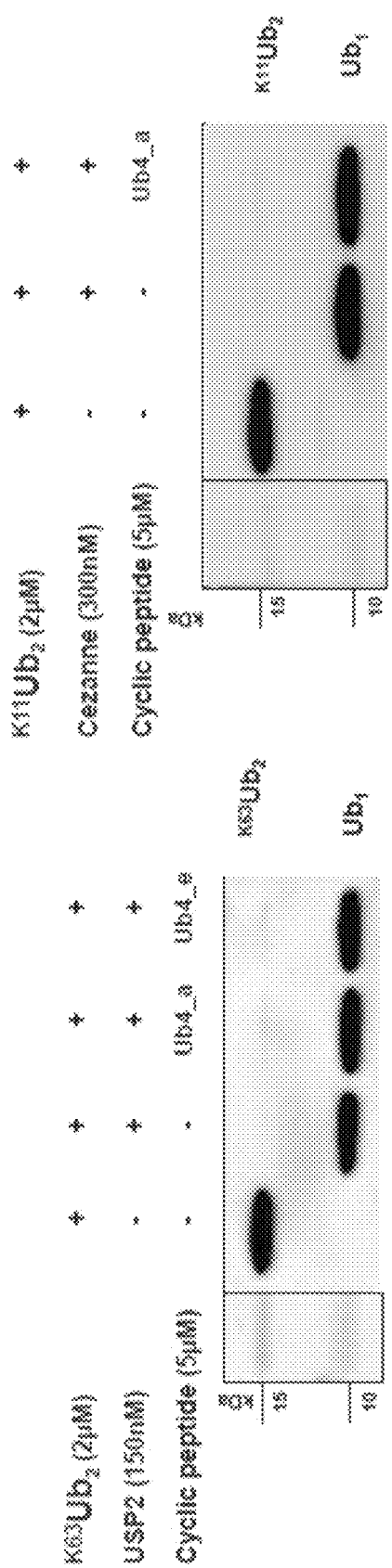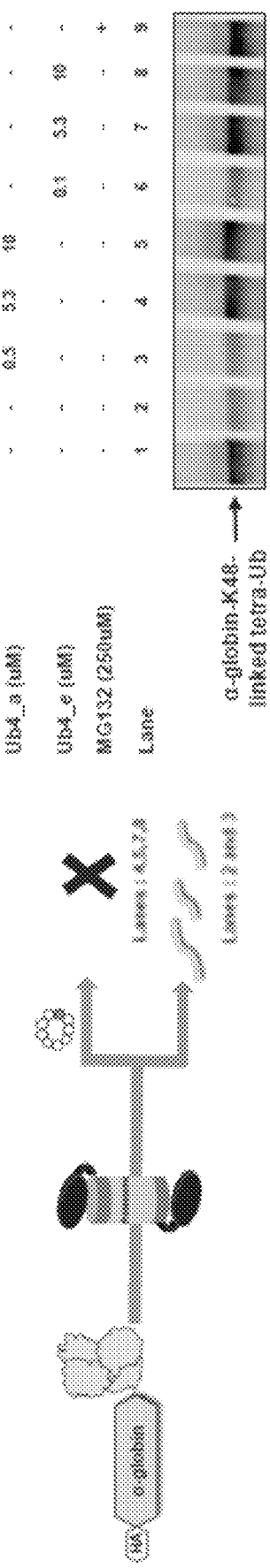
FIGURE 31A
FIGURE 31B
FIGURE 32A
FIGURE 32B

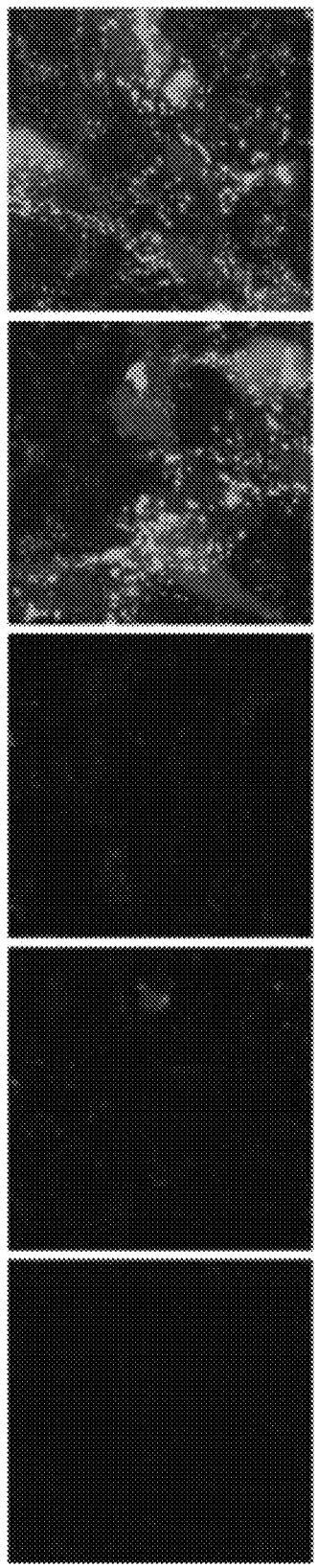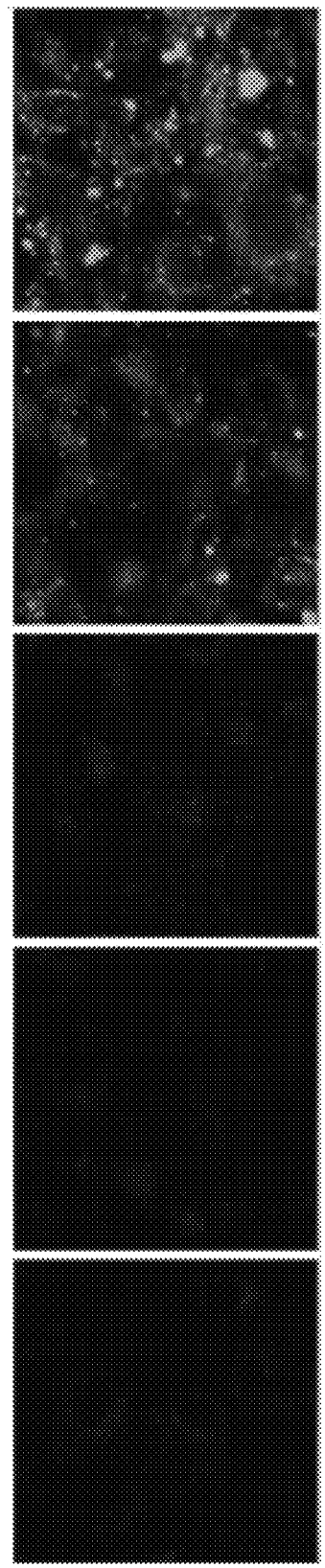

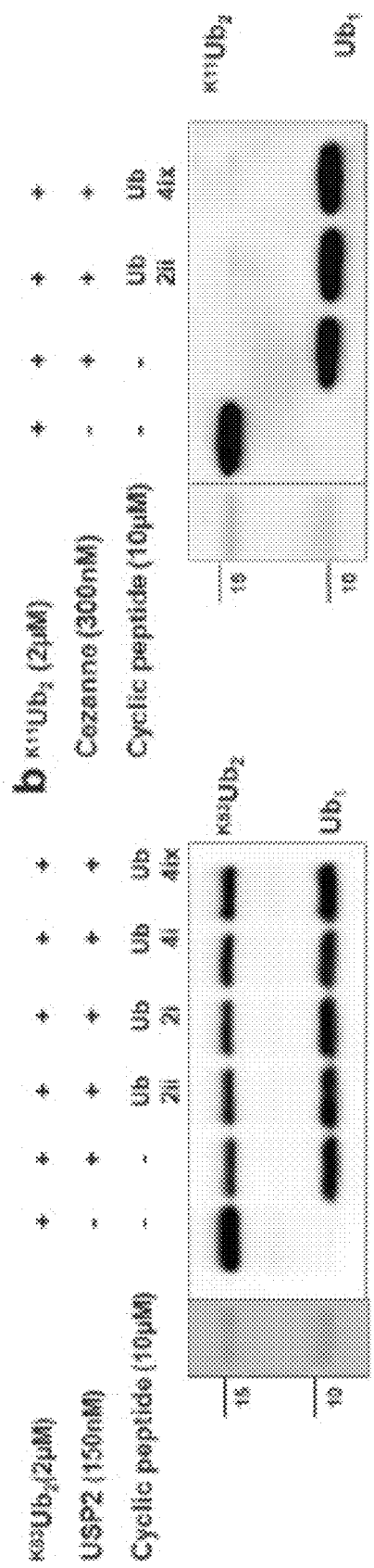
FIGURE 39A
FIGURE 39B
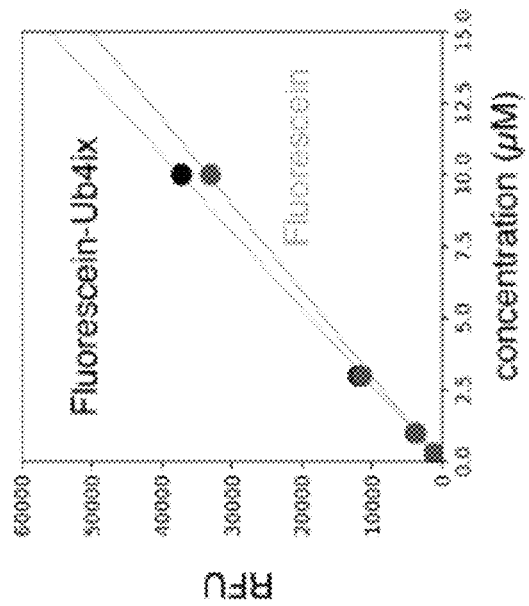
FIGURE 40

SEQUENCE LISTING

```
<160> NUMBER OF SEQ ID NOS: 90

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is any naturally occurring or non natrually
      occurring amino acid

<400> SEQUENCE: 1

Trp Tyr Asp Xaa Glu Tyr Tyr Tyr Leu Gly Tyr Gly Cys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(12)
<223> OTHER INFORMATION: X is any naturally occurring or non natrually
      occurring amino acid

<400> SEQUENCE: 2

Gly Trp Phe Asp Asn Leu Tyr Trp Tyr Val Xaa Xaa Cys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is Leu, Gln, Thr, Asn, Glu, or Asp
<220> FEATURE:
<221> NAME/KEY: MISC_FEATURE
<222> LOCATION: (8)..(8)
<223> OTHER INFORMATION: X is Leu or Tyr
<220> FEATURE:
<221> NAME/KEY: MISC_FEATURE
<222> LOCATION: (9)..(9)
```

```
<223> OTHER INFORMATION: X is Phe or Tyr
<220> FEATURE:
<221> NAME/KEY: MISC_FEATURE
<222> LOCATION: (10)..(10)
<223> OTHER INFORMATION: X is Val or Leu

<400> SEQUENCE: 3

Gly Trp Phe Asp Asp Xaa Tyr Xaa Xaa Xaa Ala Tyr Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is any naturally occurring or non natrually
      occurring amino acid

<400> SEQUENCE: 4

Leu Tyr Leu Asp Asp Xaa Gly Asp Trp Trp Ile Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is Tyr Leu
<220> FEATURE:
<221> NAME/KEY: MOD_RES
<222> LOCATION: (5)..(5)
<223> OTHER INFORMATION: Orn
<220> FEATURE:
<221> NAME/KEY: MISC_FEATURE
<222> LOCATION: (6)..(6)
<223> OTHER INFORMATION: X is Tyr or His
<220> FEATURE:
<221> NAME/KEY: MISC_FEATURE
<222> LOCATION: (8)..(8)
<223> OTHER INFORMATION: X is Thr or Ile
<220> FEATURE:
<221> NAME/KEY: MISC_FEATURE
<222> LOCATION: (9)..(9)
<223> OTHER INFORMATION: X is Gly or Ala
<220> FEATURE:
<221> NAME/KEY: MISC_FEATURE
<222> LOCATION: (10)..(10)
<223> OTHER INFORMATION: X is Val or Leu

<400> SEQUENCE: 5

Phe Gln Xaa Trp Xaa Xaa Ala Xaa Xaa Xaa Cys Gly
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: X is any naturally occurring or non natrually
      occurring amino acid
```

```
<400> SEQUENCE: 6

Trp Trp Tyr Asp Xaa Glu Tyr Tyr Tyr Leu Gly Tyr Gly Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(13)
<223> OTHER INFORMATION: X is any naturally occurring or non natrually
      occurring amino acid

<400> SEQUENCE: 7

Trp Gly Trp Phe Asp Asn Leu Tyr Trp Tyr Val Xaa Xaa Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: X is Leu, Gln, Thr, Asn, Glu, or Asp
<220> FEATURE:
<221> NAME/KEY: MISC_FEATURE
<222> LOCATION: (9)..(9)
<223> OTHER INFORMATION: X is Leu, or Tyr
<220> FEATURE:
<221> NAME/KEY: MISC_FEATURE
<222> LOCATION: (10)..(10)
<223> OTHER INFORMATION: X is Phe or Tyr
<220> FEATURE:
<221> NAME/KEY: MISC_FEATURE
<222> LOCATION: (11)..(11)
<223> OTHER INFORMATION: X is Val or Leu

<400> SEQUENCE: 8

Trp Gly Trp Phe Asp Asp Xaa Tyr Xaa Xaa Xaa Ala Tyr Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: X is any naturally occurring or non natrually
      occurring amino acid

<400> SEQUENCE: 9

Trp Leu Tyr Leu Asp Asp Xaa Gly Asp Trp Trp Ile Cys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (4)..(4)
<223> OTHER INFORMATION: X is any naturally occurring or non natrually
      occurring amino acid

<400> SEQUENCE: 10

Trp Tyr Asp Xaa Glu Tyr Tyr Tyr Leu Gly Tyr Gly Cys Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(12)
<223> OTHER INFORMATION: X is any naturally occurring or non natrually
      occurring amino acid

<400> SEQUENCE: 11

Gly Trp Phe Asp Asn Leu Tyr Trp Tyr Val Xaa Xaa Cys Gly
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is Leu, Gln, Thr, Asn, Glu, or Asp
<220> FEATURE:
<221> NAME/KEY: MISC_FEATURE
<222> LOCATION: (8)..(8)
<223> OTHER INFORMATION: X is Leu or Tyr
<220> FEATURE:
<221> NAME/KEY: MISC_FEATURE
<222> LOCATION: (9)..(9)
<223> OTHER INFORMATION: X is Phe or Tyr
<220> FEATURE:
<221> NAME/KEY: MISC_FEATURE
<222> LOCATION: (10)..(10)
<223> OTHER INFORMATION: X is Val or Leu

<400> SEQUENCE: 12

Gly Trp Phe Asp Asp Xaa Tyr Xaa Xaa Xaa Ala Tyr Cys Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is any naturally occurring or non natrually
      occurring amino acid

<400> SEQUENCE: 13

Leu Tyr Leu Asp Asp Xaa Gly Asp Trp Trp Ile Cys Gly
1               5                   10

<210> SEQ ID NO 14
<211> LENGTH: 15
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Tryptophan

<400> SEQUENCE: 14

Trp Trp Tyr Asp Arg Glu Tyr Tyr Leu Gly Tyr Gly Cys Gly
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Tryptophan

<400> SEQUENCE: 15

Trp Gly Trp Phe Asp Asn Leu Tyr Trp Tyr Val Thr His Cys Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Tryptophan

<400> SEQUENCE: 16

Trp Gly Trp Phe Asp Asp Leu Tyr Leu Phe Val Ala Tyr Cys Gly
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Tryptophan

<400> SEQUENCE: 17

Trp Leu Tyr Leu Asp Asp Ser Gly Asp Trp Trp Ile Cys Gly
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic

<400> SEQUENCE: 18

Gly Trp Phe Asp Asp Gln Tyr Leu Phe Val Ala Tyr Cys
1               5                   10

<210> SEQ ID NO 19
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 19

Gly Trp Phe Asp Asp Thr Tyr Leu Phe Val Ala Tyr Cys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic

<400> SEQUENCE: 20

Gly Trp Phe Asp Asp Asn Tyr Leu Phe Val Ala Tyr Cys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

Gly Trp Phe Asp Asp Glu Tyr Leu Phe Val Ala Tyr Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic

<400> SEQUENCE: 22

Gly Trp Phe Asp Asp Asp Tyr Leu Phe Val Ala Tyr Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic

<400> SEQUENCE: 23

Gly Trp Phe Asp Asp Leu Tyr Trp Phe Val Ala Tyr Cys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Gly Trp Phe Asp Asp Leu Tyr Tyr Phe Val Ala Tyr Cys
1               5                   10

<210> SEQ ID NO 25
<211> LENGTH: 13
<212> TYPE: PRT
```

```
<213> ORGANISM: Artificial Sequence
<220> FEATURE:
<223> OTHER INFORMATION: Synthetic

<400> SEQUENCE: 25

Gly Trp Phe Asp Asp Leu Tyr Leu Tyr Val Ala Tyr Cys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic

<400> SEQUENCE: 26

Gly Trp Phe Asp Asp Leu Tyr Leu Phe Tyr Ala Tyr Cys
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Gly Trp Phe Asp Asp Leu Tyr Leu Phe Leu Ala Tyr Cys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic

<400> SEQUENCE: 28

Gly Trp Phe Asp Asp Glu Tyr Trp Phe Tyr Ala Tyr Cys
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Gly Trp Phe Asp Asp Leu Tyr Trp Tyr Tyr Ala Tyr Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

Gly Trp Phe Asp Asp Glu Tyr Trp Tyr Tyr Ala Tyr Cys
1               5                   10

<210> SEQ ID NO 31
<211> LENGTH: 13
<212> TYPE: PRT
<213> ORGANISM: Artificial Sequence
```

```
<220> FEATURE:
<223> OTHER INFORMATION: Synthetic

<400> SEQUENCE: 31

Gly Trp Phe Asp Asp Gln Tyr Trp Tyr Tyr Ala Tyr Cys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic

<400> SEQUENCE: 32

Gly Trp Phe Asp Asp Asn Tyr Trp Tyr Tyr Ala Tyr Cys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic

<400> SEQUENCE: 33

Gly Trp Phe Asp Asp His Tyr Trp Tyr Tyr Ala Tyr Cys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

Gly Trp Phe Asp Asp Lys Tyr Trp Tyr Tyr Ala Tyr Cys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Orn

<400> SEQUENCE: 35

Phe Gln Tyr Trp Xaa Tyr Ala Thr Gly Val Cys Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Orn

<400> SEQUENCE: 36

Phe Gln Leu Trp Xaa His Ala Ile Ala Leu Cys Gly
```

<210> SEQ ID NO 37
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Phenylalanine
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 37

Phe Gln Tyr Trp Xaa Tyr Ala Thr Gly Val Cys Gly
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-isomer Phenylalanine
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: METHYLATION
<220> FEATURE:
<221> NAME/KEY: MOD_RES
<222> LOCATION: (8)..(8)
<223> OTHER INFORMATION: METHYLATION

<400> SEQUENCE: 38

Phe Gln Leu Trp Xaa His Ala Ile Ala Leu Cys Gly
1               5                   10

<210> SEQ ID NO 39
<211> LENGTH: 66
<212> TYPE: DNA
<213> ORGANISM: Artificial Sequence
<220> FEATURE:
<223> OTHER INFORMATION: Synthetic

<400> SEQUENCE: 39
ggcgtaatac gactcactat aggatcgaaa gatttccgcg gccccgaaag gggattagcg    60
ttaggt                                                              66

<210> SEQ ID NO 40
<211> LENGTH: 45
<212> TYPE: DNA
<213> ORGANISM: Artificial Sequence -continued
<220> FEATURE:
<223> OTHER INFORMATION: Synthetic

<400> SEQUENCE: 40
ggaucgaaag auuccgcgg ccccgaaagg ggauuagcgu uaggu    45

<210> SEQ ID NO 41
<211> LENGTH: 98
<212> TYPE: DNA
<213> ORGANISM: Artificial Sequence
<220> FEATURE:
<223> OTHER INFORMATION: Synthetic

<400> SEQUENCE: 41
ggcgtaatac gactcactat aggcggggtg gagcagcctg gtagctcgtc gggctcataa    60
cccgaagatc gtcggttcaa atccggcccc cgcaacca    98

<210> SEQ ID NO 42
<211> LENGTH: 77
<212> TYPE: DNA
<213> ORGANISM: Artificial Sequence
<220> FEATURE:
<223> OTHER INFORMATION: Synthetic

<400> SEQUENCE: 42
ggcggggugg agcagccugg uagcucgucg ggcucauaac ccgaagaucg ucgguucaaa    60 uccggcccc gcaacca    77

<210> SEQ ID NO 43
<211> LENGTH: 16
<212> TYPE: DNA
<213> ORGANISM: Artificial Sequence
<220> FEATURE:
<223> OTHER INFORMATION: Synthetic

<400> SEQUENCE: 43
ctcccgcccc ccgtcc    16

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Gly Trp Phe Asp Asp Leu Tyr Leu Phe Val Ala Tyr Cys
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

Trp Gly Trp Trp Leu Asn Glu Trp Leu Tyr Tyr Ala Pro Cys Gly
1               5                   10                  15

<210> SEQ ID NO 46
<211> LENGTH: 15
<212> TYPE: PRT
<213> ORGANISM: Artificial Sequence
<220> FEATURE:

```
<223> OTHER INFORMATION: Synthetic

<400> SEQUENCE: 46

Trp Gly Trp Phe Asn Ala Asn Tyr Leu Tyr Tyr Ala Cys Cys Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Trp Leu Ala Asp Phe Arg Glu Tyr Ile Ile Ile Trp Asp Cys Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48

Trp Gly Tyr Tyr Asp Glu Leu Trp Trp Tyr Val Ala Ser Cys Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

Trp Gly Trp Trp Asp Gln Phe Tyr Thr Tyr Tyr Ser Pro Cys Gly
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic

<400> SEQUENCE: 50

Trp Gly Trp Phe Asp Asp Leu Tyr Trp Tyr Val Thr His Cys Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Trp Gly Trp Phe Asp Asn Leu Tyr Trp Tyr Val Ala His Cys Gly
1               5                   10                  15

<210> SEQ ID NO 52
<211> LENGTH: 14
<212> TYPE: PRT
<213> ORGANISM: Artificial Sequence
<220> FEATURE:
<223> OTHER INFORMATION: Synthetic
```

<400> SEQUENCE: 52

Trp Phe Ser Cys Tyr Trp Pro His Asp Tyr Asp His Cys Gly
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is any amino acid

<400> SEQUENCE: 53

Trp Trp Trp Asp Glu Xaa Trp Tyr Tyr Leu Val Ala Asp Cys Gly
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic

<400> SEQUENCE: 54

Trp Gly Trp Leu Asp Asn Leu Tyr Trp Tyr Val Thr His Cys Gly
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic

<400> SEQUENCE: 55

Trp Gly Trp Phe Asp Ser His Tyr Leu Tyr His Asn Pro Cys Gly
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Trp Gly Trp Phe Asn Ala Asn Tyr Leu Tyr Tyr Ala Ser Cys Gly
1               5                   10                  15

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

Trp Tyr Val Phe Tyr Glu Pro Tyr Tyr Ile Pro Cys Gly
1               5                   10

<210> SEQ ID NO 58
<211> LENGTH: 15
<212> TYPE: PRT

<213> ORGANISM: Artificial Sequence
<220> FEATURE:
<223> OTHER INFORMATION: Synthetic

<400> SEQUENCE: 58

Trp Gly Trp Phe Asp Asn Leu Tyr Trp His Val Thr His Cys Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Trp Gly Trp Phe Asp Asn Leu Tyr Trp Tyr Ala Thr His Cys Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic

<400> SEQUENCE: 60

Trp Gly Trp Phe Asp Asn Leu His Trp Tyr Val Thr His Cys Gly
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Trp Trp Tyr Val Gly Tyr Gln Tyr Tyr Phe Leu Val Ala Cys Gly
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic

<400> SEQUENCE: 62

Trp Leu Phe Leu Gly Tyr Asp Arg Leu Phe Val Ile Asn Cys Gly
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic

<400> SEQUENCE: 63

Trp Gly Trp Val Asp Asn Leu Tyr Trp Tyr Val Thr His Cys Gly
1               5                   10                  15

<210> SEQ ID NO 64
<211> LENGTH: 15
<212> TYPE: PRT
<213> ORGANISM: Artificial Sequence

```
<220> FEATURE:
<223> OTHER INFORMATION: Synthetic

<400> SEQUENCE: 64

Trp Leu Tyr Gln Gly His Val Leu Tyr Phe Tyr Val Asp Cys Gly
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic

<400> SEQUENCE: 65

Trp Gly Trp Phe Asp Asn Leu Tyr Trp Asp Val Thr His Cys Gly
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic

<400> SEQUENCE: 66

Trp Gly Trp Phe Asp Asn Ser His Tyr Leu Tyr His Asn Pro Cys Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic

<400> SEQUENCE: 67

Trp Gly Trp Phe Asp Asn Leu Tyr Trp Asn Val Thr His Cys Gly
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic

<400> SEQUENCE: 68

Trp Gly Trp Phe Asp Ser Leu Tyr Trp Tyr Val Thr His Cys Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

Trp Gly Trp Phe Asp Asn Leu Asp Trp Tyr Val Thr His Cys Gly
1               5                   10                  15

<210> SEQ ID NO 70
<211> LENGTH: 15
<212> TYPE: PRT
<213> ORGANISM: Artificial Sequence
<220> FEATURE:
```

<223> OTHER INFORMATION: Synthetic

<400> SEQUENCE: 70

Trp Gly Trp Phe Asp Glu Gln Phe Trp Tyr His His Pro Cys Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic

<400> SEQUENCE: 71

Trp Gly Trp Tyr Asp Asp His Phe Tyr Tyr Leu Ala Ser Cys Gly
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Trp His Trp Trp Asp Asp Ala Trp Glu Tyr Tyr Phe Ala Cys Gly
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic

<400> SEQUENCE: 73

Trp Gly Trp Phe Ser Glu Asn Tyr Tyr Phe Tyr Ala Ser Cys Gly
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic

<400> SEQUENCE: 74

Trp Gly Trp Phe Asn Thr Glu Tyr Leu Phe Trp Ala Asp Cys Gly
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic

<400> SEQUENCE: 75

Trp Tyr Trp Phe Asp Asp Arg Tyr Glu Tyr Trp Phe His Cys Gly
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic

```
<400> SEQUENCE: 76

Trp Gly Tyr Tyr Asp Asp Phe Tyr Trp Tyr Tyr Val Ala Cys Gly
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic

<400> SEQUENCE: 77

Trp Gly Trp Phe Ser Gly Tyr Asp Trp Tyr Tyr Ser Pro Cys Gly
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Trp Gly Trp Phe Asp Asp Asn Tyr Thr Tyr Arg Ala His Cys Gly
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic

<400> SEQUENCE: 79

Trp Gly Tyr Trp Asp Asp Ser Leu Tyr Trp Ala Asn Cys Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

Trp Gly Tyr Trp Asp Asn Asp Tyr Leu Tyr Phe Ala His Cys Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic

<400> SEQUENCE: 81

Trp Gly Trp Phe Asp Glu Asp Phe Leu Phe Leu Ala Phe Cys Gly
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 82

Trp Gly Trp Phe Asp Tyr Ala Ala Leu Tyr Tyr Ala Ser Cys Gly
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic

<400> SEQUENCE: 83

Trp Gly Trp Phe Thr Asp Thr Trp Leu Tyr Trp Ser Pro Cys Gly
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic

<400> SEQUENCE: 84

Trp Gly Trp Phe Asp Glu Val Tyr Thr Tyr Leu Ala Val Cys Gly
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic

<400> SEQUENCE: 85

Trp Ala Trp Trp Phe Asp Glu Tyr Trp Tyr Val Tyr Phe Cys Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic

<400> SEQUENCE: 86

Trp Gly Trp Phe Asp Asp Tyr Trp Tyr Ser Ser Ala Cys Gly
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic

<400> SEQUENCE: 87

Trp Gly Trp Phe Glu Gly Asn Glu Leu Tyr Tyr Ala Ser Cys Gly
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88
```

```
Trp Gly Trp Phe Asp Thr Leu Tyr Val Phe Trp Ser Pro Cys Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

Trp Trp Phe Asp Asp Asn His Leu Tyr Leu Ser Leu Ser Cys Gly
1               5                   10                  15

<210> SEQ ID NO 90
<211> LENGTH: 76
<212> TYPE: PRT
<213> ORGANISM: Artificial Sequence
<220> FEATURE:
<223> OTHER INFORMATION: Synthetic

<400> SEQUENCE: 90

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Arg Glu
    50                  55                  60

Ser Thr Leu His Leu Val Leu Arg Leu Arg Gly Gly
65                  70                  75
```

UBIQUITIN HIGH AFFINITY CYCLIC PEPTIDES AND METHODS OF USE THEREOF

CROSS-REFERENCE

This application is a National Phase of PCT Patent Application No. PCT/IL2019/050654 having International filing date of Jun. 6, 2019, which claims the benefit of priority to U.S. Provisional Patent Application Nos. 62/681,389 filed Jun. 6, 2018, and 62/793,470 filed Jan. 17, 2019, both entitled "UBIQUITIN HIGH AFFINITY CYCLIC PEPTIDES AND METHODS OF USE THEREOF", the contents of which are incorporated herein by reference in their entirety.

FIELD OF INVENTION

The present invention is in the field of peptide engineering and drug screening.

BACKGROUND OF THE INVENTION

The initial and obligatory step in ubiquitin (Ub) signaling is the ATP-dependent modification of the protein substrate by Ub or poly Ub chains. The formation of poly Ub chains is achieved by the collaborative action of three enzymes, known as E1, E2 and E3. The most studied Ub chain is the K48-linked chain, which is known to adopt a compact structure and target the modified protein to proteasomal degradation.

Ubiquitination is a major post-translational modification affecting many aspects of cell biology and has been linked to various diseases such as cancer. Several tumor suppressors or oncogenes involved in Ub conjugation and deconjugation pathways are altered in cancerous states, making the Ub system an excellent target for cancer therapy. In particular, the ubiquitin-proteasome system (UPS) has proven to be a valid target for anti-cancer drug development as exemplified by the approval of the small molecule Bortezomib, for the treatment of multiple myeloma and mantle cell lymphoma.

Another approach is targeting the Ub chain itself. This offers great potential for interfering with Ub signaling compared to targeting individual Ub-modifying enzymes. In this regard, the small molecules 'ubistatins' emerged from a chemical genetic screen and were found to bind mono Ub and K48-linked chains, and thereby impair recognition by the proteasome and inhibit protease degradation. However, ubistatins suffer from poor cell permeability, weak µM binding and poor chain specificity.

Targeting Ub chains of particular lengths and linkages may be advantageous and influence specific cellular processes. However, this represents a significant challenge for molecular recognition, given the number of possible Ub chains and the often-subtle differences in their structure and dynamics.

To this end, there is still a need for a molecule or a compound having specific binding affinity to mono Ub and particularly K48-linked chains, wherein the molecule or compound is capable of sufficiently penetrate a living cell.

SUMMARY OF THE INVENTION

The present invention is directed to a cyclic polypeptide and methods of using same, such as for reducing deubiquitination activity of a cell or for ameliorating, or treating cancer in a subject in need thereof. The present invention is based, in part, on the findings that cyclic polypeptides bind ubiquitin polymers with an affinity $K_D$ at a nanomolar level. The present invention is further based, in part, on the surprising finding that cyclic polypeptides are capable of penetrating into a cell and bind to polymeric ubiquitin in vivo.

According to one aspect, there is provided a cyclic polypeptide comprising an amino acid sequence selected from the group consisting of: LYLDDX$_1$GDWWIC (SEQ ID NO: 4); WYDX$_1$EYYYLGYGC (SEQ ID NO: 1); GWFDNLYWYVX$_1$X$_1$C (SEQ ID NO: 2); and GWFDDX$_2$YX$_3$X$_4$X$_5$AYC (SEQ ID NO: 3); wherein X$_1$ is an amino acid selected from: (i) naturally occurring amino acids; or (ii) non-naturally occurring amino acids, and wherein X2 is an amino acid selected from the group consisting of: Leu, Gln, Thr, Asn, Glu, and Asp, and wherein X3 is an amino acid selected from the group consisting of: Leu, and Tyr, and wherein X4 is an amino acid selected from the group consisting of: Phe and Tyr, and wherein X5 is an amino acid selected from the group consisting of: Val and Leu.

According to another aspect, there is provided a cyclic polypeptide comprising the amino acid sequence FQX$_1$WOX$_2$AX$_3$X$_4$X$_5$CG (SEQ ID NO: 5), wherein X$_1$ is an amino acid selected from: Tyr or Leu, X$_2$ is an amino acid selected from: Tyr or His, X$_3$ is an amino acid selected from: Thr or Ile, X$_4$ is an amino acid selected from: Gly or Ala, and X$_5$ is an amino acids selected from: Val or Leu.

According to another aspect, there is provided a method for reducing deubiquitination activity of a cell, the method comprising contacting the cell with a cyclic polypeptide having a ubiquitin binding affinity $K_D$ of 0.05-100 nM, and wherein at least 55% of amino acids of said cyclic polypeptide are selected from the group consisting of: W, G, F, D, L, Y and C.

According to another aspect, there is provided a method for ameliorating or treating cancer in a subject in need thereof, the method comprising administering to the subject a therapeutically effective amount of a cyclic polypeptide, wherein the polypeptide binds ubiquitin with an affinity $K_D$ of 0.05-100 nM, and wherein at least 55% of amino acids of said cyclic polypeptide are selected from the group consisting of: W, G, F, D, L, Y and C.

In some embodiments, any one of the amino acid sequences set forth in SEQ ID Nos: 1-4 further comprises a Trp amino acid residue at the N' terminus.

In some embodiments, any one of the amino acid sequences set forth in SEQ ID Nos: 1-4 further comprises a Gly amino acid reside at the C' terminus.

In some embodiments, the cyclic polypeptide comprises the amino acid sequences as set forth in any one of: WWYDX$_1$EYYYLGYGCG (SEQ ID NO: 14); WGWFDNLYWYVX$_1$X$_1$CG (SEQ ID NO: 15); WGWFDDX$_2$YX$_3$X$_4$X$_5$AYCG (SEQ ID NO: 16); WLYLDDX$_1$GDWWICG (SEQ ID NO: 17).

In some embodiments, a non-naturally occurring amino acid is selected from the group consisting of: Abu, Nva, Nle, Ahp, Aoc, TMe, hSM, tBu, Cpa, Cha, Alb, MeG, MeA, MeB, MeF, 2Th, 3Th, YMe, 2Np, Bzt and DAL In some embodiments, the cyclic polypeptide comprises an amino acid sequence selected from the group consisting of: GWFDDQYLFVAYC (SEQ ID NO: 18); GWFDDTYLFVAYC (SEQ ID NO: 19); GWFDDNYLFVAYC (SEQ ID NO: 20); GWFDDEYLFVAYC (SEQ ID NO: 21); GWFDDDYLFVAYC (SEQ ID NO: 22); GWFDDLYWFVAYC (SEQ ID NO: 23); GWFD- DLYYFVAYC (SEQ ID NO: 24); GWFDDLYLYVAYC (SEQ ID NO: 25); GWFDDLYLFYAYC (SEQ ID NO: 26); GWFDDLYLFLAYC (SEQ ID NO: 27); GWFDDEYWFYAYC (SEQ ID NO: 28); GWFDDLYWYYAYC (SEQ ID NO: 29); GWFDDEYWYYAYC (SEQ ID NO: 30); GWFDDQYWYYAYC (SEQ ID NO: 31); GWFDDNYWYYAYC (SEQ ID NO: 32); GWFDDHYWYYAYC (SEQ ID NO: 33); GWFDDKYWYYAYC (SEQ ID NO: 34); and GWFDDLYLFVAYC (SEQ ID NO: 44).

In some embodiments, the cyclic polypeptide comprises an amino acid sequence selected from the group consisting of: FQYWOYATGVCG (SEQ ID NO: 35); and FQLWOHAIALCG (SEQ ID NO: 36).

In some embodiments, the amino acid residues at position 6, 8 or both, of SEQ ID Nos.: 35-36 are methylated.

In some embodiments, polypeptide comprises not more than 16 amino acid residues.

In some embodiments, the amino acid at position one is a D amino acid.

In some embodiments, the amino acid at position one is conjugated to a cyclizing molecule.

In some embodiments, the cyclic polypeptide is prepared using a cyclizing molecule comprising a halogen.

In some embodiments, the cyclizing molecule is selected from the group consisting of: chloracetyl chloride, 3-chlorobenzoyl (3-ClBz), 4-chlorobenzoyl (4-ClBz) or Cl$_2$SAc.

In some embodiments, the cyclic polypeptide is characterized as having: cell penetration capability, ubiquitin (Ub) binding capability, or a combination thereof.

In some embodiments, the cyclic polypeptide has increased affinity to Ub compared to control.

In some embodiments, Ub is a polymeric Ub.

In some embodiments, the polymeric Ub comprises Ub monomers linked at their K48 position ($^{K48}$Ub).

In some embodiments, increased affinity is binding affinity $K_D$ of 0.05-100 nM.

In some embodiments, the cyclic polypeptide reduces deubiquitination activity of a cell by at least 30%.

In some embodiments, the cyclic polypeptide reduces ubiquitinated proteins proteasomal degradation rate by at least 40%.

In some embodiments, the cyclic polypeptide has increased pro-apoptotic activity compared to control.

In some embodiments, increased pro-apoptotic activity results in at least 20% more cell apoptosis compared to control.

In some embodiments, the cyclic polypeptide reduces cell viability with an IC$_{50}$ of 0.05-15 μM.

In some embodiments, a composition comprising the disclosed cyclic polypeptide and at least one acceptable carrier or diluent is provided.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1H are images and graphs describing the random non-standard peptides integrated discovery (RaPID) selection of $^{K48}$Ub$_n$ binding cyclic peptides. (1A) is a scheme of the chemical synthesis of biotin-K48-linked di/tetra-Ub chain. (1B) is a chemical structure and an illustration of Flexizyme, an artificial tRNA aminoacylation ribozyme, capable of loading non-canonical amino acids (gray, gray circle) onto tRNA (black), for use by the ribosome in in vitro translation. Non-canonical amino acids with a N-terminal ClAc group spontaneously react with intramolecular cysteine and can be used to form macrocyclic peptides. (1C) is a flow chart delineating how large libraries (~10$^{13}$) of DNA-tagged macrocyclic peptides can be generated in the RaPID system, from which sequences can be isolated to tight bind a protein target. (1D) are graphs showing RaPID DNA libraries enrichment using different targets. Using $^{K48}$Ub$_2$ as a target, RaPID DNA libraries became enriched in certain peptide sequences (grey lines), with Ub2i and Ub2ii (black) as the dominant peptides (selection repeat shown as dashed lines). Using $^{K48}$Ub$_4$ as a target, Ub4i and Ub4ix (black) emerged amongst the enriched peptides. (1E-1H) is the chemical structures and the corresponding surface plasmon resonance (SPR) binding curves of $^{K48}$Ub$_2$ (left) and $^{K48}$Ub$_4$ (right) to the following synthesized peptides: Ub2i (1E), Ub2ii (1F), Ub4i (1G), and Ub4ix (1H). Highest and lowest peptide SPR concentrations including dissociation constants ($K_D$), are shown.

FIGS. 2A-2E are graphs and images showing that cyclic peptides bind to residues at the hydrophobic Ub-Ub interface in K48-linked di- and tetra-Ub. (2A) is an overlay graph of the $^1$H-$^{15}$N correlation spectra of $^{K48}$Ub$_2$ (proximal Ub) free (blue) and in the presence of 1 molar equivalent of Ub2ii. Signal shifts for select residues are indicated. Insets on the right illustrate the behavior of the signal of Q40 (boxed) during the titration with the peptide, at the indicated Ub$_2$:peptide molar ratios. (2B) is vertical bar graphs of residue-specific chemical shift perturbations at the endpoint of titration with Ub$_2$ii in the distal (Left) and proximal (Right) Ub units in $^{K48}$Ub$_2$. (2C) is an image of the crystal structure of the closed state of $^{K48}$Ub$_2$ (PDB 1AAR) on which the perturbed residues were mapped (green). (2D) is vertical bar graphs of (Left) comparison of the intensities of the unbound signals of the most distal (unit 4, black bars) and the next to distal (unit 3, gray bars) Ub units in $^{K48}$Ub$_4$ upon addition of the Ub4ix peptide in 2:1 and 1.5:1 molar ratio to Ub$_4$, respectively. The signal intensity for each residue was normalized to the corresponding intensity in the absence of peptide. (Right) A similar comparison of the signal intensities in Ub$_4$ unit 3 (gray) versus the distal Ub in $^{K48}$Ub$_3$ (Ub$_3$ unit 3, black), both at the 1.5:1 molar ratio (peptide:Ub$_4$). The drawings on top indicate which Ub units in Ub$_4$ and Ub$_3$ are analyzed. Asterisks in (2B) and (2D) indicate residues that could not be detected or could not be reliably quantified due to signal overlap. (2E) is an image mapping the residues showing strong signal shifts or attenuations (green) in the two distal Ub units (4 and 3) of $^{K48}$Ub$_4$ on the crystal structure of the closed form of $^{K48}$Ub$_4$ (PDB 2O6V).

FIGS. 3A-3D are images of western blot analyses of K48-di/tetra-Ub incubated with active deubiquitinating enzymes (DUBs) and panel of cyclic peptides. (3A) $^{K48}$Ub$_2$ was incubated with active OTUB1 and UBCH5B (E2 enzyme). (3B) $^{K48}$Ub$_4$ was incubated with active OTUB1 and the cyclic peptides. (3C) $^{K48}$Ub$_2$ was incubated for 1 hour with active USP2 and the cyclic peptides; and (3D) $^{K48}$Ub$_4$ was incubated for 1 hour with active USP2 and the cyclic peptides. The same amounts were loaded on 14% SDS-PAGE, electro-blotted to nitrocellulose membrane and probed with an anti-Ub antibody.

FIGS. 4A-4B are an illustration and an image of a western blot analysis showing the effect of Ub4ix cyclic peptide on the proteasomal activity. (4A) is a schematic diagram displaying the effects of Ub4ix treatment on the proteasome activity. (4B) is a western blot analysis on the effect of proteasome inhibition on HA-α-globin-K48-linked tetra-Ub degradation in vitro following 25 min of treatment with Ub4ix and linear_Ub4ix. Lane 1: zero time and lane 2: Untreated cells (positive control). The same amount of HA-α-globin-K48-linked tetra-Ub (5.3 μM) and 26S proteasome (150 nM) were add to the reaction mixture, then loaded on 10% SDS-PAGE, electro-blotted to nitrocellulose membrane and probed with an anti-HA antibody.

FIGS. 8A-8D are graphs and an image of a western blot analysis showing the characterization of biotin-$^{K48}$Ub$_{2,4}$ chains. (8A) is a chromatogram of analytical HPLC and ESI-MS of the purified biotin-$^{K48}$Ub$_4$ with the observed mass 34,473±1.3 Da (calculated 34,473.3). (8B) is a chromatogram of analytical HPLC and ESI-MS of the biotin-$^{K48}$Ub$_2$ with the observed mass 17,413.5±0.8 Da (calculated 17,413). (8C) is a graph of a circular dichroism (CD) analyses of the native biotin-$^{K48}$Ub$_{2,4}$ revealing a correct folding compared to the secondary structure of Ub; and (8D) is an image of SDS-PAGE gel of the purified biotin-$^{K48}$Ub$_{2,4}$ chains.

FIGS. 10A-10B are images describing the structure and symmetry of K48-linked Ub chains. (10A) is an image of the topology of the $^{K48}$Ub$_2$ and $^{K48}$Ub$_4$ sequences, with the isopeptide bonds. (10B) is an image of a three-dimensional structure of $^{K48}$Ub$_2$ (blue), pdb 1AAR showing the rotational symmetry. Structure of $^{K48}$Ub$_2$ (white), pdb 2O6V. $^{K48}$Ub$_2$ can be superimposed twice on $^{K48}$Ub$_4$, or four times if the isopeptide linkage is not considered.

FIG. 13 is an illustration and a graph of a chromatogram of an analytical HPLC and ESI-MS analysis of a synthesized fluorescein-5-maleimide-Ub4ix cyclic peptide. The purified fluorescein-5-maleimide-Ub4ix cyclic peptide was observed with a mass of 2,368.5±0.1 Da (calculated 2,368.5 Da).

FIGS. 14A-14B are images of western blot analyses demonstrating cyclic peptides selectivity to K48-linked chains. (14A) $^{K63}Ub_2$ was incubated for 1 hour with active USP2 enzyme and panel of cyclic peptides. (14B) $^{K11}Ub_2$ was incubated with active Cezanne enzyme and Ub2ii or Ub4ix cyclic peptides for 1 hour. The same amounts were loaded on 14% SDS-PAGE, electro-blotted to nitrocellulose membrane and probed with an anti-Ub antibody.

FIGS. 31A-31B are images of western blot analyses demonstrating cyclic peptides selectivity to K48-linked chains. (31A) $^{K63}$Ub$_2$ was incubated for 1 hour with active USP2 enzyme and Ub$_4$_a and Ub$_4$_e cyclic peptides. (31B) $^{K11}$Ub$_2$ was incubated with active Cezanne enzyme and Ub$_4$_a cyclic peptide for 1 hour. The same amounts were loaded on 14% SDS-PAGE, electro-blotted to nitrocellulose membrane and probed with an anti-Ub antibody.

FIGS. 32A-32B are an illustration and an image of a western-blot analysis showing the characterization of the effect of Ub$_4$_a and Ub$_4$_e cyclic peptides on the proteasomal activity. (32A) is a schematic diagram displaying the effects of Ub$_4$_a and Ub$_4$_e treatments on the proteasome activity. (32B) is a western blot analysis on the effect of proteasome inhibition on HA-α-globin-K48-linked tetra-Ub degradation in vitro following 25 min of treatment with Ub$_4$_a or Ub$_4$_e. Lane 1: zero time and lane 2: Untreated cells (positive control). The same amount of HA-α-globin-K48-linked tetra-Ub (5.3 µM) and 26S proteasome (150 nM) were add to the reaction mixture, then loaded on 10% SDS-PAGE, electro-blotted to nitrocellulose membrane and probed with an anti-HA antibody.

FIGS. 37A-37E are graphs and images demonstrating the characterization of J08_mClBz_L8W. (37A) is a surface plasmon resonance (SPR) binding curves showing binding of showing J08_mClBz_L8W to K48-Ub2. (37B-37C) is images of western blot analyses of K48-di-Ub incubated with active deubiquitinating enzymes (DUBs) and J08_L8W and Ub4i cyclic peptides. (37B) $^{K48}$Ub$_2$ was incubated with active OTUB1. (37C) $^{K48}$Ub$_2$ was incubated with active USP2 and the cyclic peptides. The same amounts were loaded on 14% SDS-PAGE, electro-blotted to nitrocellulose membrane and probed with an anti-Ub antibody. (37D) is an image of western blot analysis demonstrating the effect of J08_L8W cyclic peptide on proteasomal activity. The effect of proteasome inhibition on HA-α-globin-K48-linked di-Ub degradation in vitro following 25 min of treatment with J08_L8W. Lane 2: time zero; Lane 3: Untreated cells (positive control, 25 min). Lanes 4-6: HA-α-globin-K48-linked di-Ub (5.3 µM) with 2.6 µM (lane 4) or 5.3 µM (lane 5) of the J08_L8W cyclic peptide, or 26S proteasome inhibitor (MG132, 250 nM) without cyclic peptide. All reactions were added loaded on 10% SDS-PAGE, electro-blotted to nitrocellulose membrane and probed with an anti-HA antibody. (37E) is a vertical bar graph of the effect of J08_L8W on HeLa cells apoptosis. Cells were exposed to the J08_L8W cyclic peptide or the proteasome inhibitor MG132 (e.g., positive control) for 24 and 48 h, after which FACS was used to measure % apoptosis.

FIGS. 38A-38J are fluorescent micrographs showing the uptake of Ub4ix by living cells. (38A-38E) are micrographs of U2OS osteosarcoma cells, and (38F-38J) are micrographs of U87 primary glioblastoma cells incubated in the presence of DMSO (38A, 38F, respectively), fluorescein-5-maleimide (100 nM, 38B, 38G, respectively), fluorescein-5-maleimide (300 nM, 38C, 38H, respectively), fluorescein-5-maleimide-Ub4ix cyclic peptide (100 nM, 38D, 38I, respectively), and fluorescein-5-maleimide (300 nM, 38E, 38J, respectively). Internalization of the peptide into the cells was monitored after cells were washed. Fluorescein-Ub4ix was shown to be retained in U2OS cells (38D-38E) and in U87 primary glioblastoma cells (38I-38J), whereas fluorescein alone was not retained (i.e., lost, 38A-38B, and 38F-38G).

FIGS. 39A-39B are images of western blot analyses demonstrating cyclic peptides exhibit selectivity against K48-linked chains. (39A) $^{K63}Ub_2$ was incubated for 1 hour with active USP2 enzyme and panel of cyclic peptides. (39B) $^{K11}Ub_2$ was incubated with active Cezanne enzyme and Ub2ii or Ub4ix cyclic peptides for 1 hour. The same amounts were loaded on 14% SDS-PAGE gel, electroblotted to nitrocellulose membrane and probed with anti-Ub antibody. Bands were quantified with Image Quant LAS 4000 (GE Healthcare).

FIG. 40 is a graph showing calibration of the absorption response (RFU) (ex=480, em=525 μm) from known concentrations of fluorescein-Ub4ix and fluorescein.

DETAILED DESCRIPTION OF THE INVENTION

Figure 1D:
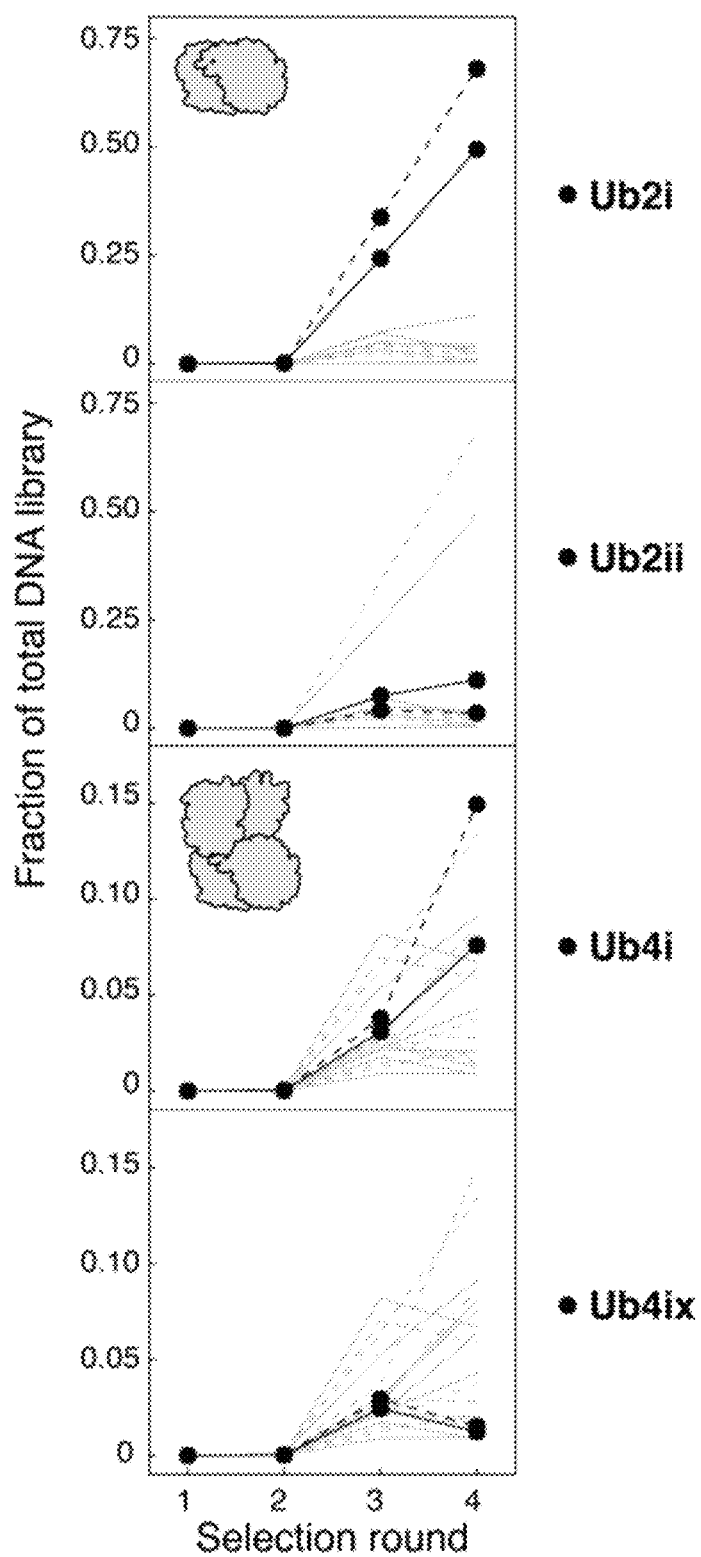
Figure 1G:
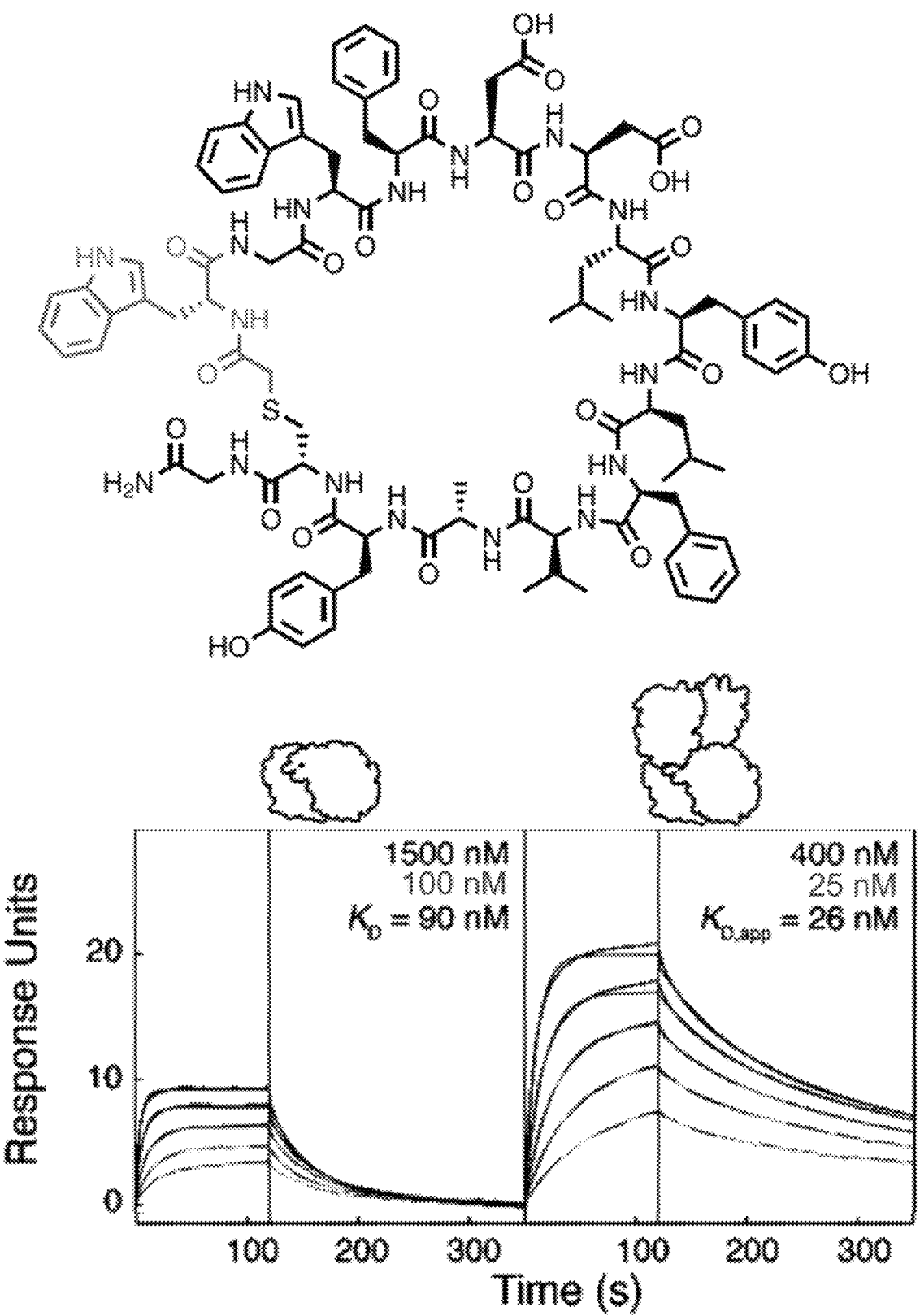

The present invention is directed to a cyclic polypeptide and methods of using same, such as for reducing deubiquitination activity of a cell or for ameliorating, or treating cancer in a subject in need thereof. The present invention is based, in part, on the findings that cyclic polypeptides bind ubiquitin polymers with an affinity $K_D$ at a nanomolar level. The present invention is further based, in part, on the surprising finding that cyclic polypeptides are capable of penetrating into a cell and bind to polymeric ubiquitin in vivo.

Polypeptides

According to some embodiments, the invention is directed to a polypeptide.

In some embodiments, the polypeptide is capable of penetrating a cell (e.g. a cancer cell), binding to ubiquitin, or combination thereof.

In some embodiments, a polypeptide of the invention comprises or consists of the amino acid sequence: WYDX$_1$EYYYLGYGC (SEQ ID NO: 1); GWFDNLYWYVX$_1$X$_1$C (SEQ ID NO: 2); GWFDDX$_2$YX$_3$X$_4$X$_5$AYC (SEQ ID NO: 3); LYLDDX$_1$GDWWIC (SEQ ID NO: 4); FQX$_6$WOX$_7$AX$_8$X$_9$X$_{10}$CG (SEQ ID NO: 5); wherein X$_1$ is an amino acid selected from: (i) naturally occurring amino acids; or (ii) non-naturally occurring amino acids, X$_2$ is an amino acid selected: Leu, Gln, Thr, Asn, Glu, or Asp, X$_3$ is an amino acid selected from: Leu, or Tyr, X$_4$ is an amino acid selected from: Phe or Tyr, X$_5$ is an amino acid selected from: Val or Leu, X$_6$ is an amino acid selected from: Tyr or Leu, X$_7$ is an amino acid selected from: Tyr or His, X$_8$ is an amino acid selected from: Thr or Ile, X$_9$ is an amino acid selected from: Gly or Ala, and X$_{10}$ is an amino acids selected from: Val or Leu.

In some embodiments, a polypeptide of the invention comprises or consists of the amino acid sequence: WWYDX$_1$EYYYLGYGC (SEQ ID NO: 6); WGWFDNLYWYVX1X$_1$C (SEQ ID NO: 7); WGWFDDX$_2$YX$_3$X$_4$X$_5$AYC (SEQ ID NO: 8); WLYLDDX$_1$GDWWIC (SEQ ID NO: 9), wherein X$_1$ is an amino acid selected from: (i) naturally occurring amino acids; or (ii) non-naturally occurring amino acids, X$_2$ is an amino acid selected from: Leu, Gln, Thr, Asn, Glu, and Asp, X$_3$ is an amino acid selected from: Leu, and Tyr, X$_4$ is an amino acid selected from: Phe and Tyr, and X$_5$ is an amino acid selected from: Val and Leu.

In some embodiments, a polypeptide of the invention comprises or consists of the amino acid sequence: WYDX$_1$EYYYLGYGCG (SEQ ID NO: 10); GWFDNLYWYVX$_1$X$_1$CG (SEQ ID NO: 11); GWFDDX$_2$YX$_3$X$_4$X$_5$AYCG (SEQ ID NO: 12); LYLDDX$_1$GDWWICG (SEQ ID NO: 13), wherein X$_1$ is an amino acid selected from: (i) naturally occurring amino acids; or (ii) non-naturally occurring amino acids, X$_2$ is an amino acid selected from: Leu, Gln, Thr, Asn, Glu, and Asp, X$_3$ is an amino acid selected from: Leu, and Tyr, X$_4$ is an amino acid selected from: Phe and Tyr, and X5 is an amino acid selected from: Val and Leu.

In some embodiments, a polypeptide of the invention comprises or consists of the amino acid sequence: *W̲WYDREYYYLGYGCG (SEQ ID NO: 14); *W̲GWFDNLYWYVTHCG (SEQ ID NO: 15); *W̲GWFDDLYLFVAYCG (SEQ ID NO: 16); *W̲LYLDDSGDWWICG (SEQ ID NO: 17); *F̲QYWOYATGVCG (SEQ ID NO: 37); *F̲QLWOHAIALCG (SEQ ID NO: 38), wherein asterisk (*) is a cyclizing molecule, amino acid highlighted by an underline is a D-isomer amino acid, and amino acid highlighted by bold is a methylated amino acid.

In some embodiments, a polypeptide of the invention comprises or consists of the amino acid sequence: *GWFDDQYLFVAYC (SEQ ID NO: 18); *GWFDDTYLFVAYC (SEQ ID NO: 19); *GWFDDNYLFVAYC (SEQ ID NO: 20); *GWFDDEYLFVAYC (SEQ ID NO: 21); *GWFDDDYLFVAYC (SEQ ID NO: 22); *GWFDDLYWFVAYC (SEQ ID NO: 23); *GWFDDLYYFVAYC (SEQ ID NO: 24); *GWFDDLYLYVAYC (SEQ ID NO: 25); *GWFDDLYLFYAYC (SEQ ID NO: 26); *GWFDDLYLFLAYC (SEQ ID NO: 27); *GWFDDEYWFYAYC (SEQ ID NO: 28); *GWFDDLYWYYAYC (SEQ ID NO: 29); *GWFDDEYWYYAYC (SEQ ID NO: 30); *GWFDDQYWYYAYC (SEQ ID NO: 31); *GWFDDNYWYYAYC (SEQ ID NO: 32); *GWFDDHYWYYAYC (SEQ ID NO: 33); *GWFDDKYWYYAYC (SEQ ID NO: 34), wherein asterisk (*) is a cyclizing molecule.

In some embodiments, a polypeptide of the invention comprises or consists of the amino acid sequence: FQYWOYATGVCG (SEQ ID NO: 35); and FQLWOHAIALCG (SEQ ID NO: 36).

The amino acid Ornithine is represented by the code letter "O".

In some embodiments, a polypeptide of the invention is linear or cyclic.

As defined herein, the amino acid sequence of a polypeptide of the invention (SEQ ID Nos.: 1-38) is cited from its N-terminus to the C-terminus. In some embodiments, amino acid residue positioned at the N-terminus of a polypeptide is located at the first position of the polypeptide. In some embodiments, a cited position of a given amino acid residue within a cyclic polypeptide is referred to, based on the position of the amino acid residue in the linear form of the polypeptide.

In some embodiments, a cyclic polypeptide of the invention is having increased affinity to a ubiquitin molecule. In some embodiments, a ubiquitin molecule is a ubiquitin dimer, trimer, tetramer or a heptamer. Each possibility represents a separate embodiment of the invention.

In some embodiments, a cyclic polypeptide of the invention having increased affinity to dimeric ubiquitin comprises or consists of the amino acid sequence WWYDXEYYYLGYGCG (SEQ ID NO: 1), wherein Xis any amino acid selected from: Gly, Ala, Ser, Thr, Leu, Ile, Asp, Glu, Asn, Gln, Lys, His, Tyr, Phe, Abu, Nva, Nle, Ahp, TMe, hSM, tBu, Cpa, Cha, Aib, MeG, MeA, MeB, MeF, 2Th, 3Th, and DAl In some embodiments, a cyclic polypeptide of the invention having increased affinity to dimeric ubiquitin comprises or consists of the amino acid sequence: WGWFDNLYWYX$_1$X$_2$X$_3$CG (SEQ ID NO: 2), wherein X$_1$ is any amino acid selected from: Trp, Tyr, Phe, Nva, Ahp, tBu, 2Th, 3Th, YMe, 2Np and Bzt, X$_2$ is any amino acid selected from: Gly, Ala, Thr, Val, Abu, Nva, Ahp, MeG, 2Th, and 3Th, and X$_3$ is any amino acid selected from: Gly, Ala, Ser, Val, Ile, Trp, Tyr, Nle, Ahp, Cpa, Cha, 2Th, 3Th, YMe, 2Np, and Bzt.

In some embodiments, a cyclic polypeptide of the invention having increased affinity to dimeric ubiquitin comprises or consists of the amino acid sequence: WGWFDDX$_1$YX$_2$X$_3$X$_4$AYCG (SEQ ID NO: 3), wherein X$_1$ is any amino acid selected from: Leu, Gln, Thr, Ans, His, Lys, Glu, Asp, and wherein X$_2$ is any amino acid selected from: Leu, Tyr, and Trp, and wherein X$_3$ is any amino acid selected from: Phe and Tyr, and wherein X$_4$ is any amino acid selected from: Val, Leu, and Tyr, and wherein X$_5$ is any amino acid selected from: Tyr, Ser, Ans, Pro, and His.

In some embodiments, a cyclic polypeptide of the invention having increased affinity to dimeric ubiquitin comprises or consists of the amino acid sequence: WLYLDDXGDW-WICG (SEQ ID NO: 4), wherein X is any amino acid selected from the group consisting of: Val, Leu, Asp, Glu, Asn, His, Trp, Tyr, Phe, Cys, Abu, Nva, Nle, Ahp, Aoc, hSM, tBu, Cpa, 2Th, 3Th, YMe, 2Np, Bzt, and DAl.

In some embodiments, a cyclic polypeptide of the invention having increased affinity to dimeric ubiquitin comprises or consists of the amino acid sequence: FQX$_1$WOX$_2$AX$_3$X$_4$X$_5$CG (SEQ ID NO: 5), wherein X$_1$ is an amino acid selected from: Tyr or Leu, X$_2$ is an amino acid selected from: Tyr or His, X$_3$ is an amino acid selected from: Thr or Ile, X$_4$ is an amino acid selected from: Gly or Ala, and X$_5$ is an amino acid selected from: Val or Leu.

In some embodiments, a cyclic polypeptide of the invention having increased affinity to tetrameric ubiquitin comprises or consists of the amino acid sequence WWYDXEYYYLGYGCG (SEQ ID NO: 1), wherein X is any amino acid selected from the group consisting of: Gly, Ala, Ser, Thr, Val, Leu, Ile, Asp, Glu, Asn, Gln, His, Trp, Tyr, Phe, Abu, Nva, Nle, Ahp, TMe, hSM, tBu, Cpa, Cha, Aib, MeG, MeA, MeB, MeF, 2Th, 3Th, YMe, and DAl In some embodiments, a cyclic polypeptide of the invention having increased affinity to tetrameric ubiquitin comprises or consists of the amino acid sequence: WGWFDNLYWYX$_1$X$_2$X$_3$CG (SEQ ID NO: 2), wherein X$_1$ is any amino acid selected from the group consisting of: Trp, Tyr, Phe, Nva, Nle, Ahp, tBu, Cpa, 2Th, 3Th, YMe, 2Np and Bzt, X$_2$ is any amino acid selected from the group consisting of: Gly, Ala, Thr, Val, Phe, Abu, Nva, MeG, and 3Th, and X$_3$ is any amino acid selected from the group consisting of: Ala, Ser, Val, Ile, Trp, Tyr, Phe, Nle, Ahp, tBu, Cpa, Cha, MeF, 2Th, 3Th, YMe, 2Np, and Bzt.

In some embodiments, a cyclic polypeptide of the invention having increased affinity to tetrameric ubiquitin comprises or consists of the amino acid sequence: WGWFDDX$_1$YX$_2$X$_3$X$_4$AYCG (SEQ ID NO: 3), wherein X$_1$ is any amino acid selected from: Leu, Gln, Thr, Ans, His, Lys, Glu, Asp, and wherein X$_2$ is any amino acid selected from: Leu, Tyr, and Trp, and wherein X$_3$ is any amino acid selected from: Phe and Tyr, and wherein X$_4$ is any amino acid selected from: Val, Leu, and Tyr, and wherein X$_5$ is any amino acid selected from: Tyr, Ser, Ans, Pro, and His.

In some embodiments, a cyclic polypeptide of the invention having increased affinity to tetrameric ubiquitin comprises or consists of the amino acid sequence: WLYLDDXGDWWICG (SEQ ID NO: 4), wherein X is any amino acid selected from the group consisting of: Ala, Leu, Asp, Glu, Asn, Gln, His, Trp, Tyr, Phe, Abu, Nva, Nle, Ahp, hSM, tBu, Cpa, Cha, 2Th, 3Th, YMe, 2Np, and Bzt.

In some embodiments, a cyclic polypeptide of the invention having increased affinity to tetrameric ubiquitin comprises or consists of the amino acid sequence: FQX$_1$WOX$_2$AX$_3$X$_4$X$_5$CG (SEQ ID NO: 5), wherein X$_1$ is an amino acid selected from: Tyr or Leu, X$_2$ is an amino acid selected from: Tyr or His, X$_3$ is an amino acid selected from: Thr or Ile, X$_4$ is an amino acid selected from: Gly or Ala, and X$_5$ is an amino acid selected from: Val or Leu.

In some embodiments, the cyclic polypeptide of the disclosed invention comprises not more than 16 amino acid residues. In some embodiments, not more than 16 amino acid residues comprises 8, 9, 10, 11, 12, 13, 14, or 15 amino acid residues, or any value and range therebetween. Each possibility represents a separate embodiment of the invention. In some embodiments, not more than 16 amino acid residues comprises 7-9, 8-11, 7-12, 10-13, 12-15, 8-14, 9-12, or 10-15 amino acid residues. Each possibility represents a separate embodiment of the invention.

In some embodiments, a polypeptide of the invention comprising or consisting of the amino acid sequence: FQYWOYATGVCG (SEQ ID NO: 35); and FQLWOHAIALCG (SEQ ID NO: 36), further comprises a methylated amino acid residue at position 6 or 8, or a combination thereof. In some embodiments, SEQ ID NO: 37 comprises a methylated Tyr, a methylated Thr, or both, at positions 6 or 8, respectively. In some embodiments, SEQ ID NO: 38 comprises a methylated His, a methylated Ile, or both, at positions 6 or 8, respectively.

In some embodiments, a polypeptide of the invention comprising or consisting of the amino acid sequence: FQYWOYATGVCG (SEQ ID NO: 35); and FQLWOHAIALCG (SEQ ID NO: 36), is further functionalized such as by conjugation of a carbon chain to an amino acid residue at position 6 or 8, or both. In some embodiments, a carbon chain comprises one or more carbons. In some embodiments, a carbon chain comprising one or more carbons comprises at least 2, at least 3, at least 4, or at least five carbons, or any value and range therebetween. Each possibility represents a separate embodiment of the invention. In some embodiments, a carbon chain comprising one or more carbons comprises 2-3, 2-4, 2-5, 3-4, 3-5, or 4-5 carbons. Each possibility represents a separate embodiment of the invention. In some embodiments, amino acid residues of a polypeptide of the invention as mentioned above are functionalized by conjugation to a methyl group, ethyl group, propyl group, butyl group, or any combination thereof.

In some embodiments, a polypeptide of the invention is capable of binding ubiquitin (Ub). In some embodiments, a polypeptide of the invention has specific binding affinity to ubiquitin (Ub). As defined herein, the term "Ubiquitin"

refers to the regulatory protein which is added to other proteins by means of post translational modification. In some embodiments, Ub is a polymeric Ub. In some embodiments, a polymeric Ub comprises at least 2, at least 3, at least 4, or at least 5 Ub monomers, or any value and range therebetween. Each possibility represents a separate embodiment of the invention. In some embodiments, a polymeric Ub comprises 2-3, 2-4, 2-5, 3-4, 3-5, or 4-5 Ub monomers. Each possibility represents a separate embodiment of the invention. In some embodiments, a Ub polymer comprises Ub monomers linked to one another at lysine (Lys) residue at position 11 (K11). In some embodiments, a Ub polymer comprises Ub monomers linked to one another at Lys residue at position 48 (K48). In some embodiments, a Ub polymer comprises Ub monomers linked to one another at Lys residue at position 63 (K63). In one embodiment, a Ub polymer comprises Ub monomers linked to one another at K11 and K48. In one embodiment, a Ub polymer comprises Ub monomers linked to one another at K11 and K63. In one embodiment, a Ub polymer comprises Ub monomers linked to one another at K48 and K63. In one embodiment, a Ub polymer comprises Ub monomers linked to one another at K11, K48 and K63. In some embodiments, a polypeptide of the invention has greater binding affinity to poly $^{K48}$Ub compared to poly $^{K11}$Ub or poly $^{K62}$Ub. In some embodiment, a Ub is further conjugated to a protein. In some embodiment, a protein is posttranslationally modified by conjugation to a Ub monomer or polymer. In some embodiments, a Ub-conjugated protein is bound by a polypeptide of the invention at the Ub site. In some embodiment, a polypeptide of the invention reduces deubiquitination of a Ub-conjugated protein. In some embodiments, a polypeptide of the invention increases proteasomal degradation of a Ub-conjugated protein.

In some embodiments, a polypeptide of the invention is capable of binding to Ub in vitro, in vivo, ex vivo, or any combination thereof. In some embodiments, a polypeptide of the invention is capable of penetrating a cell. In some embodiments, the polypeptide requires no additional elements to penetrate a cell. In some embodiments, the polypeptide may be further formulated with other elements for enhancing cell penetration. In some embodiments, the polypeptide may be used as a carrier or vehicle to carry other elements into a cell.

In some embodiments, the present invention is directed to a cyclic polypeptide of 12-16 amino acids, capable of penetrating a cell and binding to Ub with affinity $K_D$ of 0.1-100 mM.

In some embodiments, a polypeptide of the invention has increased affinity to Ub compared to control. In some embodiments, increased affinity is by at least 2-fold, at least 3-fold, at least 4-fold, at least 5-fold, at least 6-fold, at least 7-fold, at least 8-fold, at least 9-fold, or at least 10-fold greater compared to control, or any value and range therebetween. Each possibility represents a separate embodiment of the invention. In some embodiments, increased affinity is at least 5%, 10%, 20%, 35%, 50%, 65%, 75%, 85%, 90%, 99%, or 100% greater compared to control, or any value and range therebetween. Each possibility represents a separate embodiment of the invention. In some embodiments, increased affinity is by 1-5%, 4-10%, 8-20%, 25-35%, 30-50%, 45-65%, 60-75%, 70-85%, 80-90%, 85-99%, or 95-100% compared to control. Each possibility represents a separate embodiment of the invention.

As used herein, "control" encompasses any baseline to which the binding affinity of a polypeptide of the invention to Ub is compared to. In some embodiments, a control is a protein having no Ub binding affinity. In some embodiments, a control is a protein having low Ub binding affinity. In some embodiments, a control is a protein known to have Ub binding capabilities, such as ubiquitin receptors and proteins comprising ubiquitin binding domains, non-limiting examples of which include, but are not limited to: Rabex-5, STAM1, STAM2, IsoT, EAP45, S5a/Rpn10, Rpn13, or any other protein known in the art. In some embodiments, a control is a polypeptide of the invention in its linear form. In some embodiments, a control is a polypeptide of the invention which is initially inactivated, such as by antibody neutralization, enzymatic digestion, denaturation, or other methodologies known in the art of protein inactivation, prior to incubation in an environment comprising Ub, in vitro or in vivo.

In some embodiments, a polypeptide of the invention has Ub binding affinity with $K_D$ of 0.05-1 nM, 0.5-5 nM, 1-10 nM, 5-15 nM, 10-20 nM, 15-30 nM, 20-40 nM, 35-50 nM, 45-60 nM, 55-70 nM, 65-80 nM, 75-90 nM, 85-95 nM, 90-120 nM, 100-500 nM, 250-750 nM, 0.7-1.5 µM, 1-5 µM, 4-10 µM, 8-20 µM, or 15-40 µM. Each possibility represents a separate embodiment of the invention. In some embodiments, a polypeptide of the invention has Ub binding affinity with $K_D$ of 0.1 nM at most, 0.5 nM at most, 1 nM at most, 5 nM at most, 10 nM at most, 20 nM at most, 30 nM at most, 40 nM at most, 50 nM at most, 60 nM at most, 70 nM at most, 80 nM at most, 90 nM at most, 100 nM at most, 110 nM at most, 150 nM at most, 250 nM at most, 500 nM at most, 750 nM at most, 1,500 nM at most, 1 µM at most, 5 µM at most, 10 µM at most, 15 µM at most, 20 µM at most, or 30 µM at most, or any value and range therebetween. Each possibility represents a separate embodiment of the invention.

As exemplified herein below, a polypeptide of the invention comprising or consisting of the amino acid sequence selected from: *WWYDREYYYLGYGCG (SEQ ID NO: 14); *W̲GWFDN̲LYWYVTHCG (SEQ ID NO: 15); *W̲GWFDDLYLFVAYCG (SEQ ID NO: 16); *W̲LYLDDSGDWWICG (SEQ ID NO: 17); *F̲QYWOYATGVCG (SEQ ID NO: 37); and *F̲QLWOHAIALCG (SEQ ID NO: 38) has dimeric Ub binding affinity $K_D$ of: 30-50 nM, 20-40 nM. 85-115 nM, greater than 1 and greater than 900 nM, respectively, wherein asterisk (*) is a cyclizing molecule, wherein amino acid highlighted by an underline is a D-isomer amino acid, wherein amino acid highlighted by bold is a methylated amino acid, and wherein X is Ornithine.

As exemplified hereinbelow, a polypeptide of the invention comprising or consisting of the amino acid sequence selected from: *GWFDDLYLYVAYC (SEQ ID NO: 25); *GWFDDLYWYYAYC (SEQ ID NO: 29); *GWFDDEYWYYAYC (SEQ ID NO: 30); *GWFDDQYWYYAYC (SEQ ID NO: 31); *GWFDDNYWYYAYC (SEQ ID NO: 32); *GWFDDHYWYYAYC (SEQ ID NO: 33); *GWFDDKYWYYAYC (SEQ ID NO: 34), has dimeric and/or tetrameric Ub binding affinity $K_D$ of: 0.55-0.65 nM, 0.6-0.75 nM, 0.2-0.35 nM, 0.3-0.45 nM, 0.35-0.55 nM, 0.3-0.45 nM, and 0.25-0.4 nM, respectively, wherein asterisk (*) is a cyclizing molecule.

As exemplified herein below, a polypeptide of the has dimeric Ub binding affinity $K_D$ greater than 20 µM.

As exemplified herein below, a polypeptide of the invention comprising or consisting of the amino acid sequence selected from: *WWYDREYYYLGYGCG (SEQ ID NO: 14); *W̲GWFDN̲LYWYVTHCG (SEQ ID NO: 15); *W̲GWFDDLYLFVAYCG (SEQ ID NO: 16); *W̲LYLDDSGDWWICG (SEQ ID NO: 17); *

FQYWOYATGVCG (SEQ ID NO: 37); and *FQLWOHAIALCG (SEQ ID NO: 38) has tetrameric Ub binding affinity $K_D$ of: 10-20 nM, 15-25 nM, 20-35 nM, 1-10 nM, 6-10 nM, and 15-25 nM, respectively, wherein asterisk (*) is a cyclizing molecule, wherein amino acid highlighted by an underline is a D-isomer amino acid, wherein amino acid highlighted by bold is a methylated amino acid, and wherein 0 is Ornithine.

The present invention encompasses derivatives of the polypeptide of the invention. The term "derivative" or "chemical derivative" includes any chemical derivative of the polypeptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine (O) may be substituted for lysine.

In addition, a peptide derivative can differ from the natural sequence of the peptide of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic, or branched and the like, having any conformation, which can be achieved using methods known in the art.

As used herein, the terms "peptide", "polypeptide" and "protein" are used interchangeably, and refer to a polymer of amino acid residues.

The term "amino acid" as used herein means an organic compound containing both a basic amino group and an acidic carboxyl group. Included within this term are naturally occurring amino acids, modified, unusual, non-naturally occurring amino acids, as well as amino acids which are known to occur biologically in free or combined form but usually do not occur in proteins. Included within this term are modified and unusual amino acids, such as those disclosed in, for example, Roberts and Vellaccio (1983) The Peptides. 5: 342-429. Modified, unusual or non-naturally occurring amino acids include, but are not limited to, D-amino acids, hydroxylysine, 4-hydroxyproline, N-Cbz-protected aminovaleric acid (Nva), ornithine (O), aminooctanoic acid (Aoc), 2,4-diaminobutyric acid (Abu), homoarginine, norleucine (Nle), N-methylaminobutyric acid (MeB), 2-naphthylalanine (2Np), aminoheptanoic acid (Ahp), phenylglycine, (3-phenylproline, tert-leucine, 4-aminocyclohexylalanine (Cha), N-methyl-norleucine, 3,4-dehydroproline, N,N-dimethylaminoglycine, N-methylaminoglycine, 4-aminopipetdine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, cyano-propionic acid, 2-benzyl-5-amino-pentanoic acid, Norvaline (Nva), 4-O-methyl-threonine (TMe), 5-O-methyl-homoserine (hSM), tert-butyl-alanine (tBu), cyclopentyl-alanine (Cpa), 2-amino-isobutyric acid (Aib), N-methyl-glycine (MeG), N-methyl-alanine (MeA), N-methyl-phenylalanine (MeF), 2-thienyl-alanine (2Th), 3-thienyl-alanine (3Th), O-methyl-tyrosine (YMe), 3-Benzothienyl-alanine (Bzt) and D-alanine (DAl).

The term "amino acid residue" as used herein refers to the portion of an amino acid that is present in a peptide.

The term "peptide bond" means a covalent amide linkage formed by loss of a molecule of water between the carboxyl group of one amino acid and the amino group of a second amino acid.

The terms "peptide", "polypeptide" and "protein" as used herein encompass native peptides, peptidomimetics (typically including non-peptide bonds or other synthetic modifications) and the peptide analogs peptoids and semi-peptoids or any combination thereof. In another embodiment, the terms "peptide", "polypeptide" and "protein" apply to amino acid polymers in which at least one amino acid residue is an artificial chemical analog of a corresponding naturally occurring amino acid.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to an aspartic acid (D).

As used herein, the phrase "conservative substitution" also includes the use of a chemically derivatized residue in place of a non-derivatized residue provided that such peptide displays the requisite function as specified herein.

The peptide derivatives according to the principles of the present invention can also include side chain bond modifications, including but not limited to —CH2-NH—, —CH2-S—, —CH2-S=O, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O—O—C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The invention further includes peptides and derivatives thereof, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the function of disclosed chimera of the invention.

Polypeptide Synthesis

According to one embodiment, the polypeptide of the invention may be synthesized or prepared by any method and/or technique known in the art for peptide synthesis. According to another embodiment, the polypeptide may be synthesized by a solid phase peptide synthesis method of Merrifield (see J. Am. Chem. Soc, 85:2149, 1964). According to another embodiment, the polypeptide of the invention can be synthesized using standard solution methods, which are well known in the art (see, for example, Bodanszky, M., Principles of Peptide Synthesis, Springer-Verlag, 1984).

In general, the synthesis methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5 dimethoxybenzyloxycarbonyl, o-nitrophenylsulfenyl, 2-cyano-t-butyloxycarbonyl, 9-fluorenylmethyloxycarbonyl (Fmoc) and the like. In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

In another embodiment, a polypeptide of the invention may be synthesized such that one or more of the bonds, which link the amino acid residues of the peptide are non-peptide bonds. In another embodiment, the non-peptide bonds include, but are not limited to, imino, ester, hydrazide, semicarbazide, and azo bonds, which can be formed by reactions well known to one skilled in the art.

The term "linker" refers to a molecule or macromolecule serving to connect different moieties of a peptide or a polypeptide. In one embodiment, a linker may also facilitate other functions, including, but not limited to, preserving biological activity, maintaining sub-units and domains interactions, and others.

In some embodiments, a polypeptide of the invention may be attached or linked to another molecule via a chemical linker. Chemical linkers are well known in the art and include, but are not limited to, dicyclohexylcarbodiimide (DCC), N-hydroxysuccinimide (NETS), maleiimidobenzoyl-N-hydroxysuccinimide ester (MBS), N-ethyloxycarbonyl-2-ethyloxy-1,2-dihydroquinoline (EEDQ), N-isobutyloxy-carbonyl-2-isobutyloxy-1,2-dihydroquinoline (IIDQ). In another embodiment, linkers may also be monomeric entities such as a single amino acid. In another embodiment, amino acids with small side chains are especially preferred, or a small polypeptide chain, or polymeric entities of several amino acids. In another embodiment, a polypeptide linker is fifteen amino acids long or less, ten amino acids long or less, or five amino acids long or less. In one embodiment, a linker may be a nucleic acid encoding a small polypeptide chain. In another embodiment, a linker encodes a polypeptide linker of fifteen amino acids long or less, ten amino acids long or less, or five amino acids long or less.

Recombinant technology may be used to express the polypeptide of the invention, and is well known in the art. In another embodiment, the linker may be a cleavable linker, resulting in cleavage of the polypeptide of the invention once delivered to the tissue or cell of choice. In such an embodiment, the cell or tissue would have endogenous (either naturally occurring enzyme or be recombinantly engineered to express the enzyme) or have exogenous (e.g., by injection, absorption or the like) enzyme capable of cleaving the cleavable linker.

In another embodiment, the linker may be biodegradable such that the polypeptide of the invention is further processed by hydrolysis and/or enzymatic cleavage inside cells. In one embodiment, tumor specifically-expressed proteases, can be used in the delivery of prodrugs of cytotoxic agents, with the linker being selective for a site-specific proteolysis. In some embodiments, a readily-cleavable group include acetyl, trimethylacetyl, butanoyl, methyl succinoyl, t-butyl succinoyl, ethoxycarbonyl, methoxycarbonyl, benzoyl, 3-aminocyclohexylidenyl, and the like.

The invention further encompasses a polynucleotide sequence comprising a nucleic acid encoding any of the polypeptides of the invention. In another embodiment, the nucleic acid sequence encoding the polypeptide is at least 70%, or alternatively at least 80%, or alternatively at least 90%, or alternatively at least 95%, or alternatively at least 99% homologous to the nucleic acid sequence encoding the nucleic acid sequence of the polypeptides of the invention or a derivative thereof, or any value and range therebetween. Each possibility represents a separate embodiment of the invention.

In some embodiment, the invention provides a polynucleotide encoding the polypeptide of the invention.

In some embodiments, a polynucleotide molecule of the invention encodes a polypeptide comprising non-canonical amino acids.

In some embodiments, the polynucleotide of the invention is ligated into an expression vector, comprising a transcriptional control of a cis-regulatory sequence (e.g., promoter sequence). In some embodiments, the cis-regulatory sequence is suitable for directing constitutive expression of the polypeptide of the invention. In some embodiments, the cis-regulatory sequence is suitable for directing tissue-specific expression of the polypeptide of the invention. In some embodiments, the cis-regulatory sequence is suitable for directing inducible expression of the polypeptide of the invention.

The term "polynucleotide" refers to a nucleic acid (e.g., DNA or RNA) sequence that comprises coding sequences necessary for the production of a polypeptide. In one embodiment, a polynucleotide refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, "genomic polynucleotide sequence" refers to a sequence derived (or isolated) from a chromosome and, thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the invention, as well as some intronic sequences interposing therebetween. In one embodiment, the intronic sequences can be of any source, including of other genes, and typically may include conserved splicing signal sequences. In one embodiment, intronic sequences include cis-acting expression regulatory elements.

In some embodiments, a polynucleotide of the invention is prepared using PCR techniques, or any other method or procedure known to one of ordinary skill in the art.

In one embodiment, a polynucleotide of the invention is inserted into expression vectors (i.e., a nucleic acid construct) to enable expression of a recombinant polypeptide. In one embodiment, the expression vector includes additional sequences which render this vector suitable for replication and integration in prokaryotes. In one embodiment, the expression vector includes additional sequences which render this vector suitable for replication and integration in eukaryotes. In one embodiment, the expression vector includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptide of the invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems) to express the polypeptide of the invention. In one embodiment, the expression vector is used to express the polynucleotide of the invention in mammalian cells.

In some embodiments, in bacterial systems, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector may further include additional polynucleotide sequences that allow, for example, the translation of several proteins from a single mRNA such as an internal ribosome entry site (IRES).

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses can be used. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression of the polypeptide of the invention. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, the viral vectors that are produced are unable to spread laterally. In one embodiment, this characteristic can be useful if the desired purpose is to introduce a specified gene into only a localized number of targeted cells.

Various methods can be used to introduce an expression vector into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct can also include sequences engineered to optimize stability, production, purification, yield or activity of the expressed polypeptide.

In some embodiments, transformed cells are cultured under effective conditions, which allow for the expression of high amounts of a recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce a recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, the cells can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptide of the invention either remains within the recombinant cell, secreted into the fermentation medium, secreted into a space between two cellular membranes, such as the periplasmic space in E. coli; or retained on the outer surface of a cell or viral membrane. In one embodiment, following a predetermined time in culture, recovery of the recombinant polypeptide is affected.

In one embodiment, the phrase "recovering the recombinant polypeptide" as used herein, refers to collecting the whole fermentation medium containing the polypeptide and need not imply additional steps of separation or purification.

In one embodiment, a polypeptide of the invention is purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety, and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the invention is retrieved in "substantially pure" form that allows for the effective use of the protein in the applications described herein.

As used herein, the term "substantially pure" describes a peptide/polypeptide or other material which has been separated from its native contaminants. Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure, or any value and range therebetween. Each possibility represents a separate embodiment of the invention. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

In one embodiment, the polypeptide of the invention is substantially free of naturally-associated host cell components. The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

In one embodiment, the polypeptide of the invention can also be synthesized using in vitro expression systems. In one embodiment, in vitro synthesis methods are well known in the art and the components of the system are commercially available. Non-limited example for in vitro system includes, but is not limited to in vitro translation, such as exemplified herein below.

In some embodiments, the polypeptide of the invention is cyclized. In some embodiments, the first amino acid residue of the N terminus of a polypeptide of the invention is conjugated to a cyclizing molecule. In some embodiments, the first amino acid residue of the polypeptide (positioned at the N terminus) and another amino residue of the polypeptide (positioned at the C terminus) are bound to one another, thereby resulting in a cyclic polypeptide. In some embodiments, the cyclizing molecule is bound to both the first amino acid residue and to another amino acid residue located at the C terminus. In some embodiments, the cyclizing molecule facilitates the binding of the first and the C terminal amino acid residue. In some embodiments, the cyclizing molecule is released upon binding of the first and the C terminal amino acid residue. In some embodiments, the cyclizing molecule is conjugated to both the first and the C terminal amino acid residue upon binding. As defined herein, a "C terminal amino acid residue" refers to an amino acid residue located in a position closer to the C terminal end of a linear polypeptide compared to the N terminal end of the polypeptide. In some embodiments, a C terminal amino acid residue is positioned 8 before last, 7 before last, 6 before last, 5 before last, 4 before last, 3 before last, 2 before last, 1 before last, or is the last amino acid residue in a linear polypeptide. Each possibility represents a separate embodiment of the invention. According to a non-limiting example, an amino acid residue at position 9 of a polypeptide comprising 16 amino acid residues is considered as a C terminal amino acid residue. A variety of methods are available for cyclizing a polypeptide (e.g., macrocyclization) as reviewed, for example by White and Yudin (2011).

In some embodiments, a cyclizing molecule comprises one or more halogen atoms selected from the group consisting of: Fluoride (F), Chlorine (Cl), Bromide (Br), Iodine (I) and Astatine (At), or any combination thereof. Non-limiting examples for a cyclizing molecule comprising a halogen include, but are not limited to: chloracetyl chloride, 3-chlorobenzoyl (3-ClBz), 4-chlorobenzoyl (4-ClBz) or $Cl_2SAc$. In one embodiment, a cyclizing molecule comprising a halogen group is conjugated to the first amino acid residue of a polypeptide's N terminus and nucleophilicaly attacks a thiol group of a cysteine residue located at the C terminal end of the polypeptide, thereby resulting in a cyclic polypeptide.

Compositions

In some embodiments, the present invention is directed to a composition comprising a polypeptide comprising or consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or any combination thereof.

According to another embodiment, the invention provides a pharmaceutical composition comprising as an active ingredient the polypeptide of the present invention, and pharmaceutically acceptable carrier and/or diluents. In some embodiments, the pharmaceutical composition facilitates administration of a compound to an organism. According to another embodiment, the invention provides a pharmaceutical composition comprising as an active ingredient a therapeutically effective amount of the polypeptide of the invention.

In another embodiment, the pharmaceutical composition of the invention may be formulated in the form of a pharmaceutically acceptable salt of the polypeptides of the present invention or their analogs, or derivatives thereof. In another embodiment, pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned. The carrier may comprise, in total, from about 0.1% to about 99.99999% by weight of the pharmaceutical compositions presented herein.

As used herein, the term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the polypeptide of the invention, preferably in a substantially purified form, together with a suitable amount of carrier so as to provide the form for proper administration to the subject.

According to an embodiment of the invention, pharmaceutical compositions contain 0.1-95% of the polypeptide(s) of the invention, derivatives, or analogs thereof. According to another embodiment of the invention, pharmaceutical compositions contain 1-70% of the polypeptide(s). According to another embodiment of the invention, the composition or formulation to be administered may contain a quantity of polypeptide(s), according to embodiments of the invention in an amount effective to treat the condition or disease of the subject being treated.

An embodiment of the invention relates to a polypeptide of the invention, presented in unit dosage form and prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

According to one embodiment, the compositions of the invention are administered in the form of a pharmaceutical composition comprising at least one of the active components of this invention (the cyclic polypeptide) together with a pharmaceutically acceptable carrier or diluent. In another embodiment, the compositions of this invention can be administered either individually or together in any conventional oral, parenteral or transdermal dosage form. In some embodiments, the pharmaceutical composition further comprises at least one anticancer agent such as a chemotherapeutic agent. In some embodiments, the pharmaceutical composition is adopted for combined administration with an anticancer therapy such as chemotherapy, radiotherapy, immunotherapy, hormonal therapy, toxin therapy or surgery.

As used herein, the terms "administering", "administration", and like terms refer to any method which, in sound medical practice, delivers a composition containing an active agent to a subject in such a manner as to provide a therapeutic effect.

Depending on the location of the tissue of interest, the polypeptide of the invention can be administered in any manner suitable for the provision of the polypeptides to cells within the tissue of interest. Thus, for example, a composition containing the polypeptide of the invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In some embodiments, the pharmaceutical compositions comprising the polypeptide are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a polypeptide of the invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

According to some embodiments, the polypeptide of the invention, can be delivered in a controlled release system. In another embodiment, an infusion pump can be used to administer the peptide such as the one that is used, for example, for delivering insulin or chemotherapy to specific organs or tumors. In another embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

The presently described peptide, may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The compositions also include incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, it will be appreciated that the polypeptide of the invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is affected or diminution of the disease state is achieved.

In some embodiments, the polypeptide is administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the polypeptide is the amount of the polypeptide necessary for the in vivo measurable expected biological effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

Pharmaceutical compositions containing the presently described polypeptide as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

In one embodiment, compositions including the preparation of the present invention formulated in a compatible pharmaceutical carrier are prepared, placed in an appropriate container, and labeled for treatment of an indicated condition.

In one embodiment, compositions of the invention are presented in a pack or dispenser device, such as an FDA approved kit, which contains, one or more unit dosages forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Methods of Use

In some embodiments, there is provided a method for reducing deubiquitination activity of a cell, comprising contacting the cell with a cyclic polypeptide having a ubiquitin binding affinity $K_D$ of 0.05-100 nM, wherein the cyclic polypeptide comprises not more than 16 amino acid residues, and wherein at least 55% of amino acids of the cyclic polypeptide are selected from: W, G, F, D, L, Y, and C.

In some embodiments, there is provided a method for inducing or increasing apoptosis rate of a cell, comprising contacting the cell with a cyclic polypeptide having a ubiquitin binding affinity $K_D$ of 0.05-100 nM, wherein the cyclic polypeptide comprises not more than 16 amino acid residues, and wherein at least 55% of amino acids of the cyclic polypeptide are selected from: W, G, F, D, L, Y, and C. in some embodiments, the cell is a cancerous cell.

In some embodiments, there is provided a method for ameliorating or treating cancer or pre-malignancy in a subject in need thereof, comprising administering to the subject a therapeutically effective amount of a cyclic polypeptide, wherein the polypeptide binds ubiquitin with an affinity $K_D$ of 0.05-100 nM, wherein the cyclic polypeptide comprises not more than 16 amino acid residues, and wherein at least 55% of amino acids of the cyclic polypeptide are selected from: W, G, F, D, L, Y, and C.

In some embodiments, a cyclic polypeptide capable of binding ubiquitin with an affinity $K_D$ of 0.05-100 nM, which comprises not more than 16 amino acid residues, and at least 55% of amino acids of which are selected from: W, G, F, D, L, Y, and C, is selected from: WYDX$_1$EYYYLGYGC (SEQ ID NO: 1); GWFDNLYWYVX$_1$X$_1$C (SEQ ID NO: 2); GWFDDX$_2$YX$_3$X$_4$X$_5$AYC (SEQ ID NO: 3); LYLDDX$_1$GDWWIC (SEQ ID NO: 4); and FQX$_6$WOX$_7$AX$_8$X$_9$X$_{10}$CG (SEQ ID NO: 5).

In some embodiments, at least 55%, at least 60%, at least 65%, at least 70%, at least 80%, or at least 90%, of amino acids of the cyclic polypeptide are selected from: W, G, F, D, L, Y, and C, or any range and value therebetween. Each possibility represents a separate embodiment of the invention. In some embodiments, 50-65%, 60-75%, 70-85%, or 80-100%, of amino acids of the cyclic polypeptide are selected from: W, G, F, D, L, Y, and C. Each possibility represents a separate embodiment of the invention.

In some embodiments, a cyclic polypeptide as disclosed herein, comprises at least one amino acid of each type selected from: W, G, F, D, L, Y, and C.

In some embodiments, a cyclic polypeptide as discloses herein, comprises one or more W amino acid residues. In some embodiments, a cyclic polypeptide as discloses herein, comprises one or more G amino acid residues. In some embodiments, a cyclic polypeptide as discloses herein, comprises one or more C amino acid residues. In some embodiments, a cyclic polypeptide as discloses herein, comprises W and G amino acid residues. In some embodiments, a cyclic polypeptide as discloses herein, comprises W and C amino acid residues. In some embodiments, a cyclic polypeptide as discloses herein, comprises G and C amino acid residues. In some embodiments, a cyclic polypeptide as discloses herein, comprises W, G, and C amino acid residues. In some embodiments, a cyclic polypeptide as discloses herein, comprises W, G, and C amino acid residues and one or more amino acid residues selected from: F, D, L, and Y.

In some embodiments, there present invention is directed to a method for treating, ameliorating, reducing and/or preventing a condition associated with increased deubiquitination activity of a cell in a subject in need thereof, the method comprising the step of: administering to the subject a pharmaceutical composition comprising a therapeutically effective amount of a cyclic polypeptide having ubiquitin binding affinity $K_D$ of 0.1-100 nM, thereby treating, ameliorating, reducing and/or preventing a condition associated with increased deubiquitination activity of a cell in the subject in need thereof.

In some embodiments, there present invention is directed to a method for treating, ameliorating, reducing and/or preventing a condition associated with increased proliferation activity of a cell in a subject in need thereof, the method comprising the step of: administering to the subject a pharmaceutical composition comprising a therapeutically effective amount of a cyclic polypeptide having ubiquitin binding affinity $K_D$ of 0.1-100 nM, thereby treating, ameliorating, reducing and/or preventing a condition associated with increased deubiquitination activity of a cell in the subject in need thereof.

In some embodiments, there present invention is directed to a method for treating, ameliorating, reducing and/or preventing a condition associated with increased apoptosis-resistance activity of a cell in a subject in need thereof, the method comprising the step of: administering to the subject a pharmaceutical composition comprising a therapeutically effective amount of a cyclic polypeptide having ubiquitin binding affinity $K_D$ of 0.1-100 nM, thereby treating, ameliorating, reducing and/or preventing a condition associated with increased deubiquitination activity of a cell in the subject in need thereof.

In some embodiments, the condition associated with: increased deubiquitination activity of a cell, increased proliferation activity of a cell, increased apoptosis-resistance activity of a cell, or any combination thereof, comprises cancer.

In some embodiments, a method for treating or ameliorating a cancer in a subject in need thereof according to the present invention, comprises administering to the subject any one of:

(i) the polypeptide of the invention; or (ii) the pharmaceutical composition of the invention, thereby treating or ameliorating cancer in the subject.

In some embodiments, the present invention is directed to a method for treating cancer or pre-malignancy condition in a subject in need thereof, the method comprising the step of administering to the subject a pharmaceutical composition comprising a therapeutically effective amount of one or more amino acid molecules, each comprising or consisting of an amino acid sequence selected from the group consisting of SEQ ID Nos.: 1-38 and a pharmaceutical acceptable carrier, thereby treating or ameliorating cancer or pre-malignancy condition in the subject in need thereof. In some embodiments, the subject is further treated with an additional anticancer therapy such as chemotherapy, radiotherapy, immunotherapy, hormonal therapy, toxin therapy or surgery.

In another embodiment, the polypeptide of the invention or a composition comprising the thereof is for use in treatment, amelioration, reduction, and/or prevention of cancer or pre-malignancy condition in a subject in need thereof. In some embodiments, the composition comprises an effective amount of a polypeptide for use in the treatment or prevention of cancer or pre-malignancy condition in a subject in need thereof. In some embodiments, a composition comprises a therapeutically effective amount of one or more amino acid molecules, each comprising or consisting of an amino acid sequence selected from SEQ ID Nos.: 1-38, is for use in the treatment or prevention of cancer or pre-malignancy condition in the subject in need thereof. In some embodiments, the composition further comprises at least one anticancer agent such as a chemotherapeutic agent. In some embodiments, the composition is adopted for use in combination with an anticancer therapy such as chemotherapy, radiotherapy, immunotherapy, hormonal therapy, toxin therapy or surgery.

In some embodiments, a composition of the invention comprises an effective amount of the polypeptide in the preparation of a medicament for the treatment, amelioration, reduction, or prevention of a disease associated with increased cell proliferation, deubiquitination activity, apoptosis-resistance activity, or a combination thereof, in a subject in need thereof. In some embodiments, the invention is directed to a use of a composition comprising an effective amount of one or more amino acid molecules, each comprising or consisting of an amino acid sequence selected from SEQ ID Nos.: 1-38 in the preparation of a medicament for the treatment of a disease associated with increased cell proliferation, deubiquitination activity, or a combination thereof, in a subject in need thereof.

In one embodiment, the polypeptide of the invention is provided to the subject per se. In one embodiment, one or more of the polypeptides of the invention are provided to the subject per se. In one embodiment, the polypeptide of the invention is provided to the subject as part of a pharmaceutical composition where it is mixed with a pharmaceutically acceptable carrier. In one embodiment, one or more of the polypeptides of the invention are provided to the subject as part of a pharmaceutical composition where they are mixed with a pharmaceutically acceptable carrier.

In some embodiments, the disease associated with increased cell deubiquitination activity, increased cell proliferation activity, increased apoptosis-resistance activity, or a combination thereof, is cancer.

As used herein the terms "cancer" or "pre-malignancy" refer to diseases associated with cell proliferation. Non-limiting types of cancer include carcinoma, sarcoma, lymphoma, leukemia, blastoma and germ cells tumors. In one embodiment, carcinoma refers to tumors derived from epithelial cells including but not limited to breast cancer, prostate cancer, lung cancer, pancreas cancer, and colon cancer. In one embodiment, sarcoma refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to Hodgkin lymphoma, non-Hodgkin lymphoma, multiple myeloma and immunoproliferative diseases. In one embodiment, leukemia refers to tumors derived from hematopoietic cells that leave the bone marrow and tend to mature in the blood including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme. In one embodiment, germ cell tumors refer to tumors derived from germ cells including but not limited to germinomatous or seminomatous germ cell tumors (GGCT, SGCT) and nongerminomatous or nonseminomatous germ cell tumors (NGGCT, NSGCT). In one embodiment, germinomatous or seminomatous tumors include but not limited to germinoma, dysgerminoma and seminoma. In one embodiment, nongerminomatous or non-seminomatous tumors refers to pure and mixed germ cells tumors including but not limited to embryonal carcinoma, endodermal sinus tumor, choriocarcinoma, tearoom, polyembryoma, gonadoblastoma and teratocarcinoma.

As used herein, "cancer or pre-malignant cell proliferation" is a molecular process which further to increased cell proliferation rates requires increased deubiquitination activity. In some embodiments, the method of the present invention is directed to reducing deubiquitination activity. In some embodiments, reducing deubiquitination activity results in increased proteasomal activity. In some embodiments, reducing deubiquitination activity results in increased protein degradation. In some embodiments, reducing deubiquitination activity further reduces drug resistance. In some embodiments, a cancerous cell has increased deubiquitination activity compared to a non-cancerous cell or a benign cell. In another embodiment, reducing deubiquitination activity reduces viability of a cancerous cell. In some embodiments, reducing deubiquitination activity increases apoptosis rates in or of a cancerous cell. In some embodiments, increasing cell apoptosis results in reduced cell viability.

In some embodiments, the terms "reduce" or "reducing" used in the abovementioned embodiments (such as for deubiquitination activity of a cell, proteasomal degradation of ubiquitinated proteins, cell viability, or others), are by at least 10%, by at least 20%, by at least 30%, by at least 40%, by at least 50%, by at least 60%, by at least 70%, by at least 80%, by at least 90%, or by at least 100% compared to control, or any value and range therebetween. Each possibility represents a separate embodiment of the invention. In some embodiments, reducing is by 1-5%, 4-10%, 8-20%, 15-30%, 25-40%, 35-55%, 50-70%, 60-80%, 75-90%, 90-99%, or 95-100% compared to control. Each possibility represents a separate embodiment of the invention. In some embodiments, reducing is by at least 2-fold, by at least 3-fold, by at least 5-fold, by at least 10-fold, by at least 15-fold, by at least 20-fold, by at least 40-fold, by at least 75-fold, by at least 100-fold, by at least 150-fold, by at least 200-fold, by at least 500-fold, or by at least 1,000-fold compared to control, or any value and range therebetween. Each possibility represents a separate embodiment of the invention.

The terms "inhibiting", "reducing" and "decreasing" are interchangeable.

In some embodiments, the term "increase" or "increasing" used in the abovementioned embodiments (such as for pro-apoptotic activity, cell apoptosis rate, or others), is by at least 10%, by at least 20%, by at least 30%, by at least 40%, by at least 50%, by at least 60%, by at least 70%, by at least 80%, by at least 90%, or by at least 100% compared to control, or any value and range therebetween. Each possibility represents a separate embodiment of the invention. In some embodiments, increasing is by 1-5%, 4-10%, 8-20%, 15-30%, 25-40%, 35-55%, 50-70%, 60-80%, 75-90%, 90-99%, or 95-100% compared to control. Each possibility represents a separate embodiment of the invention. In some embodiments, increasing is by at least 2-fold, by at least 3-fold, by at least 5-fold, by at least 10-fold, by at least 15-fold, by at least 20-fold, by at least 40-fold, by at least 75-fold, by at least 100-fold, by at least 150-fold, by at least 200-fold, by at least 500-fold, or by at least 1,000-fold compared to control, or any value and range therebetween. Each possibility represents a separate embodiment of the invention.

In some embodiments, a polypeptide of the invention reduces cell viability with a half maximal inhibitory concentration (IC$_{50}$) of 0.01-1 nM, 0.05-2 nM, 1-5 nM, 4-10 nM, 5-50 nM, 10-100 nM, 50-250 nM, 200-750 nM, 0.5-1.5 µM, 1-3 µM, 2-4 µM, 3-6 µM, 4-7 µM, 5-8 µM, 6-9 µM, 8-12 µM, 10-13 µM, 12-14 µM, 11-15 µM, 13-17 µM, 16-19 µM, 15-20 µM, 14-22 µM, 20-25 µM, or 26-35 µM. Each possibility represents a separate embodiment of the invention.

In some embodiments, ubiquitination/deubiquitination kinetics or dynamics, are detected by any assay known to in the art, including immune-assays, western-blot, immune-histochemistry, and the like, such as for detecting $^{K48}$Ub. In some embodiments, protein degradation and proteasomal activity are detected by any acceptable method, including immune-assays, western-blot, immune-histochemistry, pulse-chase assay, and the like, all of which are well known to one of ordinary skill in the art.

The term "subject" as used herein refers to an animal, more particularly to non-human mammals and human organism. Non-human animal subjects may also include prenatal forms of animals, such as, e.g., embryos or fetuses. Non-limiting examples of non-human animals include: horse, cow, camel, goat, sheep, dog, cat, non-human primate, mouse, rat, rabbit, hamster, guinea pig, pig. In one embodiment, the subject is a human. Human subjects may also include fetuses. In one embodiment, a subject in need thereof is a subject afflicted with and/or at risk of being afflicted with a condition associated with increased cell proliferation, deubiquitination activity, or combination thereof.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described peptides prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder, but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

As used herein, the terms "subject" or "individual" or "animal" or "patient" or "mammal," refers to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include", and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Preparation of eFx

All oligonucleotides were purchased from Operon (Japan). The DNA template for the flexizyme eFx (DNA_eFx, below) was assembled by primer extension and PCR. The DNA template was transcribed by T7 RNA polymerase and purified using 12% denaturing poly acrylamide gel electrophoresis (PAGE). The RNA product (RNA_eFx) was dissolved in water, adjusted to 250 µM and stored at −80° C.

DNA_eFx (SEQ ID NO: 39)
GGCGTAATACGACTCACTATAGGATCGAAAGATTTCCGCGGCCCCGAAAG

GGGATTAGCGTTAGGT

RNA_eFx (SEQ ID NO: 40)
GGAUCGAAAGAUUUCCGCGGCCCCGAAAGGGGAUUAGCGUUAGGU

Preparation of tRNA$^{fMet}_{CAU}$

The DNA template for tRNA$^{fMet}_{CAU}$ (DNA_tRNA, below) was assembled by primer extension and PCR. The DNA template was transcribed by T7 RNA polymerase and purified using 8% denaturing PAGE, the RNA product (RNA_tRNA) was dissolved in water and the concentration adjusted to 250 µM and stored at −80° C.

DNA_tRNA (SEQ ID NO: 41)
GGCGTAATACGACTCACTATAGGCGGGGTGGAGCAGCCTGGTAGCTCGTC

GGGCTCATAACCCGAAGATCGTCGGTTCAAATCCGGCCCCCGCAACCA

RNA_tRNA (SEQ ID NO: 42)
GGCGGGGUGGAGCAGCCUGGUAGCUCGUCGGGCUCAUAACCCGAAGAUCG

UCGGUUCAAAUCCGGCCCCCGCAACCA

Aminoacylation of tRNA$^{fMet}_{CAU}$ with ClAc-D-Trp-CME

Initiator tRNA$^{fMet}_{CAU}$ was aminoacylated with the non-canonical amino acid N-ClAc D-Trp following protocols as described previously (Goto et al., 2011). Twenty-five (25) µM tRNA$^{fMet}_{CAU}$, 25 µM eFx and 5 mM ClAc D-Trp-CME were incubated in 50 mM HEPES-KOH pH 8.4, 600 mM MgCl$_2$ in 20% DMSO for 2 hours at 0° C. The reaction was stopped by adding 4 reaction volumes of 0.3 M NaOAc pH 5.2, and the product precipitated using 10 reaction volumes of EtOH. The ClAc-D-Trp-tRNA$^{fMet}_{CAU}$ pellet was washed twice with 0.1 M NaOAc pH 5.2 70% EtOH, once with 70% EtOH, dried and stored at −80° C.

Reprogrammed In Vitro Translation System

A custom in vitro translation mixture was assembled, with each protein/RNA component purified separately from E. coli. Final concentrations: 1.2 µM ribosome, 0.1 µM T7 RNA polymerase, 4 µg/mL creatine kinase, 3 µg/mL myokinase, 0.1 µM pyrophosphatase, 0.1 µM nucleotide-diphosphatase kinase, 2.7 µM IF1, 0.4 µM IF2, 1.5 µM IF3, 30 µM EF-Tu, 30 µM EF-Ts, 0.26 µM EF-G, 0.25 µM RF2, 0.17 µM RF3, 0.5 µM RRF, 0.6 µM MTF, 0.73 µM AlaRS, 0.03 µM ArgRS, 0.38 µM AsnRS, 0.02 µM CysRS, 0.06 µM GlnRS, 0.23 µM GluRS, 0.09 µM GlyRS, 0.02 µM HisRS, 0.4 µM IleRS, 0.04 µM LeuRS, 0.03 µM MetRS, 0.68 µM PheRS, 0.16 µM ProRS, 0.04 µM SerRS, 0.09 µM ThrRS, 0.03 µM TrpRS, 0.02 µM ValRS, 0.13 µM AspRS, 0.11 µM LysRS, 0.02 µM TyrRS. Additionally, 50 mM HEPES-KOH (pH 7.6), 100 mM Potassium Acetate, 2 mM GTP, 2 mM ATP, 1 mM CTP, 1 mM UTP, 20 mM Creatine Phosphate, 12 mM Mg(OAc)$_2$, 2 mM spermidine, 2 mM DTT, and 1.5 mg/mL E. coli total tRNA (Roche). Nineteen (19) out of the 20 canonical amino acids were included at 500 methionine was not added nor the formyl donor, usually 10-formyl-5,6,7,8-tetrahydrofolic acid, required for initiation using formyl methionine. The translation reaction was supplemented with 50 µM ClAc-D-Trp-tRNA$^{fMet}_{CAU}$.

mRNA Library Preparation

The DNA template for mRNA with 6-12 randomized codons (DNA_NNK, below) were assembled by primer extension and PCR. The DNA template was transcribed by T7 RNA polymerase and purified using 8% denaturing PAGE, the mRNA products were dissolved in water and stored at −80° C. mRNA with NNK lengths of 6, 7, 8, 9, 10, 11, 12 were mixed in a ratio of 0.0004:0.01:0.1:1:1:1:1 to avoid oversampling the smaller NNK sequences, with the aim of having a greater number of unique sequences in the final mRNA library. The mRNA library was ligated with puromycin linker (5'-Phosphate-CTCCCGCCCCCCGTCC-(SPC18)$_5$-CC-puromycin-3') (SEQ ID NO: 43) by T4 RNA ligase. The ligated product was purified by phenol-chloroform extraction and ethanol precipitation.

DNA_NNK (SEQ ID NO: 44)
TAATACGACTCACTATAGGGTTAACTTTAAGAAGGAGATATACATATG (NNK)$_{6-12}$TGCGGCAGCGGCAGCGGCAGCTAGGACGGGGGCGGAAA
N = equal C:G:A:T, K = equal G:T Reconstitution of Biotin-Ub$_n$ Lyophilized biotin-Ub$_n$, after solid phase peptide synthesis (SPPS) and purification, were resuspended in 6 M Urea, followed by diluted ×200 in 50 mM HEPES pH 7.3, 150 mM NaCl. Any precipitate was removed by centrifugation at 13,000 g for 30 mins. Final concentration of soluble protein was measured using Qubit Protein Assay Kit (ThermoFisher), identity confirmed using MALDI-TOF (Broker) and flash frozen N2(l) before storage at −80° C.

Binding of Biotin-Ub$_n$ Polymers to Streptavidin Magnetic Beads

Various volumes of Dynabeads M280 Streptavidin (ThermoFisher) 10 mg/mL bead slurry were washed with selection buffer (50 mM HEPES pH 7.3, 150 mM NaCl, 0.05% Tween20, 2 mM DTT) before removal of the buffer and addition of 10 μL of 1 biotinylated protein, and incubated for 15 mins at 4° C. Free biotin was added to a concentration 25 μM and incubated for an additional 15 mins at 4° C. Supernatant and washed beads were run on denaturing on Tricine-SDS-PAGE for biotin-Ub$_1$ and biotin-$^{K48}$Ub$_2$, 10% Tris-SDS-PAGE for biotin-$^{K48}$Ub$_4$ and stained using SYPRO Ruby Protein Gel Stain (ThermoFisher). Binding capacities were 3 pmol/μL slurry for biotin-Ub$_1$ and 2 pmol/μL slurry for biotin-Ub$_2$ and biotin-Ub$_4$.

First Round of Selection to Find Ub$_{2,4}$ Binding Peptides

The two initial cyclic peptide libraries (one each for $^{K48}$Ub$_2$ and $^{K48}$Ub$_4$) were formed by adding puromycin ligated mRNA library (150 pmol) to a 150 μL scale reprogrammed in vitro translation system and incubated at 37° C. for 30 mins. This was cooled to 25° C. for 12 mins to promote mRNA-puromycin ligation to the translated peptides. To this solution 15 μL of 200 mM EDTA (pH 8.0) was added and incubated at 37° C. to dissociate the ribosome from the mRNA-puromycin-peptide products and promote cyclization of the peptides. A hundred and sixty-five (165) μL×2 blocking solution (100 mM HEPES pH 7.3, 300 mM NaCl, 0.1% Tween20, 0.2% acetylated BSA, 4 mM DTT) were added, and the resulting solution was added to magnetic beads loaded with either biotin-Ub$_2$ or biotin-Ub$_4$. Beads amount was calculated to meet a final concentration of Ub$_n$ in the suspension of 200 nM. Bead suspensions were incubated with rotation for 30 mins at 4° C. Beads were quickly washed ×3 with ice-cold selection buffer (50 mM HEPES pH 7.3, 150 mM NaCl, 0.05% Tween20, 2 mM DTT). The bead-bound mRNAs were then reverse transcribed using MMLV-RTase H(−) (Promega) for 1 hour at 42° C. using a DNA primer matching the 3' end of the mRNA. The suspensions were diluted in PCR buffer, heated to 95° C. and the DNA-containing supernatant was collected. Quantitative PCR (qPCR) was used to quantify the amount of recovered DNA. This DNA was PCR amplified using taq polymerase and transcribed overnight using T7 polymerase to make mRNA, acidic phenol chloroform-extracted and isopropanol-precipitated, ligated to puromycin (as above), extracted and ethanol precipitated for use in subsequent rounds.

Subsequent Rounds of Selection, Including Negative Selection to Ub$_1$

Ligated mRNA from a previous round (5 μmol) was added to a 5 μL scale reprogrammed in vitro translation system. This was incubated at 37° C. 30 mins, 25° C. for 12 mins, then 1 μL 100 mM EDTA (pH 8.0) added and 30 mins at 37° C. mRNA was then reverse transcribed with MMLV-RTase H(−) to form mRNA-DNA duplexes. ×2 blocking solution was added, and this solution added to magnetic beads loaded with biotin-Ub$_1$, with sufficient beads for 200 nM or 2 μM Ub$_1$ in the suspension. After incubation at 4° C. for 30 mins with rotation, and supernatant was removed this incubation constitutes a "negative selection". Two further negative selections were carried out using fresh Ub$_1$ loaded beads. The supernatant was then added to beads loaded with either biotin-Ub$_2$ or biotin-Ub$_4$, incubated at 4° C. for 30 mins, and the supernatant discarded a "positive selection". The beads were then washed ×3 with ice-cold selection buffer. PCR buffer added to the beads and DNA recovered by heating to 95° C. and collecting the supernatant. As for the first round, DNA was quantified using qPCR, amplified using PCR, transcribed and ligated to puromycin. An increase in % recovered DNA was calculated at each round in all selections.

Deep Sequencing of Recovered Enriched DNA Libraries

DNA recovered from rounds 2, 3 and 4 of the two selections were prepared for MiSeq sequencing (Illumina). Single read 150 bp was sufficient to cover the NNK region. DNA reads with average Phred33+ score >25 in the NNK region were translated and unique peptide sequences were tallied using custom python scripts.

Surface Plasmon Resonance (SPR)

The interactions between cyclic peptides: U2i, U2ii, U4i, U4ix and Ub$_1$, $^{K48}$Ub$_2$ and $^{K48}$Ub$_4$, were determined using BIACORE T100 instrument (GE healthcare) equipped with a biotin CAPture kit Series S chip. The buffer in all experiments contained 50 mM HEPES, pH 7.3, 150 mM NaCl, 0.05% Tween20, 2 mM DTT with 0.2% DMSO. Biotinylated Ub$_1$, $^{K48}$Ub$_2$ and $^{K48}$Ub$_4$ were loaded to approximately equal molar amounts on the SPR chip, and various concentrations of cyclic peptides were flowed over at 100 μL/sec for 120 sec, before initiation of dissociation by flowing buffer over at 100 μL/sec for further 700 sec. Traces were fit to the simplest, two-state model for binding. Association was fit to a single exponential assuming pseudo-first order conditions, whereas the dissociation trace was fit to single exponential plus a drift term. Finally, due to the poor quality of the traces for U4ix binding $^{K48}$Ub$_2$, the amplitude of the association kinetic trace at different concentrations of peptide was fit to estimate the lower bound for K$_D$.

Synthesis of Selectively Isotope-Enriched Ub Chains for Nuclear Magnetic Resonance (NMR) Studies Recombinant Ub monomers carrying chain-terminating mutations (either Ub$^{K48R}$ or Ub$^{K63R}$ mutations or C-terminal D77 extension, Ub$^{D77}$) were expressed and purified as detailed elsewhere [include ref. to Pickart C M, Raasi S, Controlled Synthesis of Polyubiquitin Chains, Meth Enzym, 2005]. Isotopic enrichment (by $^{15}$N or $^{13}$C/$^{15}$N) of Ub$^{WT}$ and the abovementioned Ub variants was achieved as detailed [include ref to R. Varadan, O. Walker, C. Pickart, D. Fushman, "Structural properties of polyubiquitin chains in solution," J. Mol. Biol. (2002) 324, 637-647]. Following cell lysis, the proteins were purified by cation exchange and then size-exclusion chromatography. The purity, molecular mass, and proper folding (where applicable) of the purified proteins were confirmed by SDS-PAGE, mass spectrometry (MS), and NMR.

Di-ubiquitins with isotope-enriched distal or proximal Ub were made using controlled Ub chain assembly method utilizing E1 and linkage-specific E2 enzymes, as detailed in [include ref to Varadan et al., JMB 2002 (see above); R.

Varadan, M. Assfalg, A. Haririnia, S. Raasi, C. Pickart, D. Fushman, "Solution conformation of Lys63-linked di-ubiquitin chain provides clues to functional diversity of polyubiquitin signaling," J. Biol. Chem., (2004) 279, 7055-7063; and R. Varadan, M. Assfalg, and D. Fushman, "Using NMR spectroscopy to monitor ubiquitin chain conformation and interactions with ubiquitin-binding domains," Methods in Enzymology, Vol. 399, 2005, pp. 172-192]. K48-linked Ub dimers were obtained by conjugating $Ub_{K48R}$ and $Ub^{D77}$ using E2-25K as the E2 enzyme while K63-linked dimers were assembled from $Ub^{K63R}$ and $Ub^{D77}$ using a combination of Ubc13 and MMS2. The dimers were subsequently purified by cation exchange chromatography and confirmed by SDS PAGE, MS, and NMR.

The assembly of selectively isotope-enriched K48-linked Ub trimers and tetramers was achieved using the following steps. First, the $Ub^{K48R}$-$Ub^{D77}$ dimers with desired isotope-labeling scheme were made using E1 and E2-25K as detailed above. Then the chain-terminating D77 at the C-terminus of the proximal Ub was removed enzymatically using yeast Ub C-terminal hydrolase YUH1, thus making the dimer available for further conjugation. As the next step, this dimer was conjugated to $Ub^{D77}$ to form a trimer. Subsequently, the C-terminal D77 of the trimer was removed to enable assembly of the K48-linked tetramer. At each reaction step, the products were purified by cation exchange chromatography and confirmed by SDS-PAGE, MS, and NMR (where applicable).

NMR Studies

All NMR studies were performed on Bruker Avance III 600 MHz spectrometer equipped with TCI cryoprobe. The sample temperature was set to 23° C. for Ub2ii binding studies or 25° C. for Ub4ix studies, unless indicated otherwise. The protein (monomeric Ub or Ub chains) samples were prepared in 20 mM sodium phosphate buffer (pH 6.8) containing 5-10% D20 and 0.02% (w/v) NaN$_3$. The Ub2ii peptide was dissolved in deuterated DMSO (up to 20 mM concentration) and titrated in µL amounts into 50 µM $^{15}$N-Ub$^{WT}$ or K63-linked Ub$_2$ ($^{15}$N-enriched in the distal domain) to two molar equivalents. Ub2ii was titrated into 100 µM solutions of proximally- or distally-$^{15}$N-enriched $^{K48}$Ub$_2$ to 1:1 or 1:1.3 molar ratio, respectively, as well as into 200 µM $^{K48}$Ub$_2$ with the $^{13}$C/$^{15}$N-enriched proximal or distal Ub unit. Ub4ix titration into K48-linked Ub$_2$, Ub$_3$, and Ub$_4$ was performed in a similar manner, with the starting Ub chain concentration of 200 µM; the chain/peptide molar ratio at the endpoint varied from 1:1 (Ub$_2$) to 1:1.5 or 1:2 for Ub$_3$ and Ub$_4$. Several of these titrations were performed twice and at differing protein concentrations, to verify the reproducibility of the observed spectral changes. Separately, a similar amount of DMSO was added to $^{15}$N-labeled Ub to verify that the presence of DMSO in the peptide-containing stock solution had negligible effect on Ub spectra.

1D $^1$H spectra and 2D $^{15}$N-$^1$H SOFAST-HMQC spectra were acquired at each titration point. To facilitate NMR signal assignment of K48-Ub$_2$ in the Ub2ii-bound state, triple-resonance HNCA, HN(CO)CA, HNCO, and HN(CA)CO experiments were performed using Ub$_2$ samples with either distal or proximal Ub $^{13}$C/$^{15}$N-enriched. The triple-resonance experiments for the distal Ub were performed at 37° C. in order to reduce line broadening. Standard Bruker pulse sequences and pulse sequences generously provided by Ananya Majumdar (Johns Hopkins University) were used for these purposes. Spectra were processed and analyzed using TopSpin (Bruker Inc.) and CCPNMR [reference to Vranken W F, Boucher W, Stevens T J, Fogh R H, Pajon A, Llinas M, Ulrich E L, Markley J L, Ionides J, Laure E D, The CCPN data model for NMR spectroscopy: development of a software pipeline, 2005]. Assignment of the peptide-bound NMR signals of Ub$_4$ was complicated by signal broadening (due to slow tumbling of tetra-Ub) and overlap and by the slow-exchange regime which precluded tracing gradual shifts in the NMR signals upon titration. The residues affected by peptide binding were identified based on strong attenuation/disappearance of their unbound signals combined with the absence of new, bound signals in the close proximity in the spectra.

NMR signal shifts were quantified as chemical shift perturbations using the following equation:

$$CSP=[(\delta_{HA}-\delta_{HB})^2+((\delta_{NA}-\delta_{NB})/5)^2]^{1/2},$$

where $\delta_H$ and $\delta_N$ are chemical shifts of $^1$H and $^{15}$N, respectively, for a given backbone N—H group, and A and B refer to the unbound and bound species, respectively.

To quantify the reduction in intensity of the unbound NMR signals of Ub chains upon peptide binding, intensities in the $^{15}$N-$^1$H spectra recorded at each titration point were measured at the positions corresponding to peaks of the peptide-free species, and then normalized for each residue by dividing by the intensity of the corresponding signal in the spectra recorded before the addition of the peptide. This allowed us to identify and monitor residues involved in slow exchange wherein the unbound signal gradually decreases in intensity upon addition of the peptide.

In Vitro Deubiquitination Assay

In vitro deubiquitination reactions were performed in a Tris buffer (50 mM TRIS, 1 mM TCEP, pH 7.7), containing 2 µM $^{K48}$Ub$_{2/4}$, then the specific DUB (50 mM Tris, 0.5 mM EDTA, 1 mM TCEP and 0.5 mg/ml ovalbumin, pH 7.5) was added. The reaction mixtures were incubated at 37° C. and at the indicated time points the reactions were stopped by taking aliquots and mixed them with 3x sample buffer and boiling. The same amounts were loaded on 14% SDS-PAGE, electro-blotted to nitrocellulose membrane and probed with an anti-Ub antibody. Bands were quantified with Image Quant LAS 4000 (GE Healthcare).

In Vitro Proteasome Degradation Assay

Twelve and a half (12.5) µL: 5.3 µM of synthetic HA-α-globin-K48-linked tetra-Ub and 150 nM proteasome (Enzo) were incubated in the presence of 2 mM ATP, 40 mM Tris, 2 mM DTT and 5 mM MgCl$_2$, at 37° C. for 50 min. The reactions were stopped by the addition of 3x sample buffer. The reactions were loaded on 10% SDS-PAGE, electro-blotted to nitrocellulose membrane and probed with a rabbit anti-HA antibody. Quantification was carried out using the ECL camera software (Fuji).

Radioactive Pulse and Chase

For the assay of inhibitions of protein synthesis, cells were incubated with DMSO, ribosomal inhibitor cycloheximide (CHX), or Ub4ix. After 4 hours, media were replaced with medium containing $^{35}$S-methionine and cysteine (20 µCi) and cells where pulsed for 4 hours. Plates were extensively washed with ice-cold PBS and proteins were extracted from cells using trichloroacetic acid (TCA) precipitation. The radioactive readings were measured using a scintillation counter.

For degradation-inhibition assays, cells were labeled with $^{35}$S-methionine and cysteine (20 µCi) for 16 hours, followed by a chase in cold medium for 4 hours, in the presence of DMSO, proteasome inhibitor MG132, or Ub4ix. Media were then collected, and amino acids were extracted using TCA precipitation. Radioactive readings were measured using a scintillation counter.

Ub4ix Cell Intake

HeLa cells were seeded on glass bottomed (#1.5) 96-well dish and were incubated in the presence of either DMSO or Fluorescein-5-Maleimide-Ub4ix for the indicated times. Medium was then aspirated, and fresh medium was added to the wells. Live cell imaging was carried out using Zeiss LSM-700 confocal microscope equipped with an environmental control module.

Cell Viability Assays and Kinetic Experiments

In order to assess the effect of the cyclic peptides on Hela cells, toxicity was determined using the MTT assay. Equal amounts of cells (8,000 cells/well) were plated in 96-well plates in triplicate. After 24 hours, attached cells were exposed to increasing concentrations of the cyclic peptides for another 24 hours. Thereafter, 10 μL of 12 mM MTT (Vybrant® MTT Cell Proliferation Assay Kit, ThermoFisher) were added per well according to the manufacturer's protocol and incubated for 4 hours at 37° C. This was followed by addition of 100 μL of SDS-HCl solution, thorough mixing and incubated for 4 hours at 37° C. Optical density was recorded at 590 nm with a reference measurement at 630 nm. Half maximal inhibitory concentration ($IC_{50}$) values were defined as the concentrations that correspond to a reduction of cell growth by 50% when compared to values of untreated control cells and depicted as means of relative activity±standard deviation.

Fluorescence-Activated Cell Sorting (FACS) Analysis

Induction of apoptosis in Hela cells by treatment with cyclic peptides were determined after 24 and 48 hours incubation in a dose dependent manner, using annexin V-FITC apoptosis detection kit (BD Biosciences) according to the manufacturer s protocol. Two (2)×10$^5$ cells/well were seeded in 6-well plates and treated with an inhibitor for 24/48 hours in a dose dependent manner. The increase in fluorescence, which indicates the apoptosis level in the treated cells, were monitored using flow cytometry and compared to untreated cells containing DMSO as a negative control and MG132 as a positive control.

Example 1

Total Chemical Synthesis of Biotin Tagged K48-Linked Ub Chains

Figure 7:
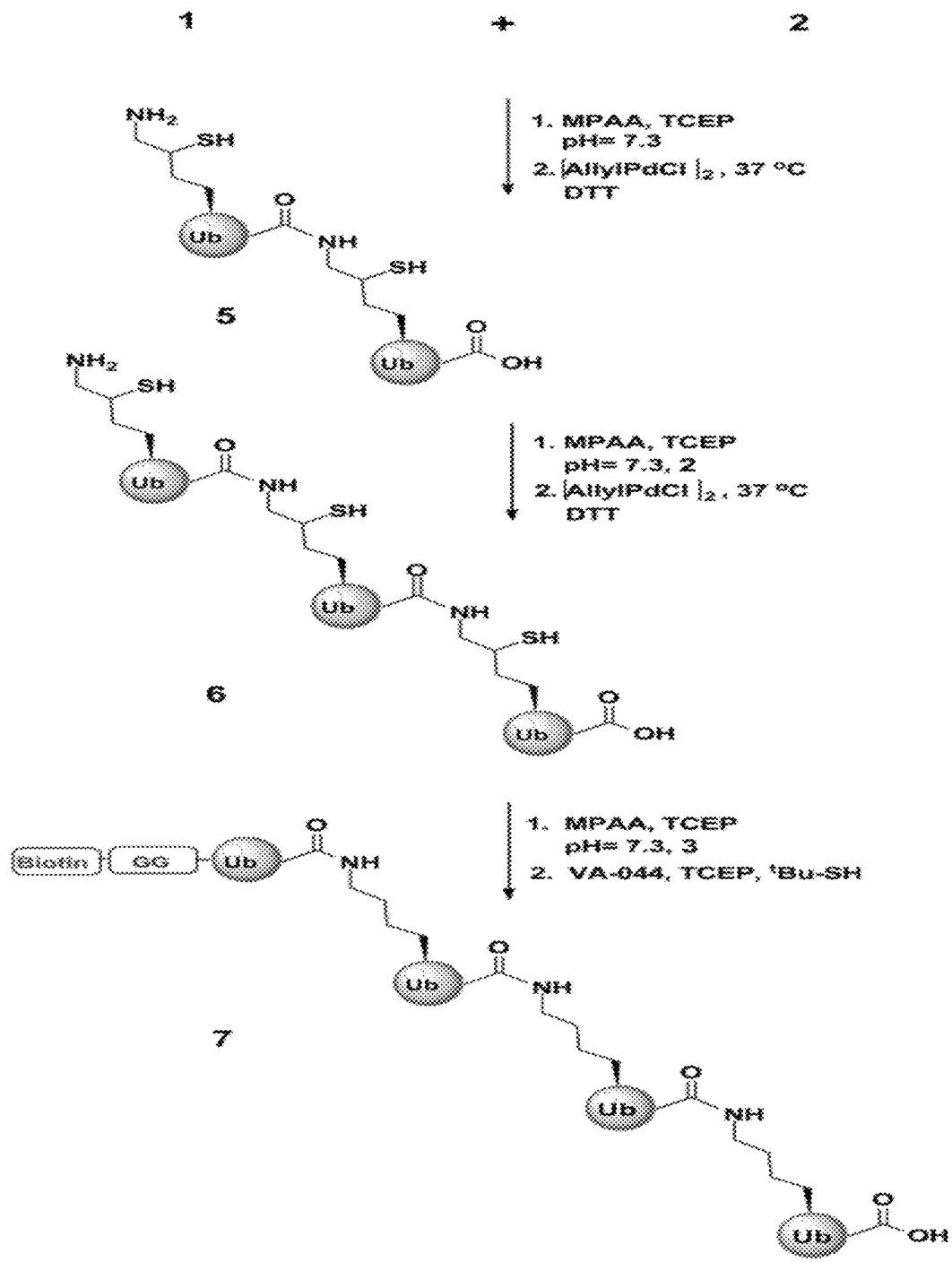
FIG. 7 is a schematic illustration describing synthesis of biotin Ub chain. For the synthesis of the Ub chains, Ub building blocks 1, 2 and 3 (biotin-Ub-MPA) were prepared directly on solid support. The synthesis of the biotin-$^{K48}$Ub$_2$ chain was achieved by ligating 1 and 3 building blocks. The synthesis of biotin-$^{K48}$Ub$_4$ chain was carried out by using a sequential approach, first by ligating building block 1 and 2 to get 5 which was treated with allylpalladium chloride dimer [AllylPdCl]$_2$ to unmask the thiazolidine protection. This enabled ligation of building block 2 in order to get $^{K48}$Ub$_3$, 6. The ligation between 6 ($^{K48}$Ub$_3$) and 3 (biotin-Ub-MPA) gave the biotin-$^{K48}$Ub$_4$, which was subjected to the radical mediated desulfurization and HPLC (employing C4 column and gradient 0-60% B) and FPLC purification steps to give the desired native $^{K48}$Ub$_4$ chain with high purity.

The inventors constructed K48 linked Ub chains suitable for random non-standard peptides integrated discovery (RaPID) selection. This consisted of orthogonally protected δ-mercaptolysine, solid phase peptide synthesis of Ub monomers (modified as required), coupled with isopeptide chemical ligation and desulfurization to prepare mono, di- and tetra-Ub chains[34]. The N-terminus of Ub was further modified with biotin in mono-Ub, as well as the in the distal Ub of di- and the tetra-Ub chains and facilitated immobilization to a solid support (FIG. 1A). Highly homogenous Ub chains were obtained (FIGS. 7 and 8).

Example 2

Discovery of De Novo Cyclic Peptides for K48 Ub Chains

Figures 9A, 9B:
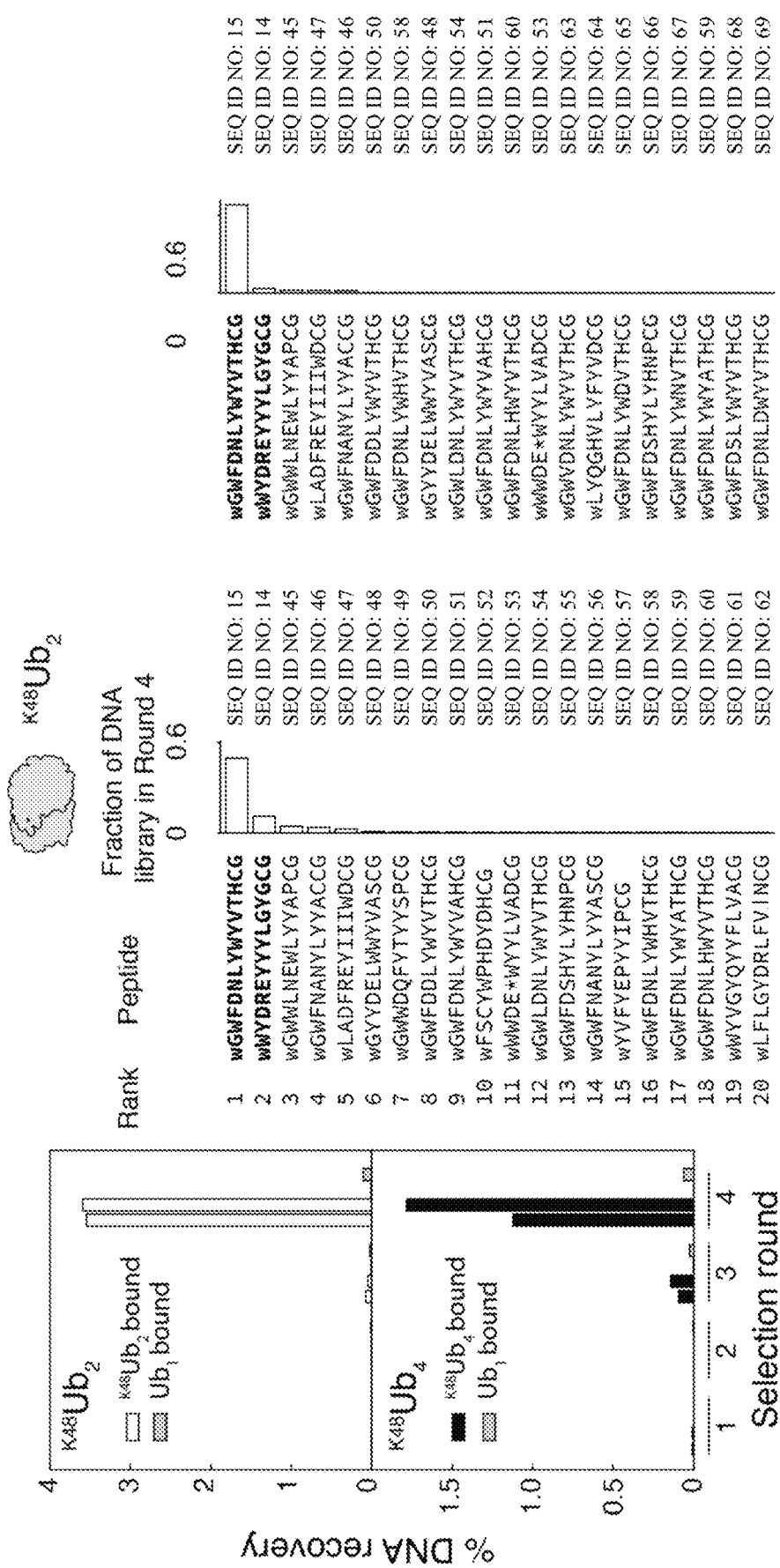
FIGS. 9A-9C are graphs demonstrating the top 20 total DNA recovered increased and specific peptide sequences enriched during RaPID selections. (9A) is a graph of yield of DNA recovered after each round of selection against $^{K48}$Ub$_2$ and $^{K48}$Ub$_4$ targets. An increase in recovered DNA with each round indicated that the libraries were becoming enriched in tight binding cyclic peptides. (9B) is a peptide sequence list with corresponding DNA frequency. For the two repeats of the $^{K48}$Ub$_2$ selection, sequencing of the DNA library after round 4 showed enrichment for the same two peptides (bold), corresponding to Ub2i and Ub2ii. *=any amino acid, X=start 'ATG' codon. (9C) is a peptide sequence list with corresponding DNA frequency. For the two repeats of the $^{K48}$Ub$_4$ selection, similar peptides appeared in the top peptides. Ub4i and Ub4ix shown in bold. In the synthesized peptide Ub4ix, X was replaced with isoleucine.
Figure 9C:
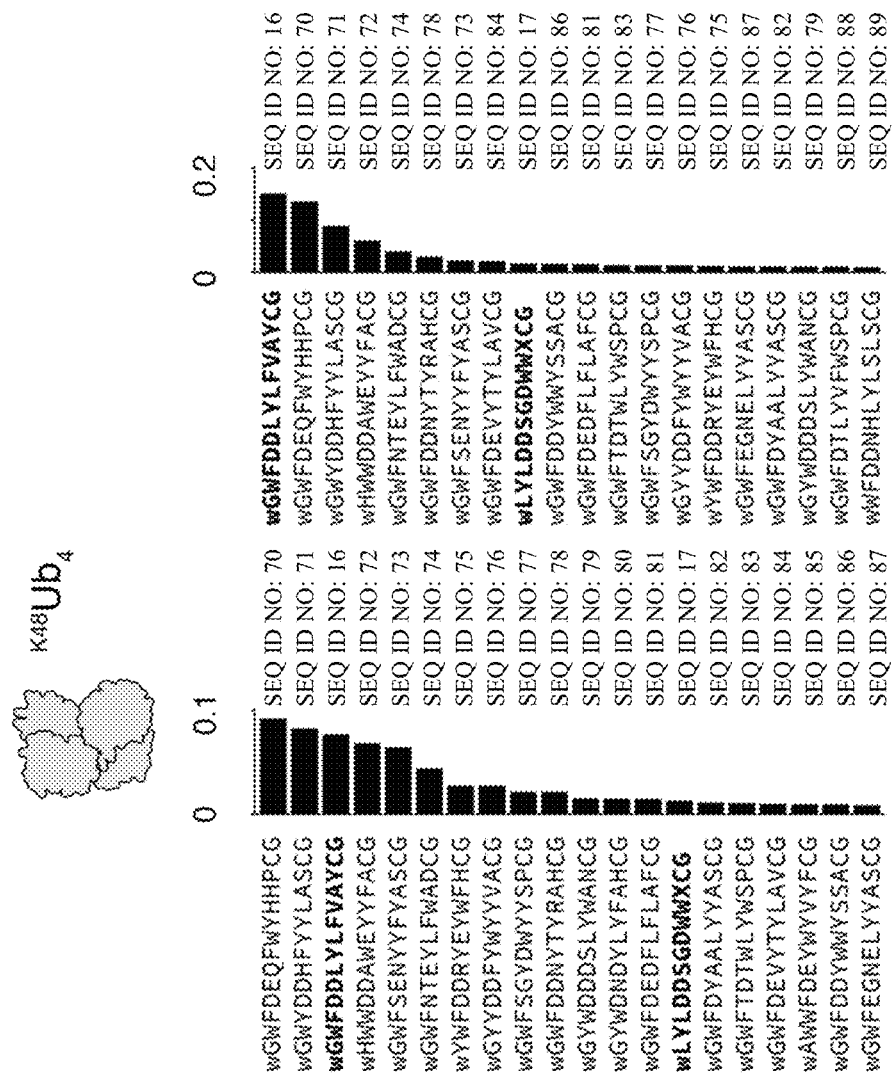
Figure 11A:
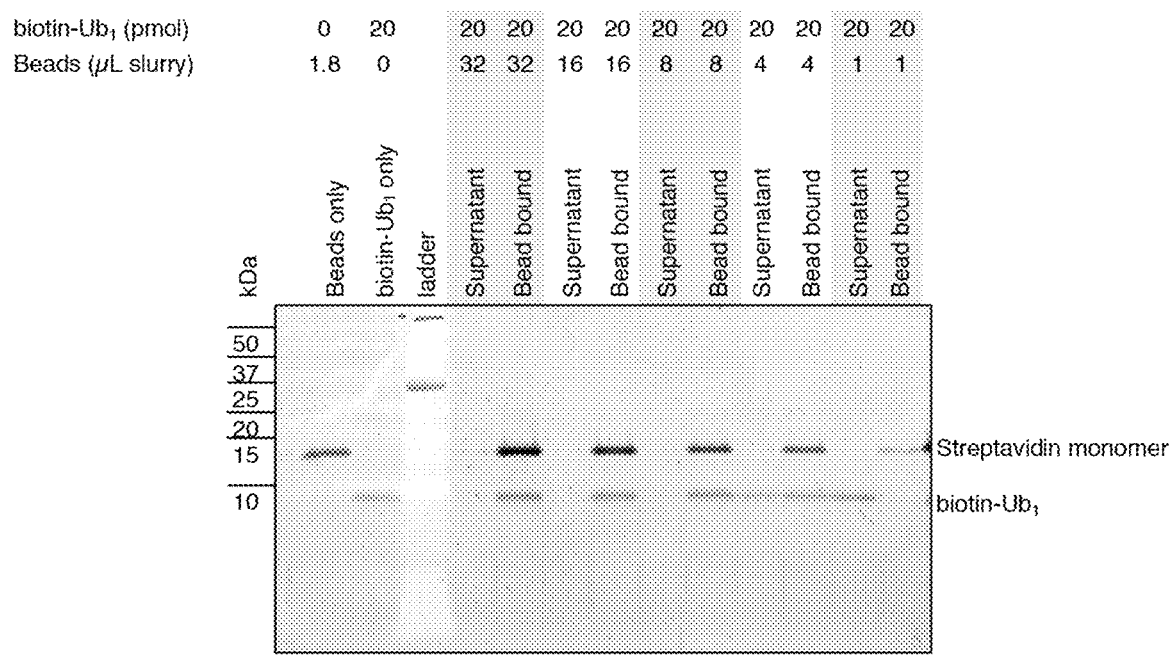
FIGS. 11A-11C are images of SDS-PAGE of biotin Ub chains bound to streptavidin magnetic beads. (11A) is Biotin-Ub$_1$ recovered bound to streptavidin magnetic beads, with increasing amount of biotin-Ub$_1$ removed from the supernatant with greater amounts of beads. (11B) is the same as (11A) for biotin-$^{K48}$Ub$_2$; and (11C) is the same as (11A and 11B) for biotin-$^{K48}$Ub$_4$. Gels were stained using SYPRO Ruby Protein Gel Stain.
Figure 11B:
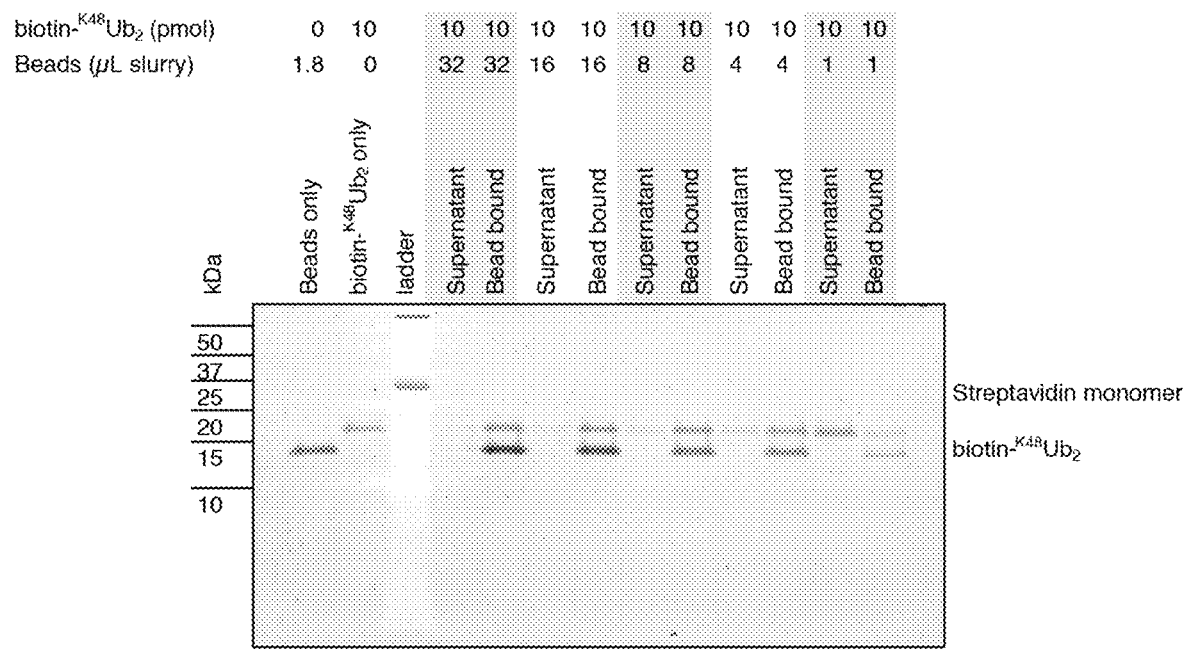
Figure 11C:
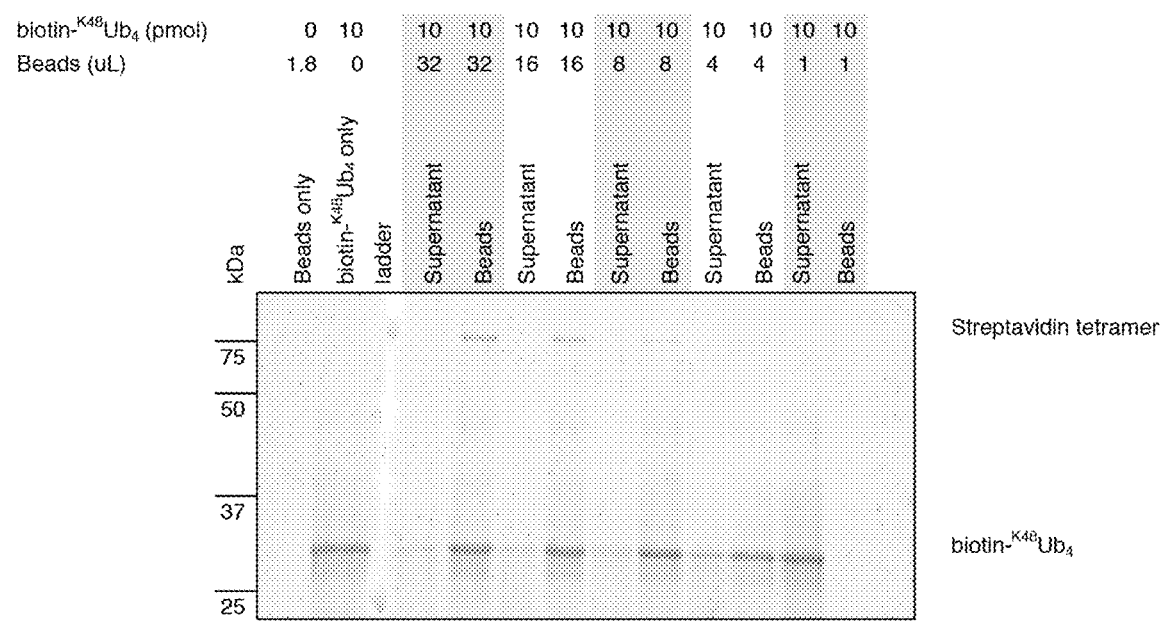
Figure 12:
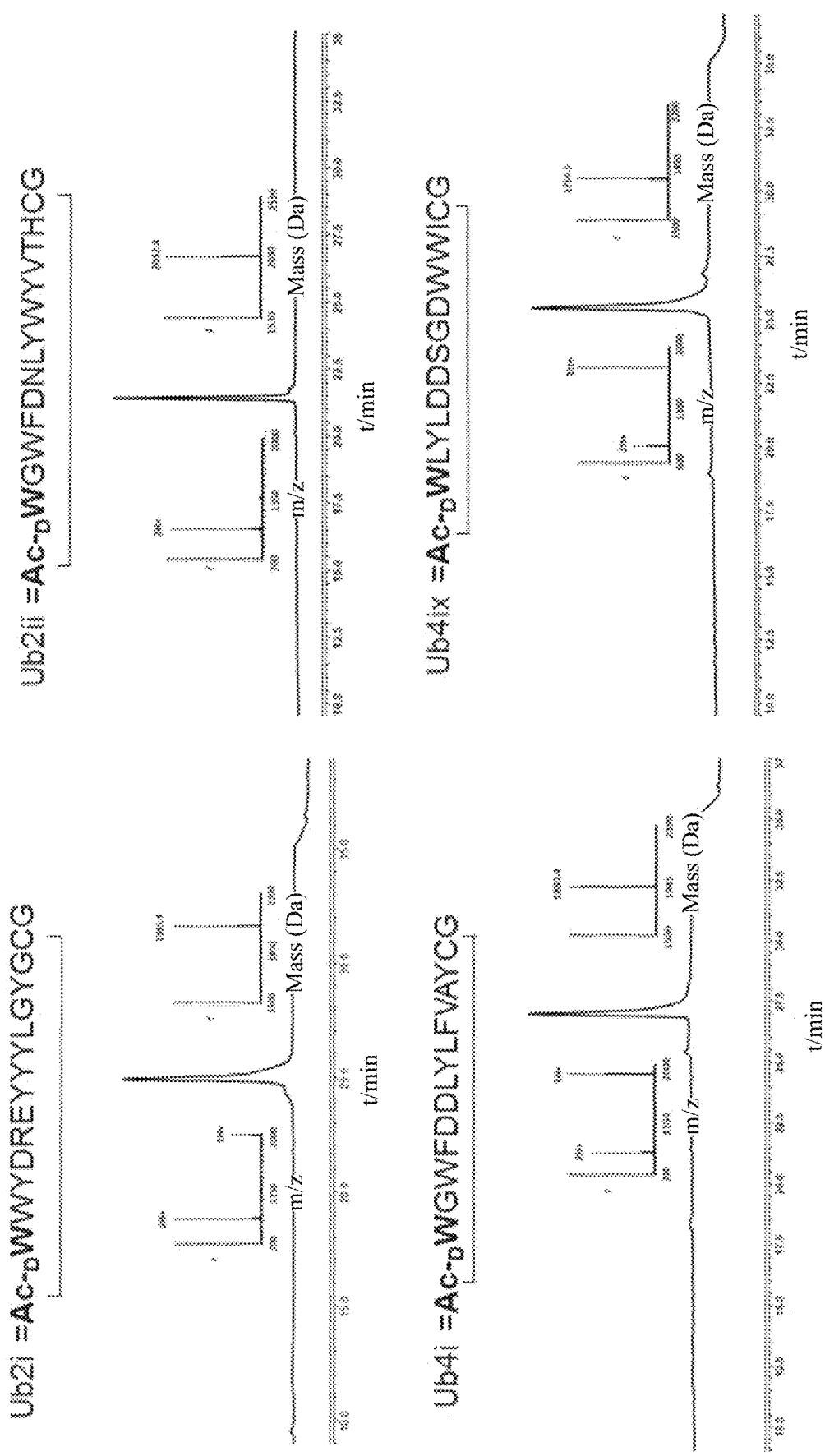
FIGS. 12A-12D are images of chromatograms of analytical HPLC and ESI-MS analyses of chemically synthesized cyclic peptides. The purified cyclic peptides Ub2i (12A), Ub2ii (12B), Ub4i (12C), and Ub4ix (12D) were observed with masses of 1,985.4±0.1 Da, 2,032.4±0.1 Da, 1,893.4±0.1 and 1,766.5±0.2 Da, respectively (calculated 1,985.4 Da, 2,032.4 Da, 1,893.4 and 1,766.5 Da, respectively).
Figure 15:
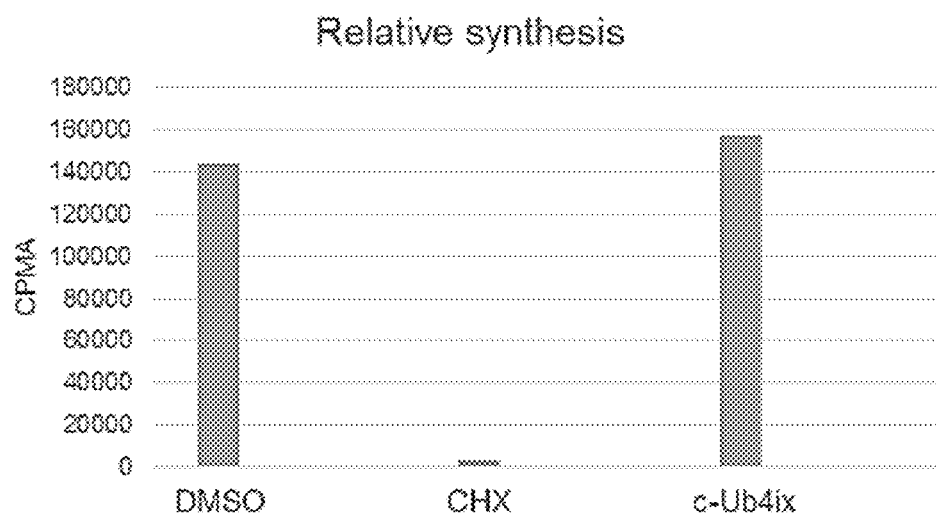
FIG. 15 is a bar graph demonstrating cyclic Ub4ix does not interfere with protein synthesis. HeLa cells were incubated with either DMSO, ribosomal inhibitor cycloheximide (CHX), or Ub4ix. After 4 hours, media were replaced with media containing radioactive Methionine and Cysteine, and cells where pulsed for 4 hours. Cells were thoroughly washed, proteins were extracted from the cells, and the radioactive readings of each sample were measured using a scintillation counter, indicating the extent of incorporation of radiolabeled Methionine and Cysteine into newly synthesized proteins.
Figure 16:
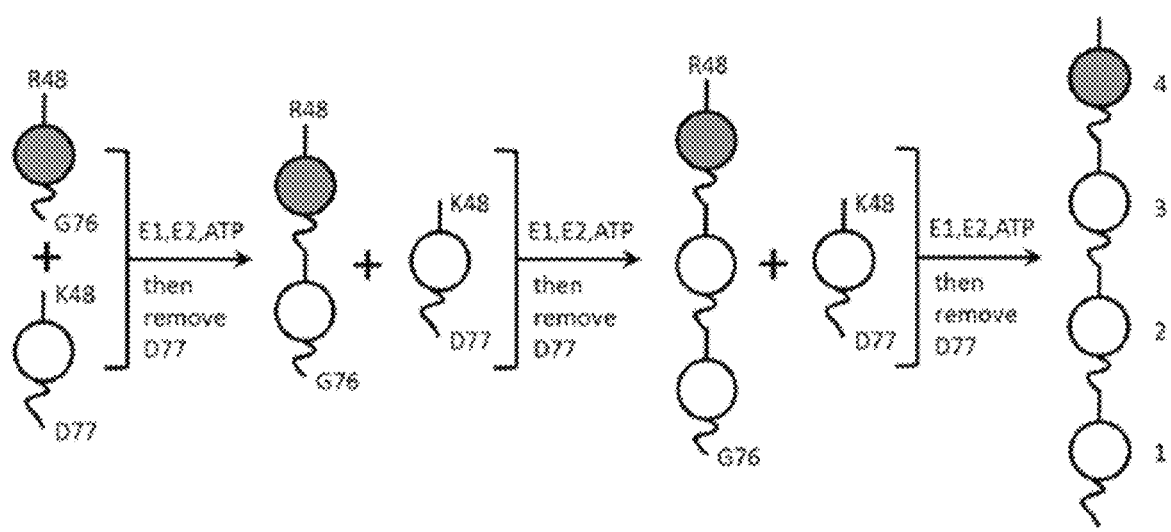
FIG. 16 is a non-limiting scheme describing a strategy of controlled enzymatic assembly of selectively isotope-labeled K48-linked di-, tri-, and tetra-Ub chains. Shown is assembly of Ub chains having the most distal Ub unit (gray) isotope enriched for NMR studies. Chains with other Ub isotope-labeled units were made in a similar manner. Also indicated is the numbering of Ub units in tetra-Ub used in the text.

The chemically synthesized Ub chains, biotin-$^{K48}$Ub$_2$ and biotin-$^{K48}$Ub$_4$, were used as targets for two separate RaPID selections. The initial cyclic peptide libraries contained ~10$^{13}$ unique sequences, with 8 and 12 random amino acids per peptide. After the first round of selection, an additional step was introduced, using biotin-monoUb, to remove cyclic peptides that use monoUb as the main recognition element. Deep sequencing of the DNA library after each round showed that a small number of peptide sequences, and their variants, came to dominate the library by round 4 (FIGS. 1D and 9). Rounds 2-4 were repeated and produced a similar pattern of enrichment (FIG. 9). In the $^{K48}$Ub$_2$ selections the libraries became dominated by the same two sequences, Ub2i and Ub2ii (FIGS. 1D and 9). In the $^{K48}$Ub$_4$ selections, many of the top peptides had appreciable sequence identity to Ub2i (FIG. 9). One of these high identity peptides (58%) was chosen for further study, Ub4i, together with a shorter, lower identity peptide (8%), Ub4ix (FIG. 1D).

Example 3

De Novo Cyclic Peptides Tightly Bind K48-Linked Ub Chains

Figure 29A:
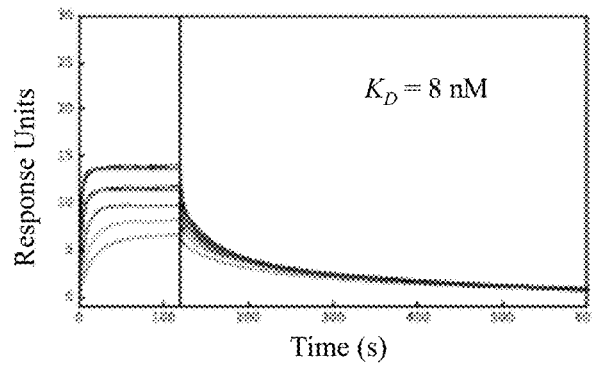
FIGS. 29A-29B are graphs showing $^{K48}$Ub$_4$ binding to synthesized cyclic peptides. (29A and 29B) are graphs of surface plasmon resonance (SPR) binding curves of Ub$_4$_a (29A) and Ub$_4$_e (29B) to $^{K48}$Ub$_4$. Dissociation constants (K$_D$), are shown for the synthesized peptides.
Figure 29B:
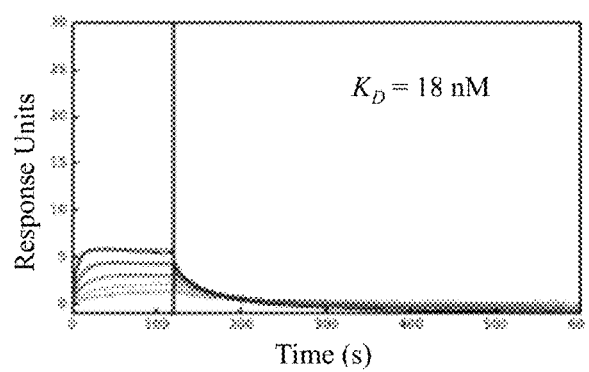

To test the binding and specificity of the Ub2i, Ub2ii, Ub4i, Ub4ix, Ub4_a and Ub4_e cyclic peptides, each were prepared by chemical synthesis for Surface Plasmon Resonance (SPR) analysis (FIGS. 1E and 29). Each peptide was flowed over Ub$_1$, $^{K48}$Ub$_2$ and $^{K48}$Ub$_2$ immobilized on SPR chips. There was no detectable binding to Ub$_1$ for any of the peptides, as expected, as Ub$_1$ binding was explicitly selected against during the RaPID protocol. Whereas, Ub2i and Ub2ii tightly bound their selection target $^{K48}$Ub$_2$, with low nM $K_D$ values (40±12 nM, 33±8 nM, respectively, FIG. 1E). However, Ub2i and Ub2ii also strongly bound $^{K48}$Ub$_4$, with a low apparent $K_D$ and an increased SPR response (FIG. 1E). This was consistent with a higher stoichiometry of binding to the tetramer, which could be explained by additional binding sites in $^{K48}$Ub$_4$. Indeed, the $^{K48}$Ub$_2$ structure can be superimposed twice on the $^{K48}$Ub$_4$ crystal structure (FIG. 10). Ub4i, Ub4ix, Ub4_a and Ub4_e also tightly bound their selection target $^{K48}$Ub$_4$. However, similar to Ub2i and Ub2ii, Ub4i also bound $^{K48}$Ub$_2$. This was perhaps unsurprising, given the high sequence identity between Ub4i and Ub2i. On the other hand, the cyclic peptides Ub4ix, Ub4_a and Ub4_e, were highly specific for the Ub tetramer—weakly binding $^{K48}$Ub$_2$ (>1 μM $K_D$, >900 nM $K_D$, and >20,000 nM $K_D$, respectively) but binding tightly to $^{K48}$Ub$_4$ ($K_D$=6±1 nM, $K_D$=8 nM, and $K_D$=18 nM, respectively) (FIGS. 1E and 29).

Example 4

Mapping of Cyclic Peptide Ub2ii/Di-Ub Interface Using NMR

Figure 2A:
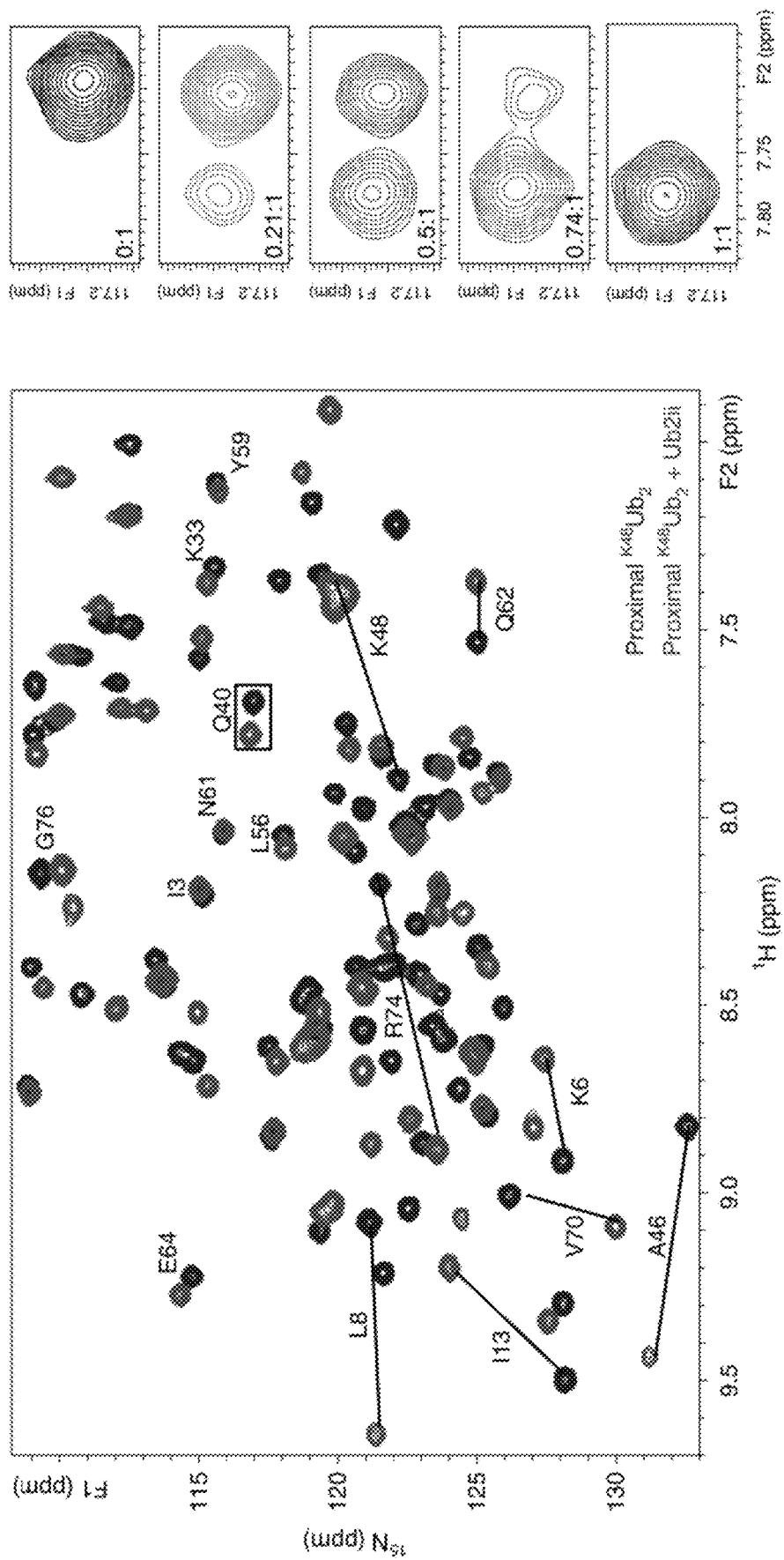
Figure 17A:
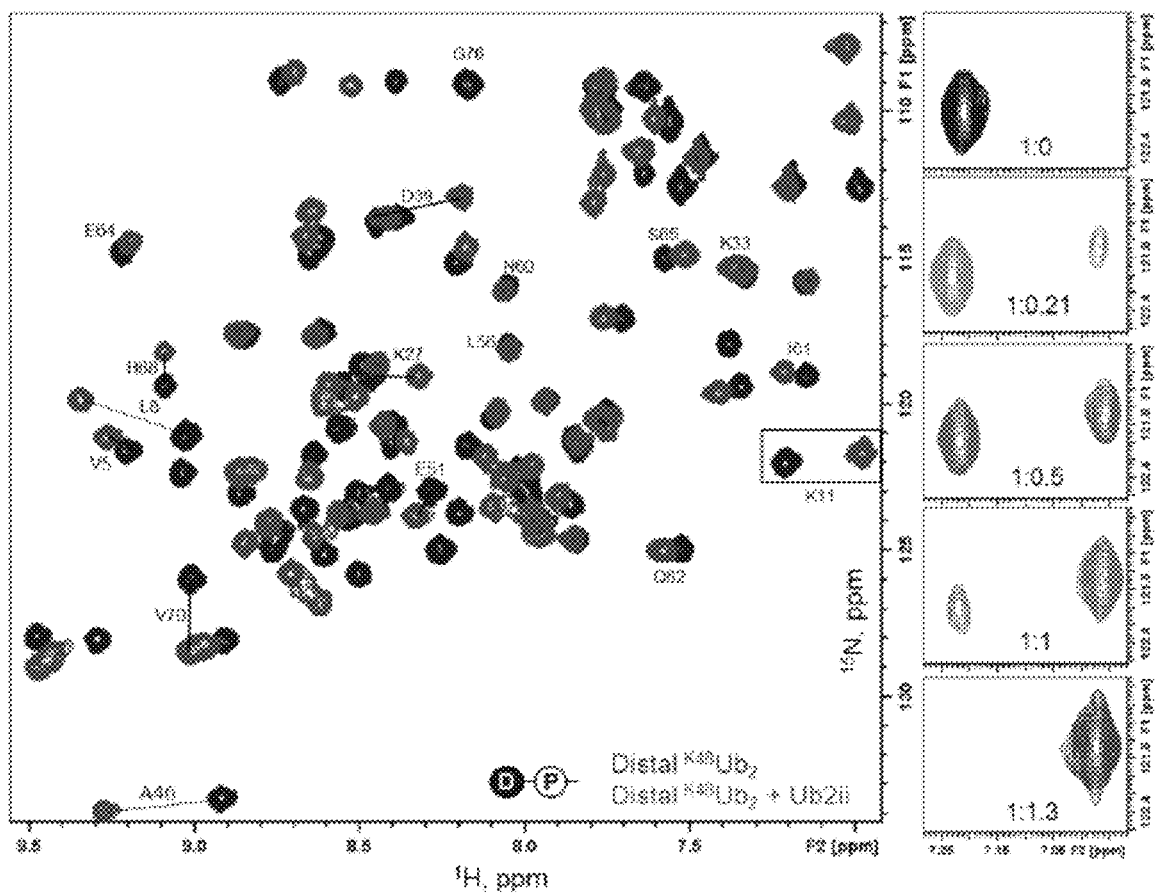
FIGS. 17A-17C are graphs showing residue-specific perturbations in the distal Ub unit of $^{K48}Ub_2$ upon Ub2ii binding. (17A) is an overlay graph of the $^1H$-$^{15}N$ correlation spectra of $^{K48}Ub_2$ (distal Ub) free (blue) and in the presence of 1.3 molar equivalent of Ub2ii (red). Signal shifts for select residues are indicated. Insets on the right illustrate the behavior of the signal of K11 (boxed) during the titration with the peptide, at the indicated Ub$_2$:peptide molar ratios. (17B) is vertical bar graphs of residue-specific chemical shift perturbations at the endpoint of titration with Ub2ii in the distal (left) and proximal (right) Ub units in $^{K48}Ub_2$. (17C) is vertical bar graphs of intensities of the unbound signals of the distal (left) and proximal (right) Ub units in $^{K48}Ub_2$ at the endpoint of titration with Ub2ii. The signal intensity for each residue was normalized to the corresponding intensity measured in the absence of peptide. The drawings indicate which Ub unit in Ub$_2$ is analyzed. Asterisks indicate residues that could not be detected or could not be reliably quantified due to signal overlap.
Figure 17B:
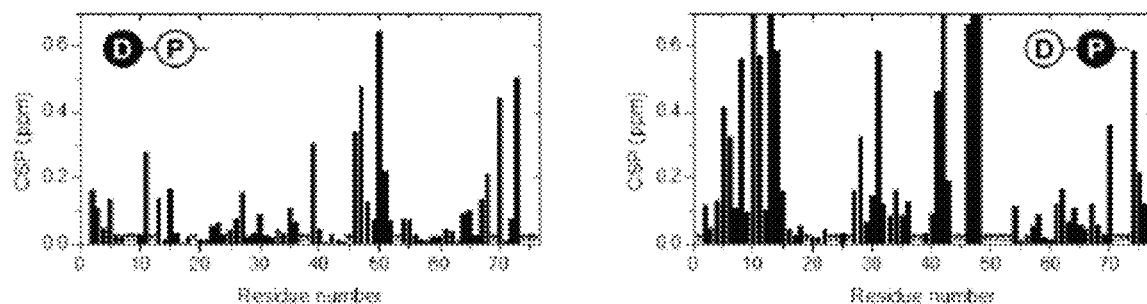
Figure 17C:
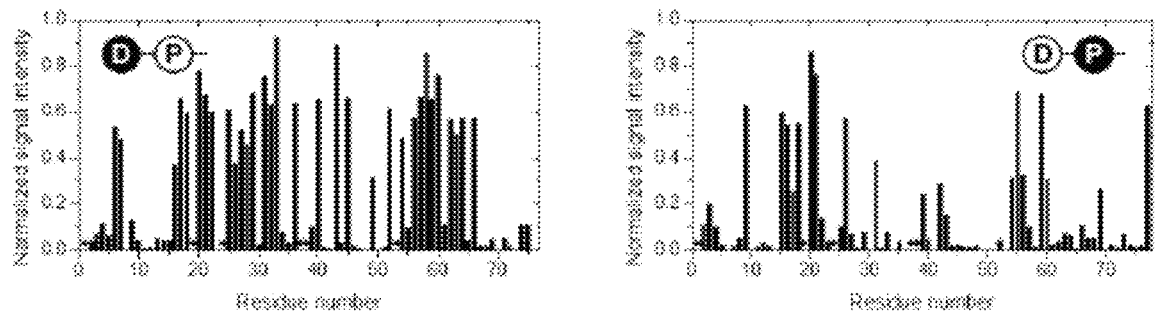

The inventors then used NMR to confirm physical interaction between the cyclic peptide and $^{K48}$Ub$_2$ and to map the residues/sites involved in the peptide binding. The peptide was titrated into solution of di-Ub where either distal or proximal Ub was $^{15}$N-enriched, and the binding was monitored by $^1$H-$^{15}$N NMR. The titration revealed site-specific interactions (FIGS. 2A-B, and 17). Interestingly, the results followed a text-book example of slow exchange, where a gradual decrease in intensity of the "unbound" Ub signals was accompanied by appearance and increase of alternate ("bound") signals. At the 1:1 molar ratio, practically all affected unbound signals vanished (FIGS. 2A and 17 right insets). The slow exchange behavior and absence of gradual signal shifts likely reflected slow off-rates, in agreement with the strong, nM-$K_D$ binding (FIGS. 1E and 29). Also in agreement with the ~1 per minute off-rates the inventors were unable to detect exchange cross-peaks in zz-exchange NMR spectra even with exchange times up to 2 s. The spectral perturbations were accompanied by a concomitant decrease in amide protons (T2) of amide protons from ~25 ms to ~16 ms, consistent with an increase in the overall size of $Ub_2$ upon complexation with the peptide. The $Ub_2$ sites affected by Ub2ii binding were mapped to residues in and around the L8-I44-V70 hydrophobic patch on both Ub units (FIGS. 2B and C), indicating that the cyclic peptide intercalates between the two Ub units in $Ub_2$. Binding of both Ub units to the same cyclic peptide was supported by the fact that the saturation was reached at the 1:1 molar ratio indicating a 1:1 stoichiometry of the resulting $Ub_2$/Ub2ii complex. This reported interface is similar to that used in $^{K48}Ub_2$ interactions with ubistatins, as well as K48-specific protein receptors. Interestingly, despite the general symmetry between the two Ub units in $Ub_2$, the CSPs and the directions of the signal shifts are drastically different between the distal and the proximal Ubs. Combined with the fact that only a single set of "bound" NMR signals is observed for each Ub unit, this indicates that Ub2ii binds $^{K48}Ub_2$ unidirectionally and in a single conformation.

Example 5

Binding to an Alternately Linked K63-diUb or monoUb is Weak

Figure 18B:
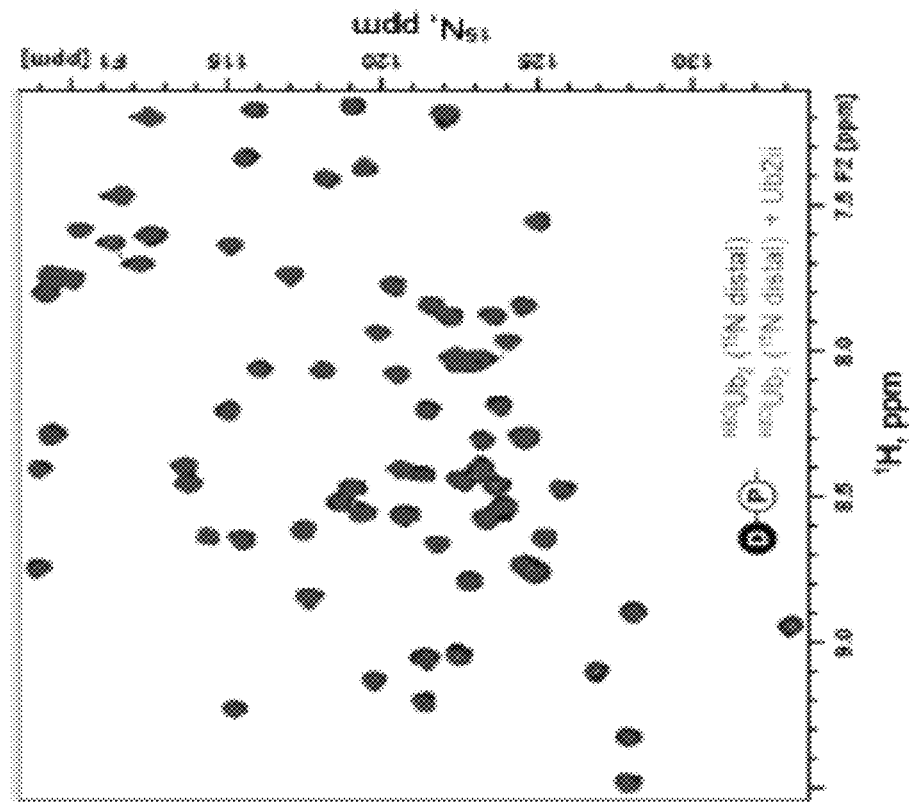
FIGS. 18A-18B are graphs showing that cyclic Ub2ii peptide exhibits only weak and non-specific interactions with monomeric Ub and K63Ub$_2$. (18A) is an overlay graph of $^1H$-$^{15}N$ correlation spectra of monomeric Ub free (blue) and in the presence of 1 molar equivalent of Ub2ii (red). There is essentially no change (except for attenuation of the G75 signal) upon peptide addition. (18B) is an overlay graph of $^1H$-$^{15}N$ correlation spectra of the distal Ub in $^{K63}Ub_2$ free (blue) and in the presence of 1 molar equivalent of Ub2ii (red). Overall signal attenuation occurred as the peptide was added, however no significant residue-specific changes and no new (bound) NMR signals were detected at these conditions. The spectra overlay at 2 molar equivalents was similar to the one shown here; the signal intensities in the red spectrum were more attenuated.
Figure 18A:
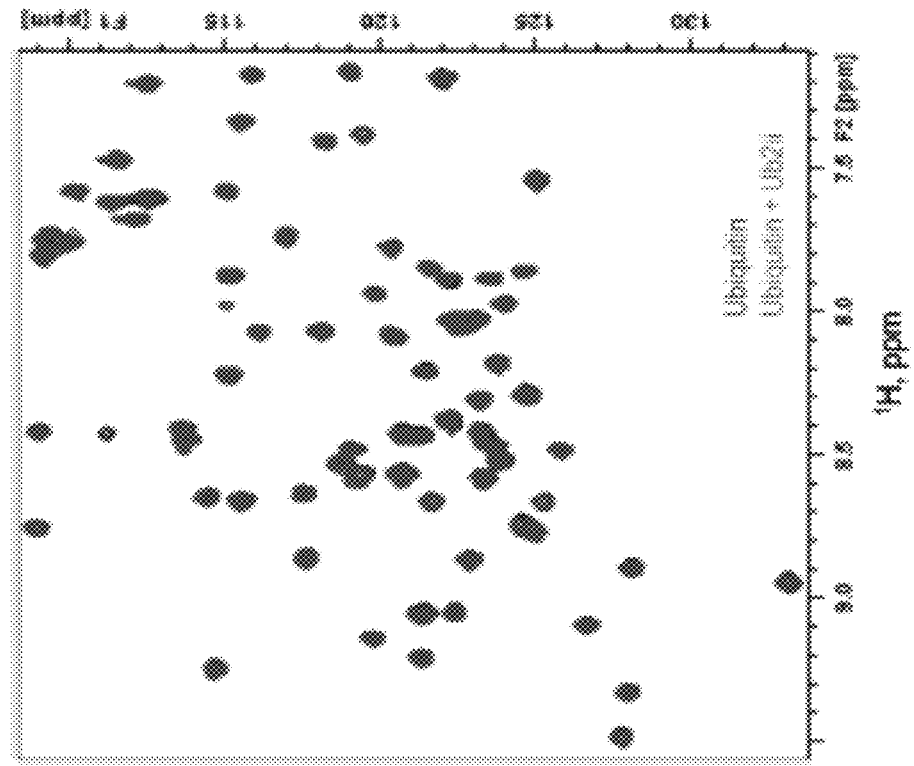

A titration of Ub2ii with $^{K63}Ub_2$ showed practically no signal shifts and no detectable appearance of alternate ("bound") signals even up to 2:1 molar ratio (peptide:$Ub_2$) (FIG. 18). Thus, the binding of Ub2ii to diUb is strongly dependent on linkage type; Ub2ii is highly specific for $^{K48}Ub_2$ over $^{K63}Ub_2$. However, there was a noticeable overall reduction in signal intensity of the $^{K63}Ub_2$ spectra, and even stronger (down to ~12 ms) decrease in $^1H\ T_2$, indicative of size-increase due to peptide binding. However, the absence of clear residue-specific spectral perturbations suggested that the binding could be non-specific and much weaker than for $^{K48}Ub_2$. The higher apparent size of the complex ($^1H$ T2 shorter than for $^{K48}Ub_2$/Ub2ii and comparable with that for tetraUb) could reflect oligomerization of $^{K63}Ub_2$ wherein Ub units from two di-ubiquitins bind to the same peptide, similar to $^{K63}Ub_2$ interactions with ubistatins.

The inventors therefore examined if and how the peptide interacts with monomeric Ub, hoping that the higher concentrations used in NMR experiments (over SPR) might detect any weak binding. Similar to $^{K48}Ub_2$, the spectra showed the appearance of alternate ("bound") signals and no shifts, indicative of slow exchange. However, significantly higher concentrations of Ub2ii (in terms of peptide/Ub molar ratio) were required to observe appreciable alternate signals (FIG. 18), indicating much weaker binding than for $^{K48}Ub_2$ and is consistent with the SPR measurements (Table 1).

Figure 19A:
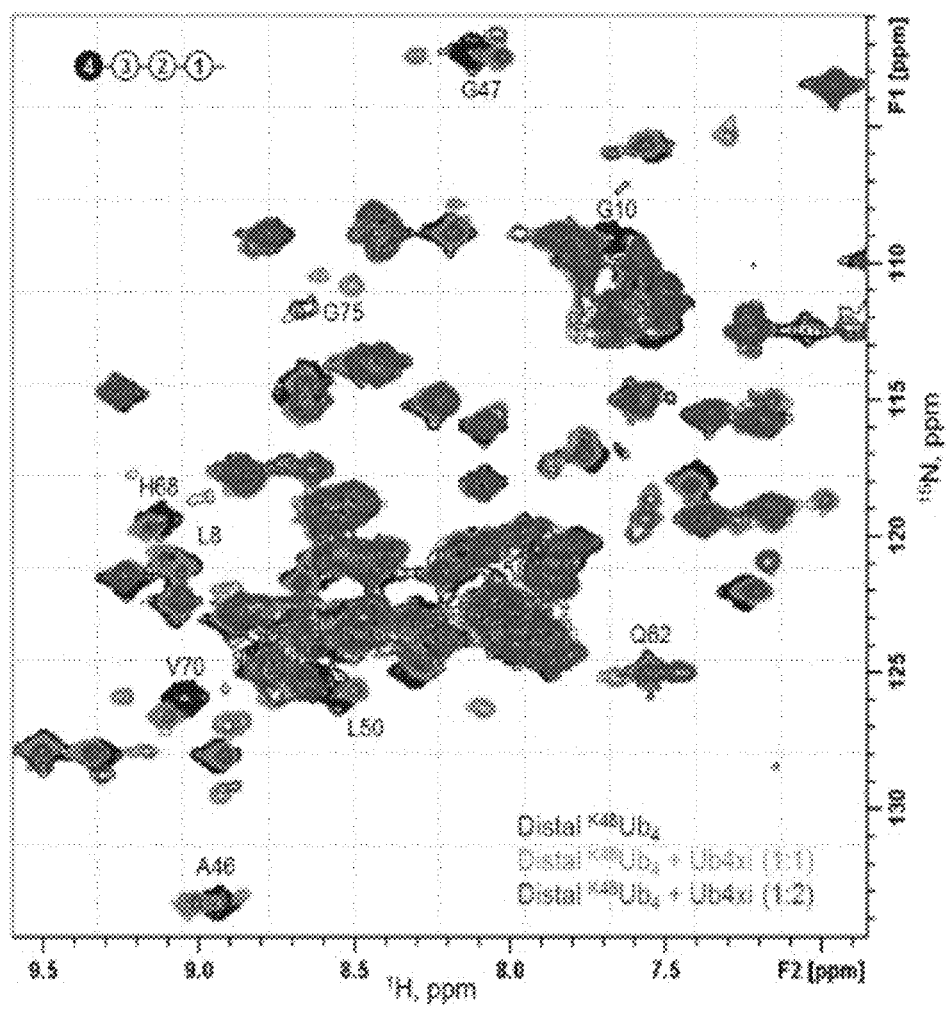
FIGS. 19A-19B are graphs showing residue-specific perturbations in the distal Ub unit of $^{K48}Ub_4$ upon Ub4xi binding. (19A) is an overlay graph of the $^1H$-$^{15}N$ correlation spectra of $^{K48}Ub_4$ (distal Ub) free (blue) and in the presence of 1 (green) and 2 (red) molar equivalents of Ub4xi (red). Select perturbed residues are indicated. Note several alternate (bound) peaks, for example, for residues G47, Q62, and G75. (19B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap.
Figure 19B:
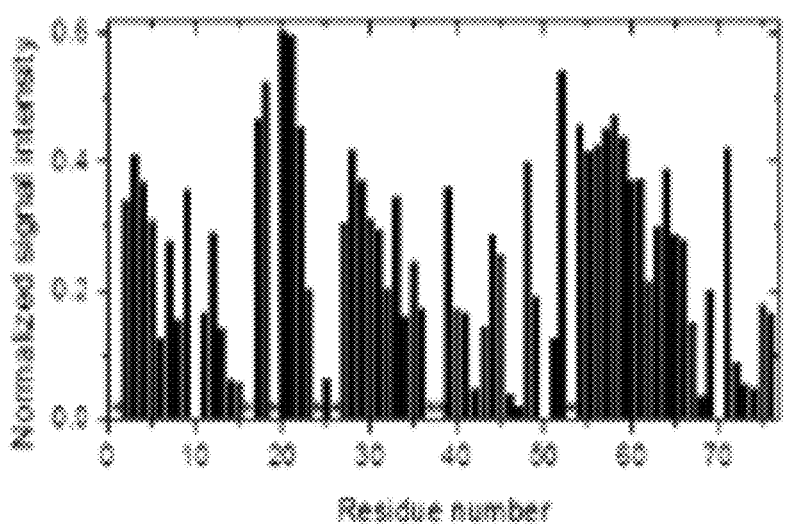
Figure 20A:
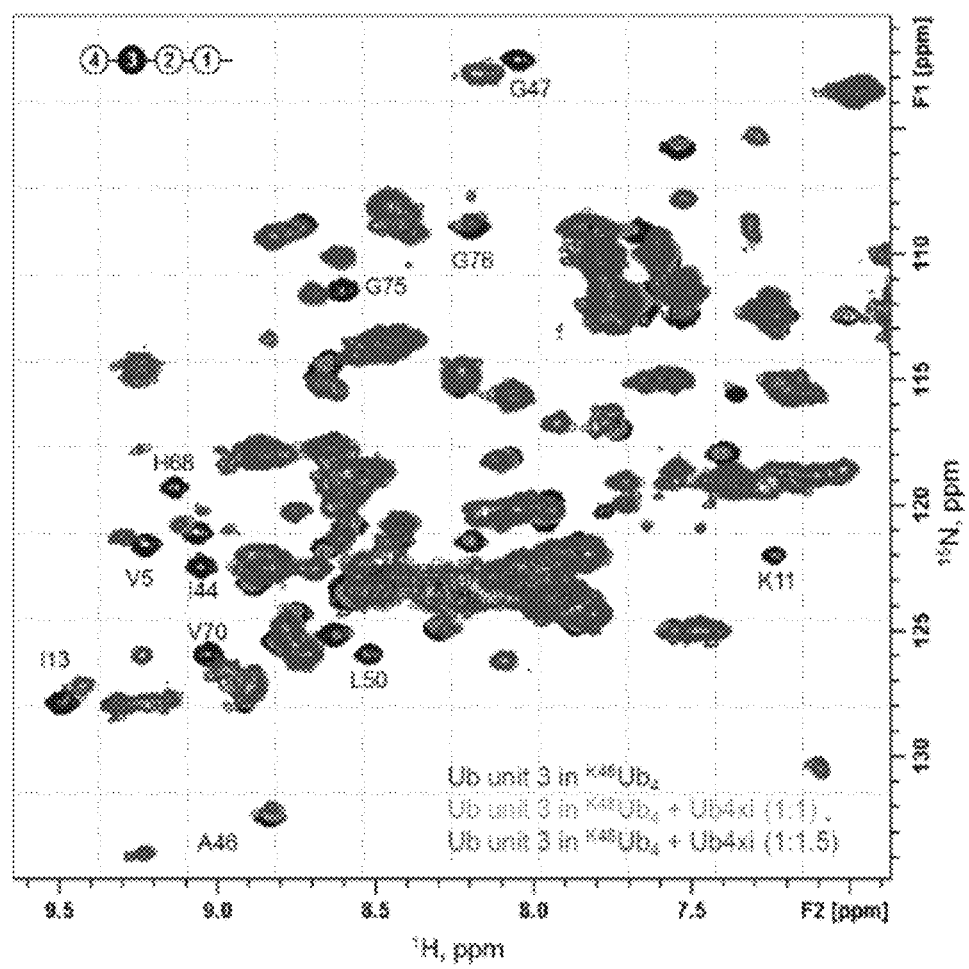
FIGS. 20A-20B are graphs showing residue-specific perturbations in Ub unit 3 of K48Ub4 upon Ub4xi binding. (20A) is an overlay graph of the $^1H$-$^{15}N$ correlation spectra of $^{K48}Ub_4$ (unit 3 $^{15}N$-enriched) free (blue) and in the presence of 1 (green) and 1.5 (red) molar equivalents of Ub4xi (red). Select perturbed residues are indicated. (20B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap.
Figure 20B:
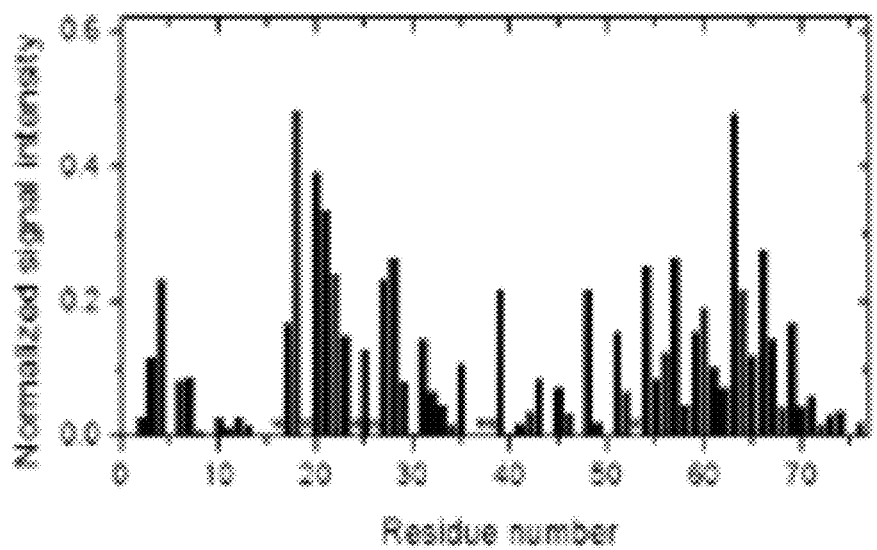
Figure 21A:
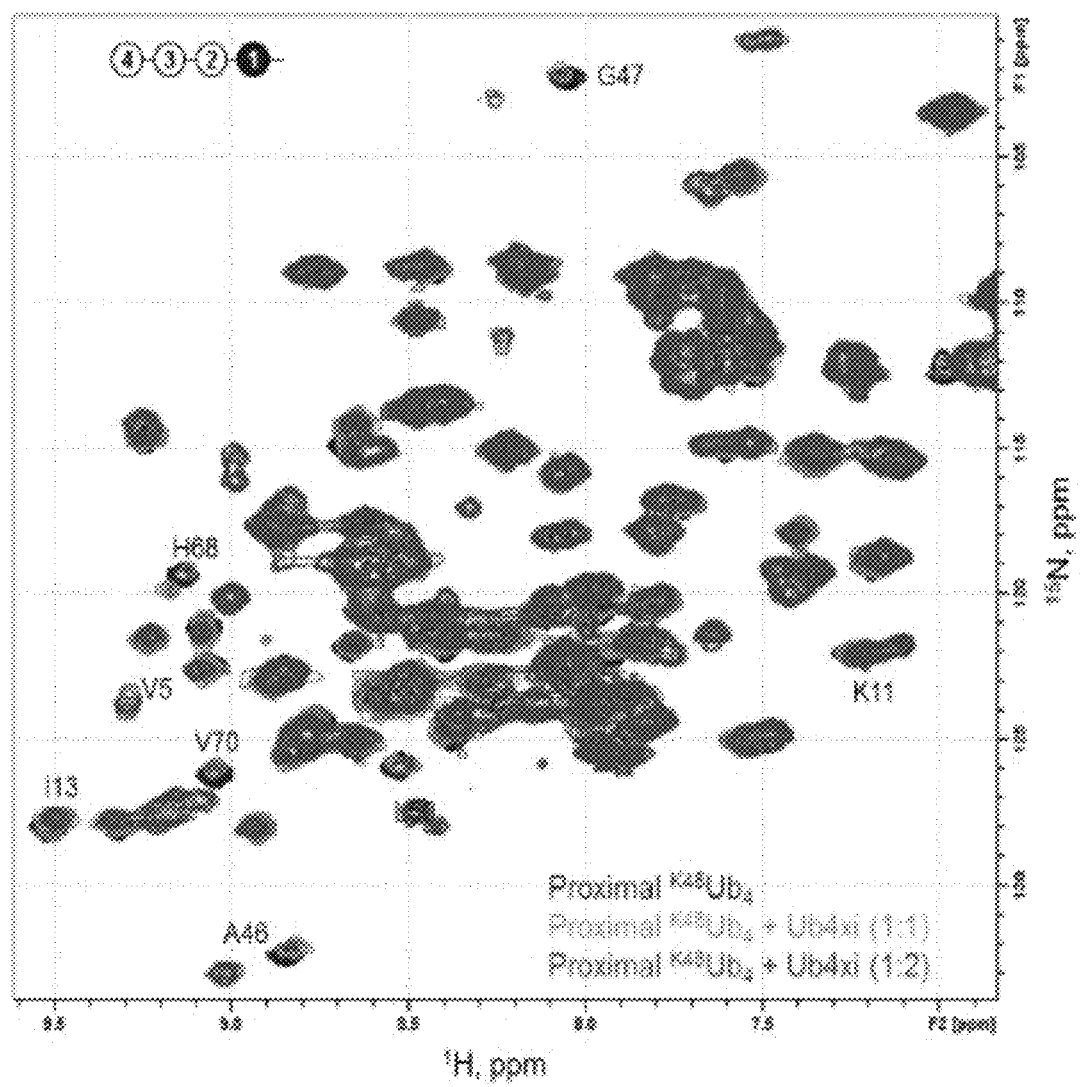
FIGS. 21A-21B are graphs showing residue-specific perturbations in the proximal Ub of $^{K48}Ub_4$ upon Ub4xi binding. (21A) is an overlay graph of the $^1H$-$^{15}N$ correlation spectra of $^{K48}Ub_4$ (proximal) free (blue) and in the presence of 1 (green) and 2 (red) molar equivalents of Ub4xi. Select perturbed residues are indicated. (21B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap. The average amide $^1H$ T2 decreased from ~13 ms (free Ub$_4$) to ~10 ms at 1:1 to 8 ms at 1:2 Ub$_4$:peptide molar ratio, indicative of gradual increase in the overall size of Ub$_4$ upon Ub4xi binding and suggesting a 1:2 stoichiometry of binding.
Figure 21B:
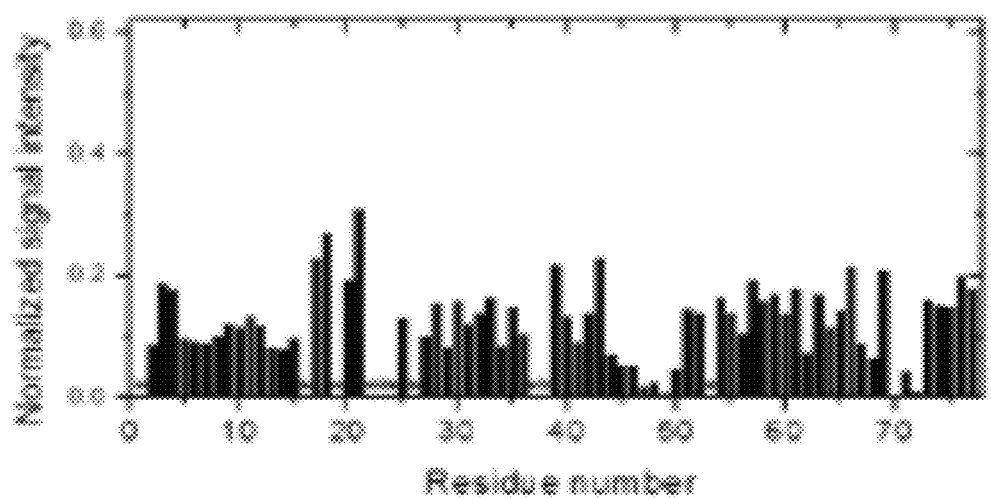
Figures 22A, 22B:
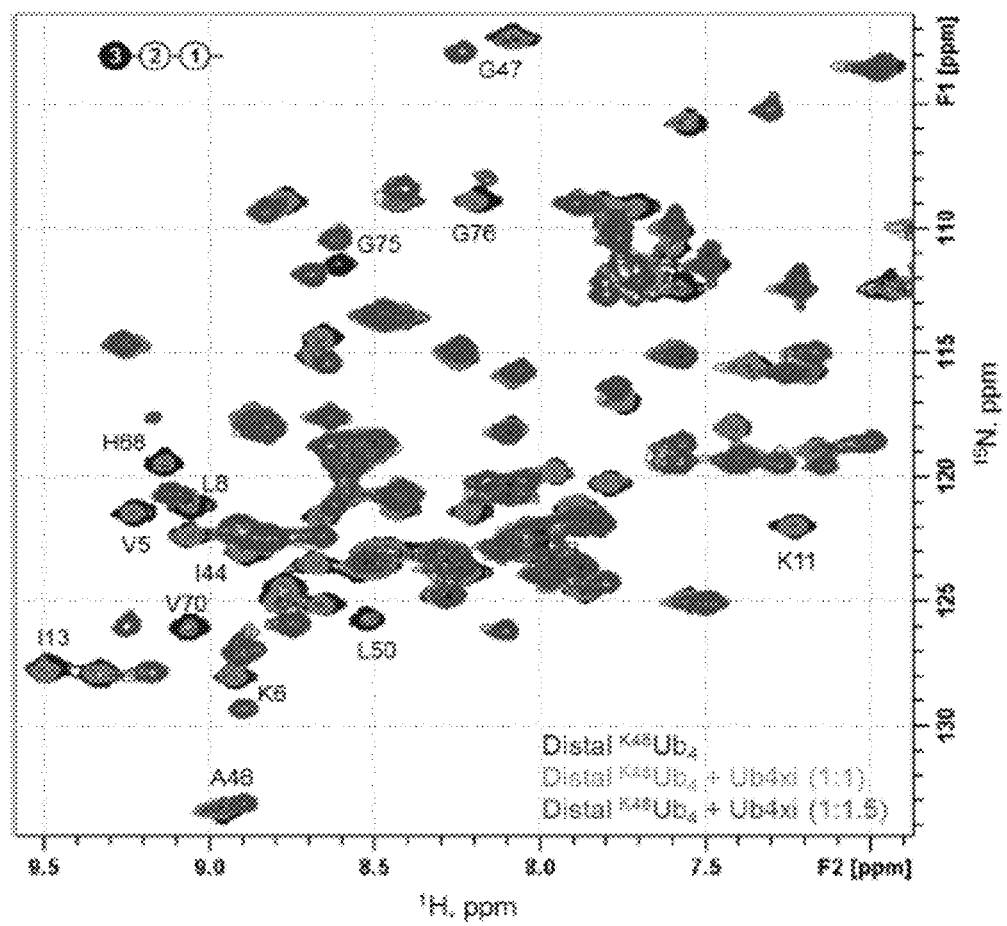
FIGS. 22A-22B are graphs showing residue-specific perturbations in the distal Ub of $^{K48}Ub_3$ upon Ub4xi binding. (22A) is an overlay graph of the $^1H$-$^{15}N$ correlation spectra of $^{K48}Ub_3$ (distal) free (blue) and in the presence of 1 (green) and 1.5 (red) molar equivalents of Ub4xi. Select perturbed residues are indicated. (22B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap.
Figure 23A:
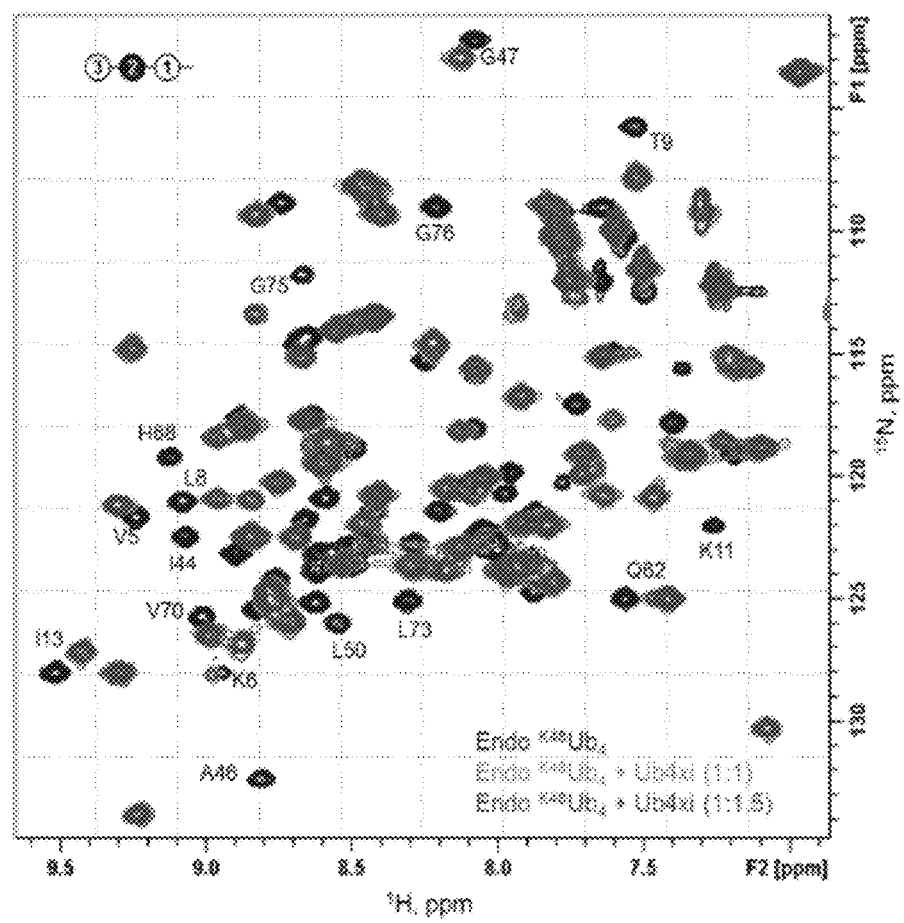
FIGS. 23A-23B are graphs showing residue-specific perturbations in the endo Ub of $^{K48}Ub_3$ upon Ub4xi binding. (23A) is an overlay graph of the $^1H$-$^{15}N$ correlation spectra of $^{K48}Ub_3$ (endo Ub $^{15}N$ enriched) free (blue) and in the presence of 1 (green) and 1.5 (red) molar equivalents of Ub4xi. Select perturbed residues are indicated. Note little change between the green and red spectra, indicating that most signals are in the bound state already at the 1 molar equivalent of the peptide. (23B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap.
Figure 23B:
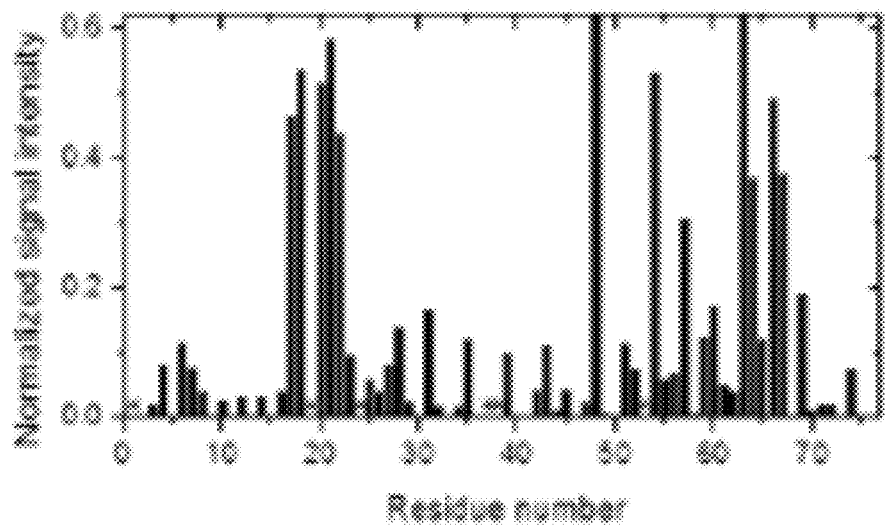
Figure 24A:
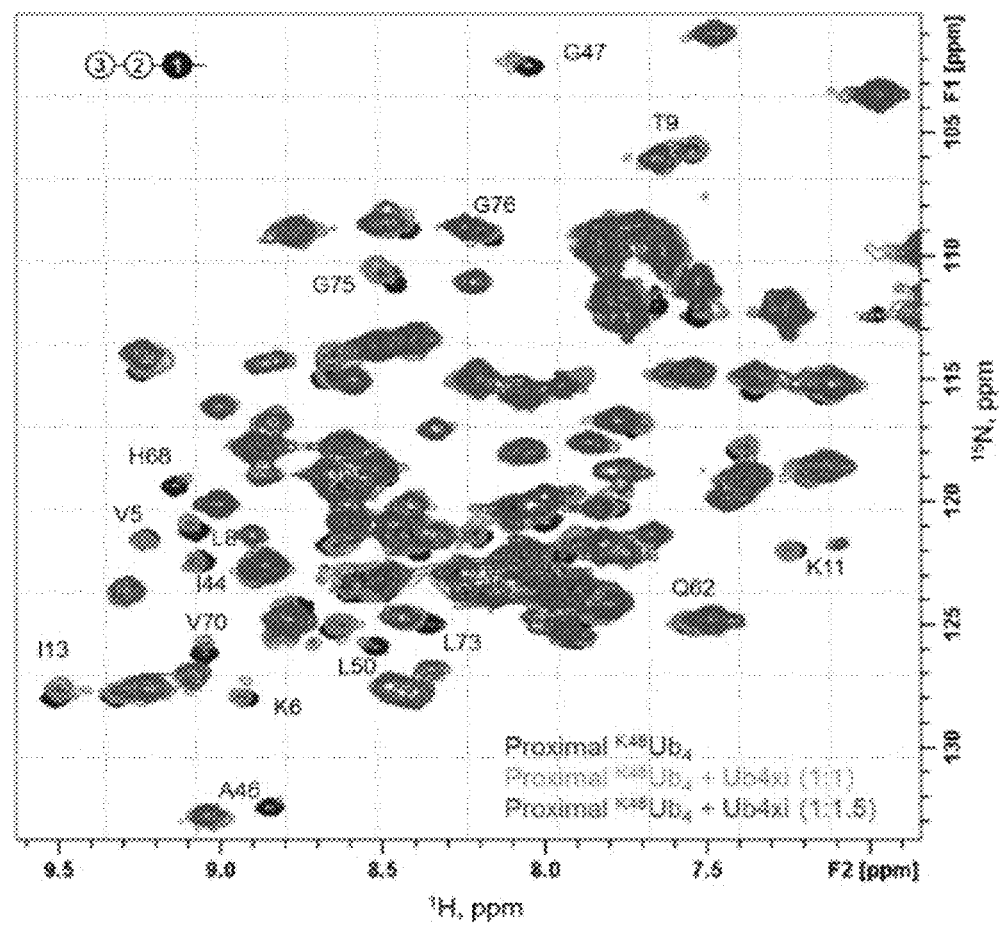
FIGS. 24A-24B are graphs showing residue-specific perturbations in the proximal Ub of $^{K48}$Ub$_3$ upon Ub4xi binding. (24A) is an overlay graph of the $^1$H-$^{15}$N correlation spectra of $^{K48}$Ub$_3$ (proximal) free (blue) and in the presence of 1 (green) and 1.5 (red) molar equivalents of Ub4xi. Select perturbed residues are indicated. (24B) is a vertical bar graph of intensities of the unbound signals at the endpoint of titration with Ub4xi. The signal intensity for each residue was normalized to the corresponding intensity measured in the absence of peptide. Asterisks indicate residues that could not be detected or could not be reliably quantified due to signal overlap.
Figure 24B:
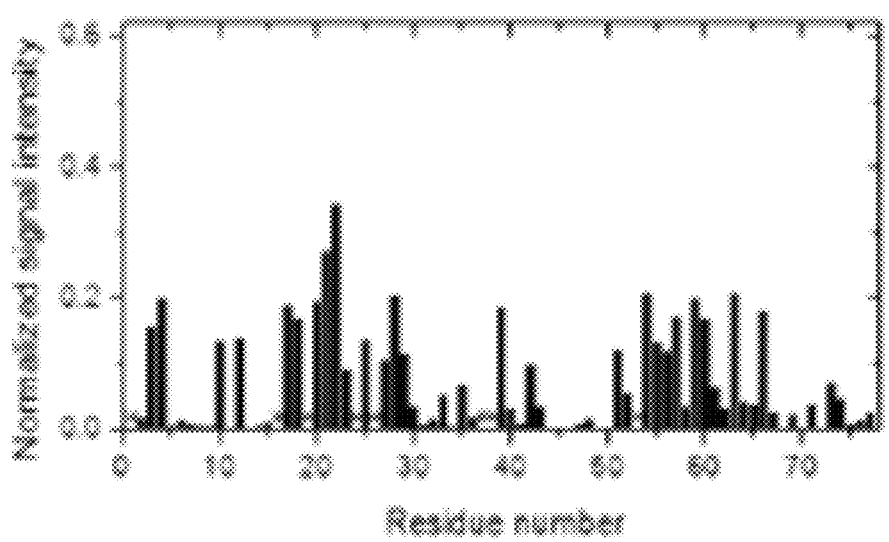
Figure 25:
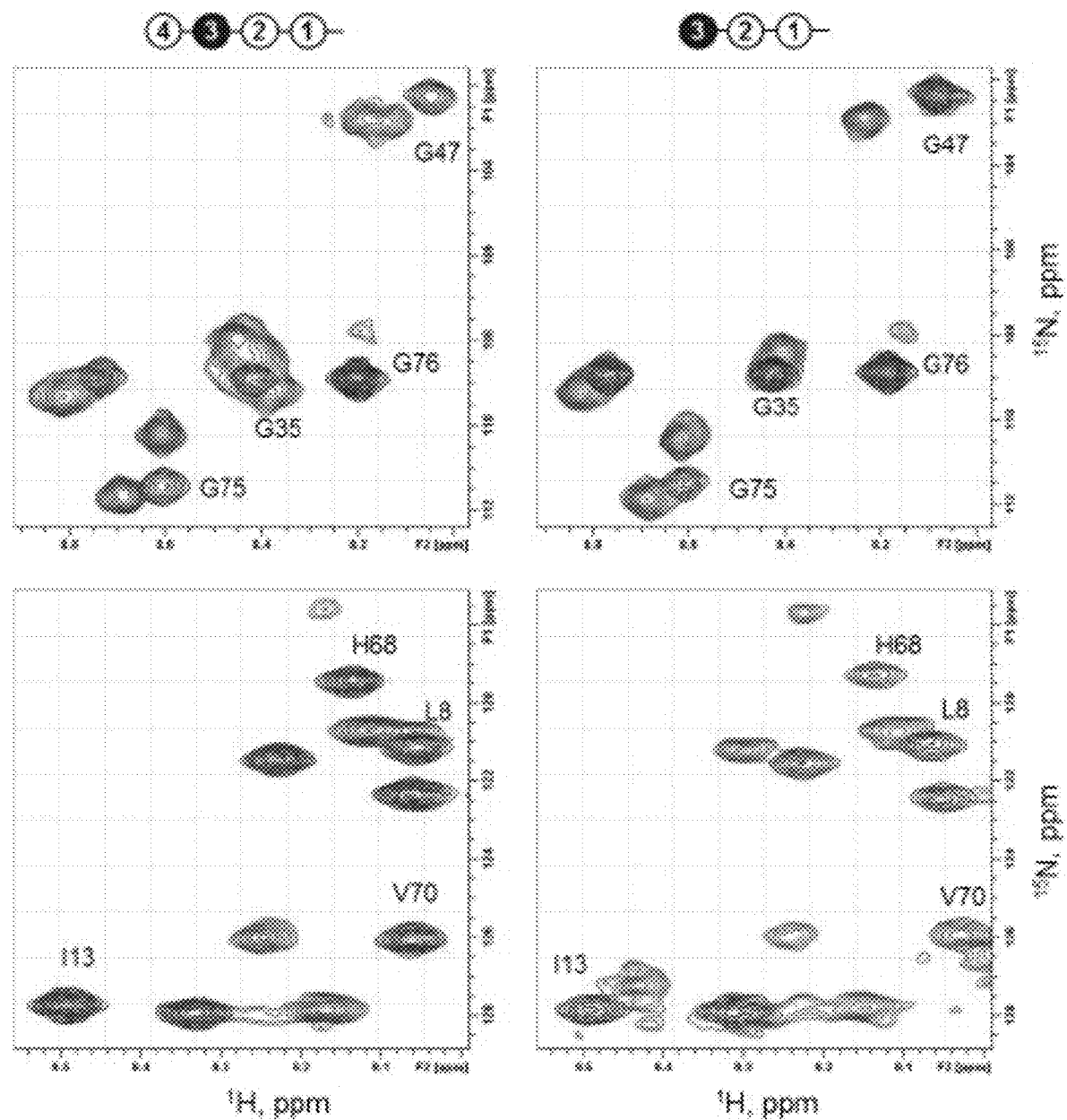
FIG. 25 is a graph showing that the Ub unit 3 in $^{K48}$Ub$_4$ and the distal Ub in $^{K48}$Ub$_3$ exhibit similar patterns of residue-specific NMR signal shifts upon Ub4xi binding. Shown are overlay graphs of the regions of the $^1$H-$^{15}$N correlation spectra of Ub unit 3 in $^{K48}$Ub$_4$ (left column) and the distal Ub in $^{K48}$Ub$_3$ (right column), free (blue) and in the presence of 1 molar equivalent (red) of Ub4xi. Unbound signals corresponding to select residues are indicated.
Figure 26:
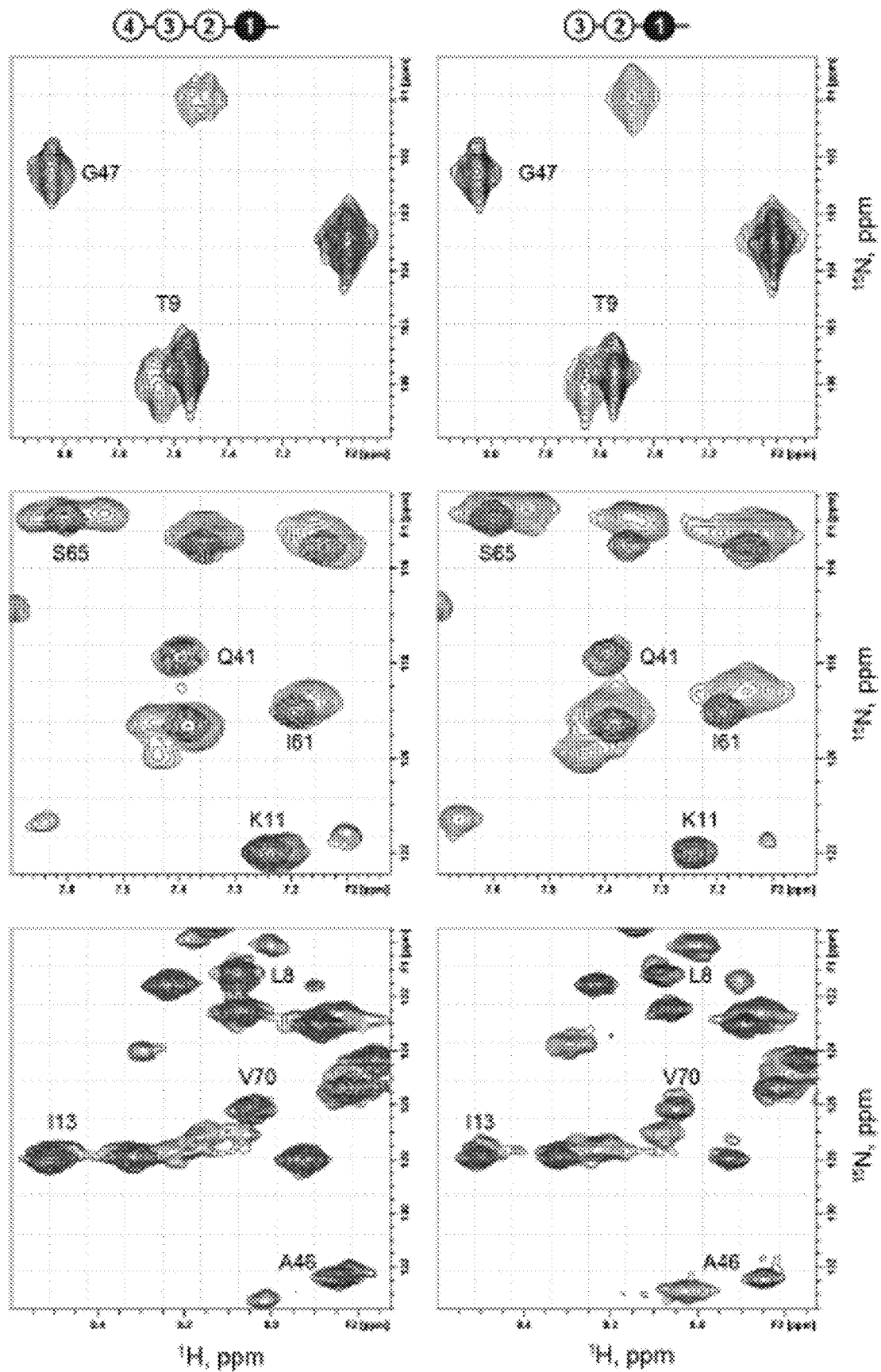
FIG. 26 is a graph showing that the proximal Ub units in $^{K48}$Ub$_4$ and $^{K48}$Ub$_3$ exhibit similar patterns of residue-specific NMR signal shifts upon Ub4xi binding. Shown are overlay graphs of regions of the $^1$H-$^{15}$N correlation spectra of the proximal Ub in $^{K48}$Ub$_4$ (left column) and in $^{K48}$Ub$_3$ (right column), free (blue) and in the presence of 1 molar equivalent (red) of Ub4xi. Unbound signals corresponding to select residues are indicated.
Figure 27:
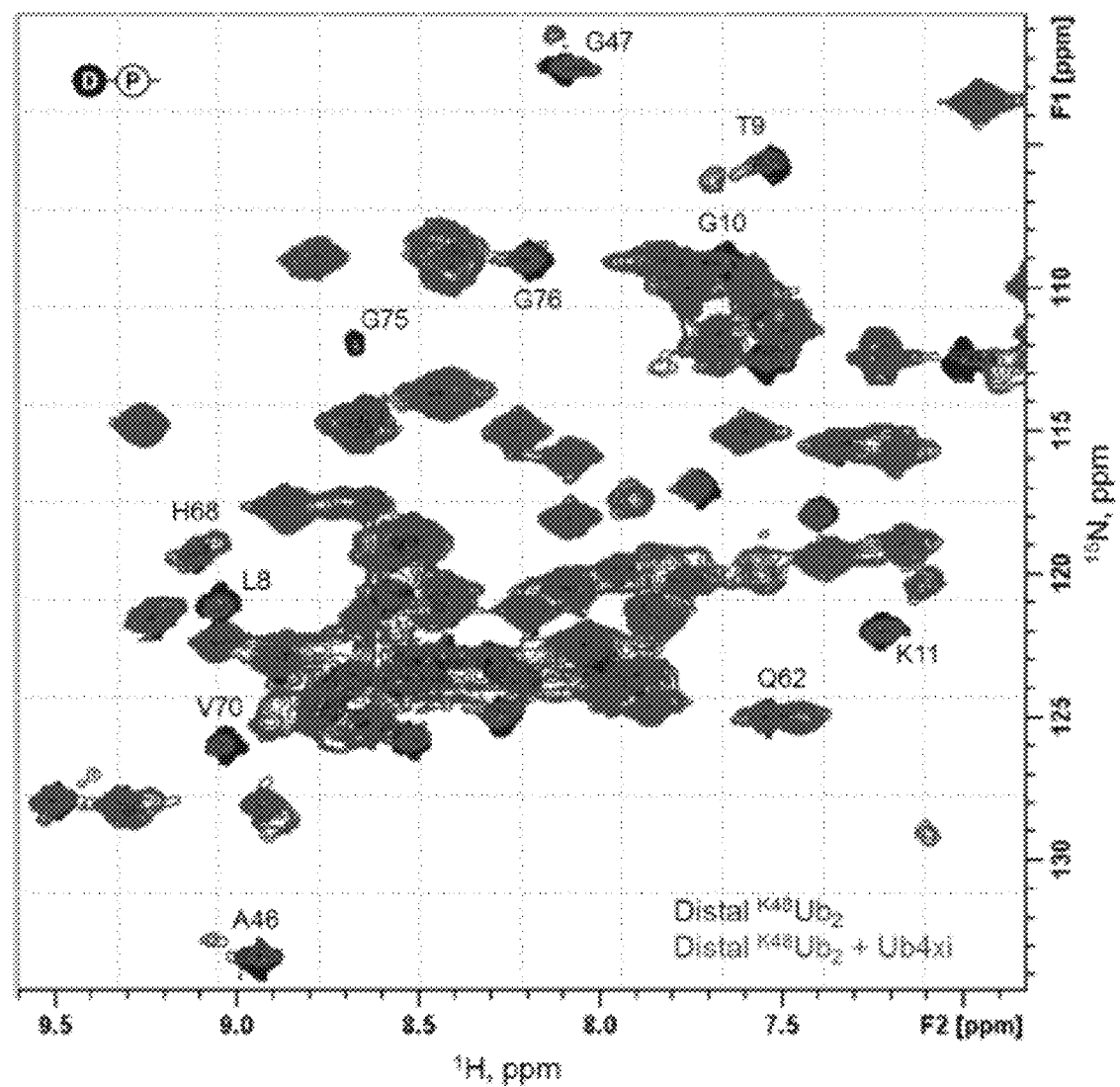
FIG. 27 is a graph showing residue-specific perturbations in the distal Ub of $^{K48}$Ub$_2$ upon Ub4xi binding. Shown is an overlay graph of the $^1$H-$^{15}$N correlation spectra of $^{K48}$Ub$_2$ (distal) free (blue) and in the presence of 1 molar equivalent (red) of Ub4xi. Select perturbed residues are indicated. The average amide $^1$H T$_2$ decreased from ~25 ms to ~21 ms, indicative of an increase in the overall size of Ube upon peptide binding.
Figure 28:
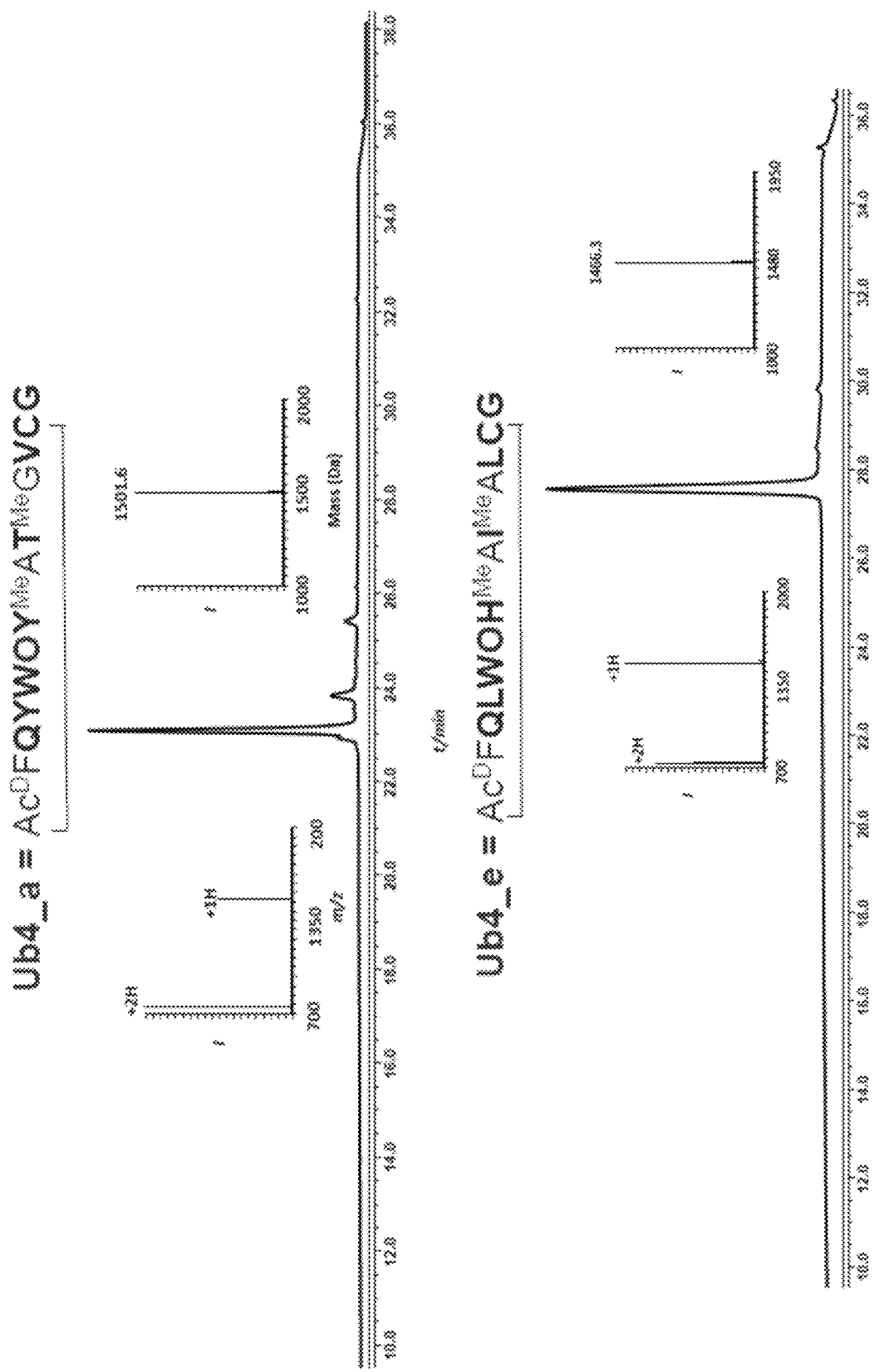
FIGS. 28A-28B are graphs of chromatograms of analytical HPLC and ESI-MS analyses of chemically synthesized cyclic peptides. The purified cyclic peptides Ub$_4$_a (28A) and Ub$_4$_e (28B) were observed with masses of 1,501.6 Da and 1,466.3 Da, respectively.

The $^1H$ T2 reduced from 50 ms to ~33 ms, was consistent with the formation of Ub/Ub2ii complexes. This T2 value is somewhat smaller than expected for an Ub/peptide complex (~40 ms) but greater than for Ube (25 ms) and suggests that a fraction of the complexes might contain two Ubs bound to the same peptide. Using NMR, the inventors also monitored the interaction between Ub4ix and $^{K48}Ub_4$, focusing on the distal and neighboring endo Ub units (units 4 and 3, respectively, counting from the proximal end of the chain) (FIGS. 2D, 19 and 21). As for $^{K48}Ub_2$, the inventors observed a clear slow-exchange regime of binding, and for both Ub units studied, the binding interface was mapped to the hydrophobic patch on Ub surface (FIG. 2E). Interestingly, the disappearance of the unbound signals of the distal Ub (unit 4) occurred at higher peptide concentrations than for unit 3 or the proximal Ub, suggesting weaker binding to the most distal Ub in the chain. Furthermore, in contrast to Ub unit 3, the unbound signals of the distal Ub did not completely disappear even at 2 molar equivalents of the peptide, suggesting occurrence of a second binding event. This had also corroborated by the continuing decrease in $^1H\ T_2$ from 13 ms (free $Ub_4$) to 10 ms to 8 ms (at 1 and 2 molar equivalents of the peptide, respectively). Moreover, for some residues in the distal Ub the inventors observed more than one alternate signal upon titration, indicative of more than one bound conformation of the peptide. In order to examine if this effect was related to the length of the chain or the external (distal) position of the Ub unit, the inventors performed similar binding studies for $^{K48}Ub_3$ (FIGS. 22-24). The effect of the peptide binding on the NMR spectra of the distal Ub in this tri-Ub was comparable with that in unit 3 of tetra-Ub and different from the most distal Ub in tetra-Ub (FIGS. 2d and 25). Also for the proximal Ub units in $^{K48}Ub_4$ and $^{K48}Ub_3$ exhibited similar patterns of residue-specific perturbations (FIGS. 21, 24 and 26). Together, these results suggested that the cyclic peptide primarily binds to/across the first three Ub units in tetraUb. Consistent with this conclusion and the SPR results, the addition of Ub4ix to $^{K48}Ub_2$ caused less spectral perturbations than in the case of Ub2ii peptide at the same (1:1) molar ratio (FIG. 21), indicating weaker binding.

Example 6

Cyclic Peptide Protects Ub Chains Against DUB Cleavage In Vitro

The inventors further chose to examine the effect of these cyclic peptides on two DUBs: OTUB1, a K48-linkage chain specific DUB, and USP2, which cleaves most Ub chains without specificity, using K48-linked di- and tetra-Ub chains as substrates. Ten (10) µM cyclic peptide, and associated binding to Ub chains substrates, was sufficient to fully

TABLE 1

Fit kinetic and equilibrium parameters for cyclic peptides binding to Ub chains.

Figure 30:
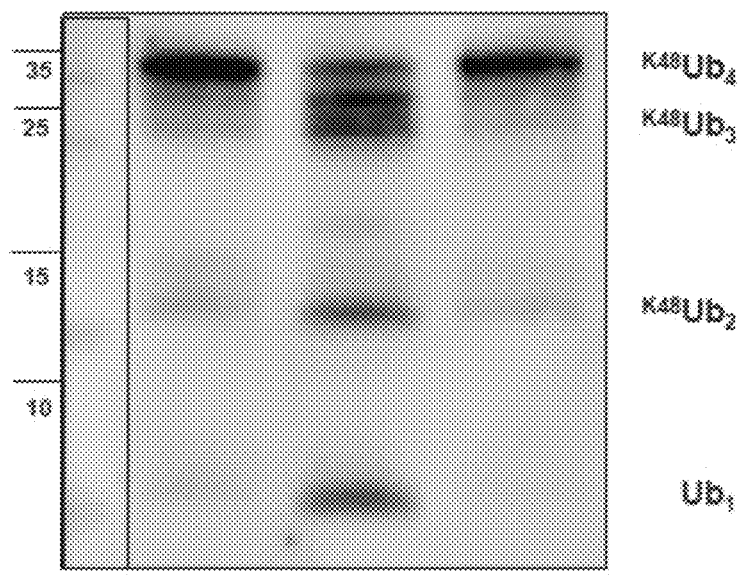
FIG. 30 is an image of western blot analysis of K48-tetra-Ub incubated with active deubiquitinating enzymes (DUBs) and Ub$_4$_a. $^{K48}$Ub$_4$ was incubated with active OTUB1, UBCH5B (E2 enzyme) and the cyclic peptide. The same amounts were loaded on 14% SDS-PAGE, electro-blotted to nitrocellulose membrane and probed with an anti-Ub antibody.
Figure 33:
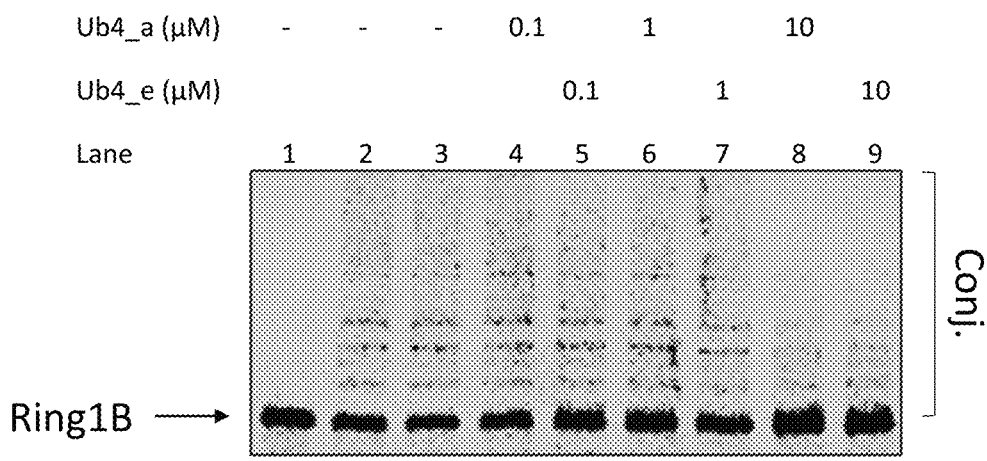
FIG. 33 is an image of a western blot analysis demonstrating inhibition activity of cyclic peptides over Ub elongation. Ub$_4$_a and Ub$_4$_e cyclic peptides were found to inhibit K48-linked Ub elongation (Conj.) on Ring1B in vitro.

| Target | Peptide | $k_{on}$ ($M^{-1}\ s^{-1}$) | $k_{on}$ (error) | $k_{off}$ ($s^{-1}$) | $k_{off}$ (error) | $K_D$ (nM) | $K_D$ (error) |
|---|---|---|---|---|---|---|---|
| $^{K48}Ub_2$ | Ub2i | 5.93E+05 | 1.78E+05 | 0.024 | 0.002 | 40 | 12 |
| $^{K48}Ub_4$ | Ub2i | 7.79E+05 | 1.91E+05 | 0.011 | 0.001 | 14 | 4 |
| $^{K48}Ub_2$ | Ub2ii | 4.89E+05 | 1.09E+05 | 0.016 | 0.001 | 33 | 8 |
| $^{K48}Ub_4$ | Ub2ii | 8.77E+05 | 2.33E+05 | 0.012 | 0.001 | 14 | 4 |
| $^{K48}Ub_2$ | Ub4i | 2.62E+05 | 8.01E+04 | 0.024 | 0.001 | 91 | 28 |
| $^{K48}Ub_4$ | Ub4i | 4.07E+05 | 1.10E+05 | 0.011 | 0.001 | 26 | 7 |
| $^{K48}Ub_2$ | Ub4ix | | | | | >1100 | |
| $^{K48}Ub_4$ | Ub4ix | 3.52E+06 | 7.30E+05 | 0.021 | 0.002 | 6 | 1 | inhibit any cleavage by OTUB1 (FIGS. 3A-B and 30). This suggested that the binding of these cyclic peptides interferes with the recognition of diUb by OTUB1. However, with USP2 using di-Ub as the substrate, the inventors observed (~40%) inhibition in the presence of Ub2i, Ub2ii or Ub4i, and only minimal inhibition by Ub4ix (FIGS. 3C and D), perhaps due to its weaker binding to diUb. Interestingly, the inventors observed strong inhibition and further disassembly of the chain when the distal Ub was removed in a tetra-Ub chain thus shortening the chain to a tri-Ub, in particular for Ub4i and Ub4ix. For Ub4ix this can be explained by the NMR results that suggested that the cyclic peptide only weakly interacted with the distal Ub, which may be sterically accessible for cleavage by USP2. Interestingly, the same cyclic peptides did not protect $^{K63}Ub_2$ chains from USP2 cleavage as well as the structurally similar $^{K11}Ub_2$ from Cezanne cleavage, highlighting the specificity of the cyclic peptides towards the K48 linkage.

Example 7

Cyclic Peptide Prevents Ubiquitinated Proteins from Proteasomal Degradation

The inventors wanted to examine whether the binding of cyclic peptides to K48-Ub chains could prevent the recognition by the proteasome and inhibit the degradation of proteins tagged with these Ub chains. To test this, the inventors incubated a α-globin-K48-linked tetra-Ub and 26S proteasome, with or without Ub4ix, Ub4_a and Ub4_e. While the untreated sample showed proteasomal degradation, Ub4ix, Ub4_a and Ub4_e at 5.3 µM exhibited clear inhibition, comparable to effect of a direct proteasome inhibitor, MG132 (FIGS. 4 and 32). Uncyclized/linear Ub4ix showed no inhibition, highlighting the requirement of the cyclic topology for binding to Ub (FIG. 4B).

Example 8

Ub4ix Enters into HeLa Cells

Figure 5A:
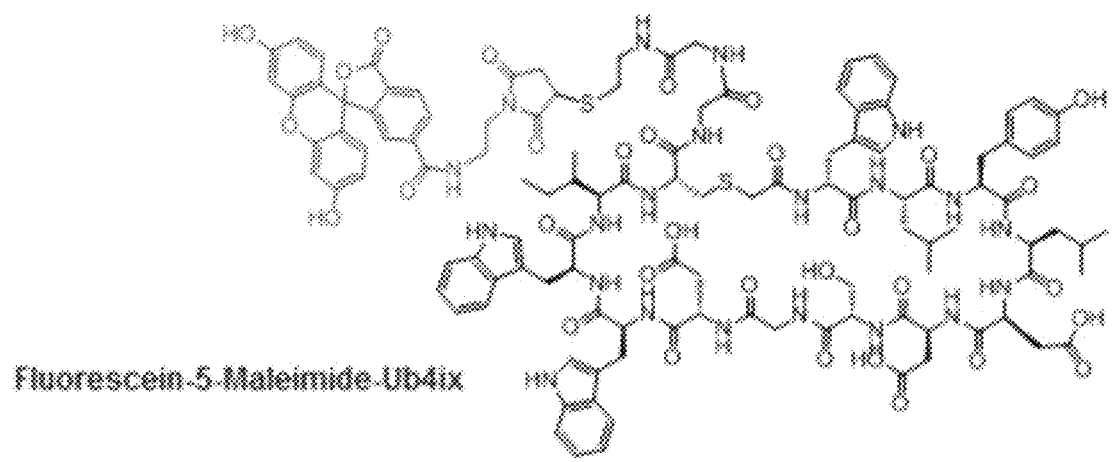
FIGS. 5A-5F are images and graphs showing the uptake of Ub4ix by living cells and its cellular effect. (5A) is an image of the structure of fluorescein-5-maleimide-Ub4ix. (5B) is micrographs of HeLa cells incubated in the presence of DMSO (Negative control) or fluorescein-5-maleimide-Ub4ix cyclic peptide (20 μM). Internalization of the peptide into the cells was monitored at the indicated time points. Ub4ix induced the accumulation of Ub-conjugates, as a result of proteolysis inhibition. (5C) is an image of a western blot analysis of ubiquitinated proteins from HeLa cells which were incubated in the presence of Ub4ix, fluorescein-5-maleimide-Ub4ix, or MG132 for the indicated time-periods. Cells were lysed, resolved using SDS-PAGE, proteins were transferred to a nitrocellulose membrane, and the membrane was blotted using an antibody against Ub-conjugates (Ub conj), and Actin. (5D) is a graph of radio-labeled proteins from HeLa cells which were labeled with radioactive S-Met and S-Cys and were then chased for 4 hours in "cold" media. Cells were either non-treated (Control), or incubated in the presence of DMSO, Ub4ix, or MG132, at the indicated concentrations. Radioactivity levels, resulting from protein breakdown during the chase phase, were measured using a scintillation counter. (5E) is a graph of protein breakdown, relative to non-treated cells (Control), based on the conditions and measurements in (5D). (5F) is an image of western blot analysis of p53 and p27 from HeLa cells which were incubated in the presence of Ub4ix or MG132 for the indicated times. Cells were lysed, resolved using SDS-PAGE, proteins were transferred to a nitrocellulose membrane, and the membrane was blotted using an antibody against p53, p27, or Actin.
Figure 5B:
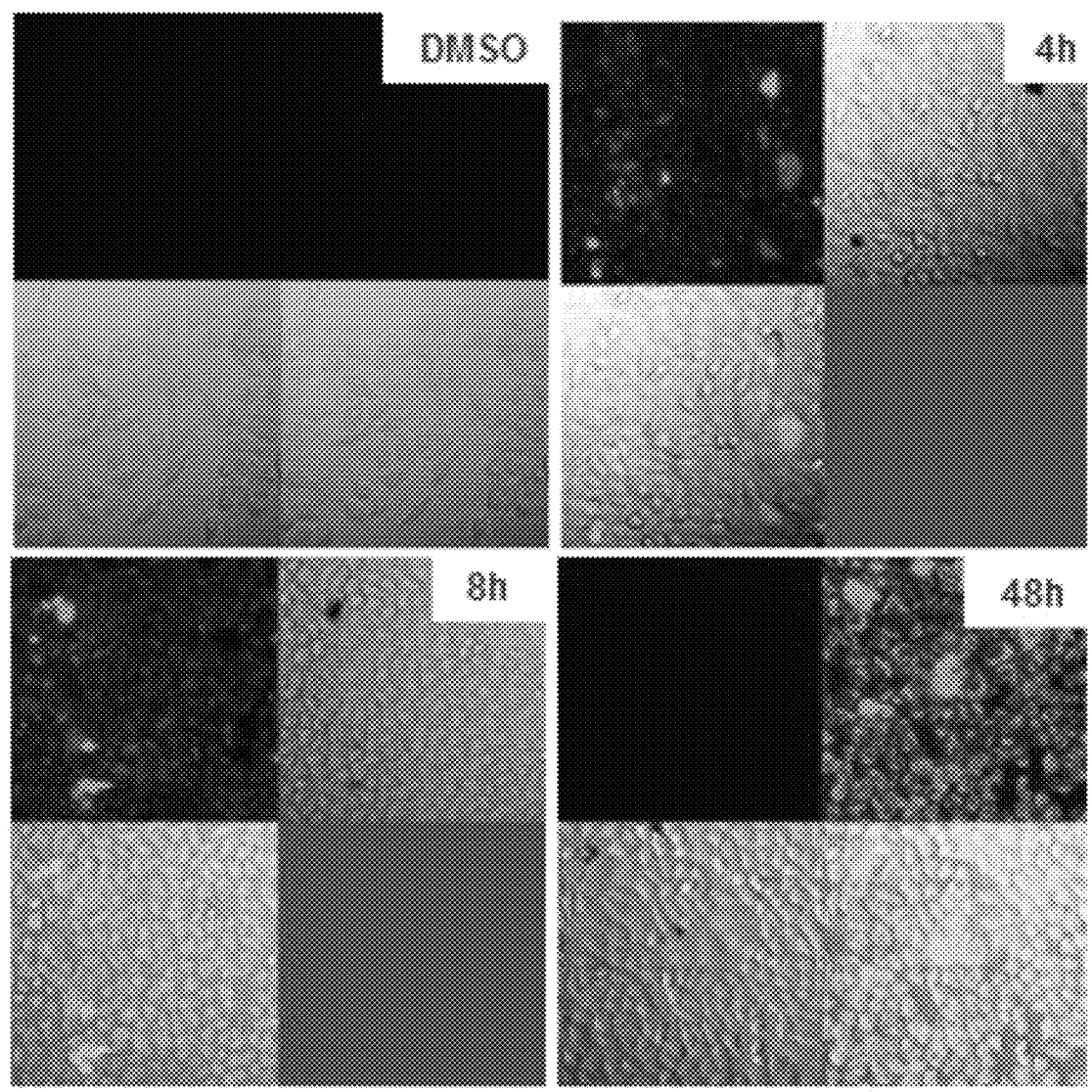
Figure 5E:
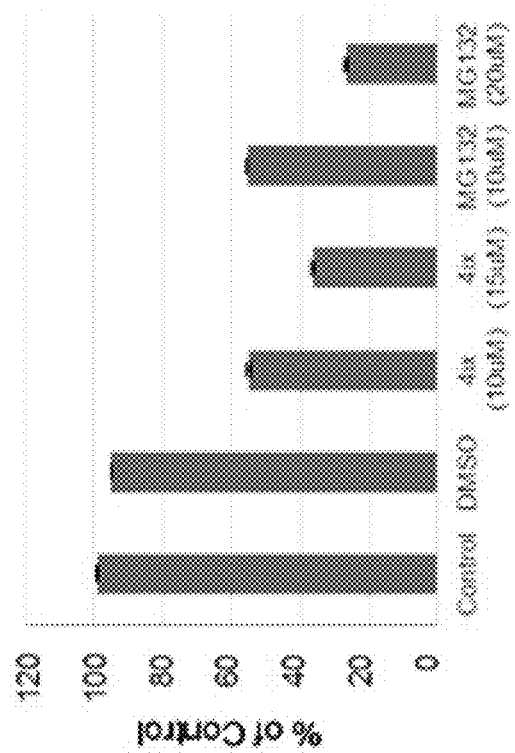

In order to assess the feasibility of using Ub4ix in cultured cells, the inventors next tested whether Ub4ix is able to cross the cellular membrane of human cells. The inventors synthesized Ub4ix labeled with fluorescein and used live cell imaging to monitor its entrance into HeLa cells, USOS osteosarcoma cells, and U87 primary glioblastoma cells. The uptake of labeled Ub4ix was evident as early as 4 hours in HeLa cells (FIG. 5B). Following its addition to the culture medium, with further intracellular marked accumulation, throughout the following 48 hours (FIG. 5B). Ub4ix was quickly and efficiently distributed within cells allowing for testing in more representative biological models without further modification or special delivery systems. Comparing the uptake of fluorescein-Ub4ix with fluorescein alone in U2OS osteosarcoma cells and U87 primary glioblastoma cells, fluorescein-Ub4ix exhibited considerable cell permeability (FIG. 38). All in all, a cyclic peptide of the invention, for example Ub4ix, was shown to effectively penetrate cancerous cells of diverse origins, e.g., epithelium, bone, and neural.

Example 9

Ub4ix Activity Causes Accumulation of Ub-Conjugates

Figure 5F:
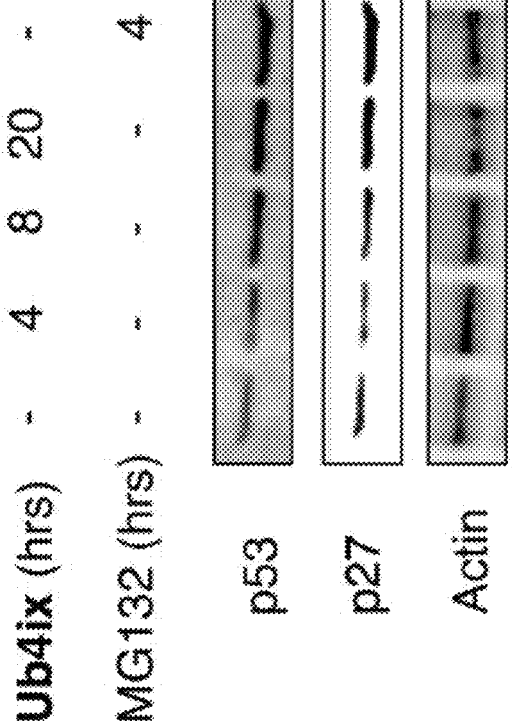
Figure 5C:
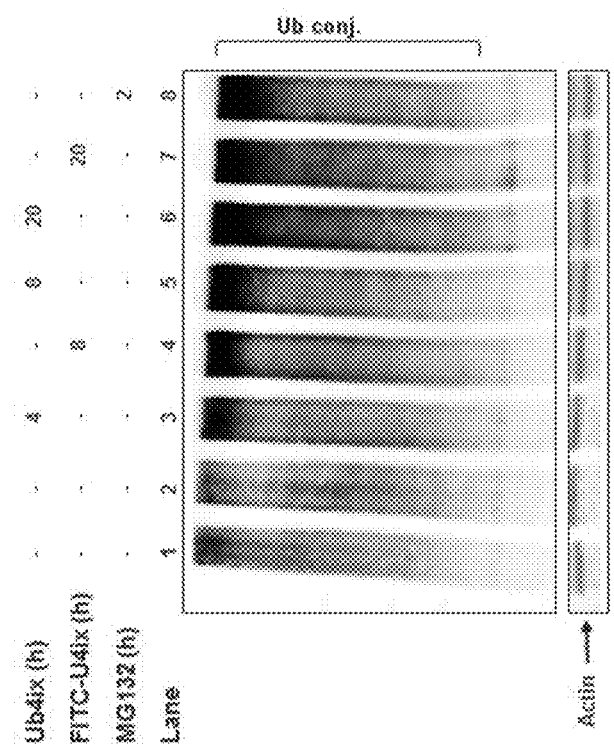

Under basal conditions, the levels of Ub-conjugates reflect a dynamic steady state between the enzymatic bindings of Ub to proteins on the one hand, with the removal of conjugated Ub moieties by DUBs, and subsequent degradation by the proteasome, on the other. The inventors had shown in vitro that the cyclic peptide Ub4ix protected Ub-chains from cleavage by DUBs, and also prevented recognition by the proteasome. Both effects were predicted to prevent degradation, and lead to the accumulation of proteins tagged with K48-Ub chains in cells. The inventors monitored the cellular level of Ub-conjugates in cells upon treatment with Ub4ix, and were able to demonstrate such elevation in Ub-conjugates following treatment with the cyclic peptide Ub4ix, both in its free or the labeled forms (FIG. 5C). Such an effect was similar to the one observed when treating cells with the direct proteasome inhibitor MG132 (FIG. 5C).

The slower accumulation of Ub-conjugates in the presence of Ub4ix, compared to MG132, may be attributed to the different targets of the two agents. While MG132 targets the proteasome directly, Ub4ix binds the Ub-chains, and therefore its inhibitory effect on the proteasome is being built gradually. Interestingly, though slower kinetics with regard to proteasome inhibition, the effect of Ub4ix eventually seemed to supersede that of MG132 (FIG. 5C). Such result may represent an inhibitory effect of Ub4ix on the degradation of proteins also by autophagy, which in some cases relies on ubiquitination as well.

Figure 5D:
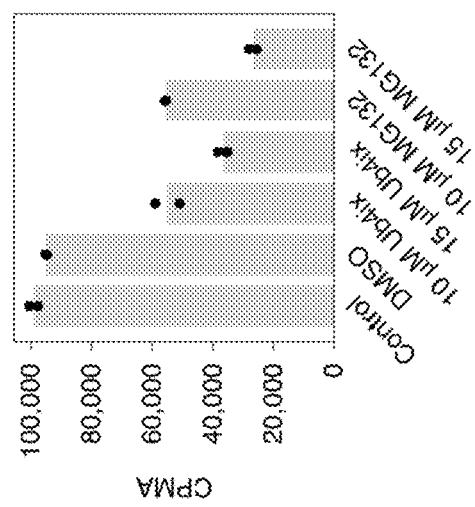

In order to directly measure the effect of Ub4ix on proteolysis, the inventors employed radiolabeling of cellular proteins, followed by a chase experiment in the presence of either Ub4ix or the proteasome inhibitor MG132. When compared to non-treated cells, or ones treated with DMSO, protein breakdown in cells treated with Ub4ix was markedly reduced, with similar rates of degradation observed in the presence of MG132 (FIGS. 5D and E). Both agents showed a dose-dependent effect on cellular protein degradation. The inventors validated this inhibitory effect on protein breakdown with known proteasomal substrates, the proteins p53, and p27, bona fide substrates of the UPS. In the presence of the Ub4ix, both p53 and p27 were accumulated over time, up to similar levels to the ones observed by MG132 (FIG. 5F).

Example 10

Cyclic Peptides Induce Apoptosis

Figure 6A:
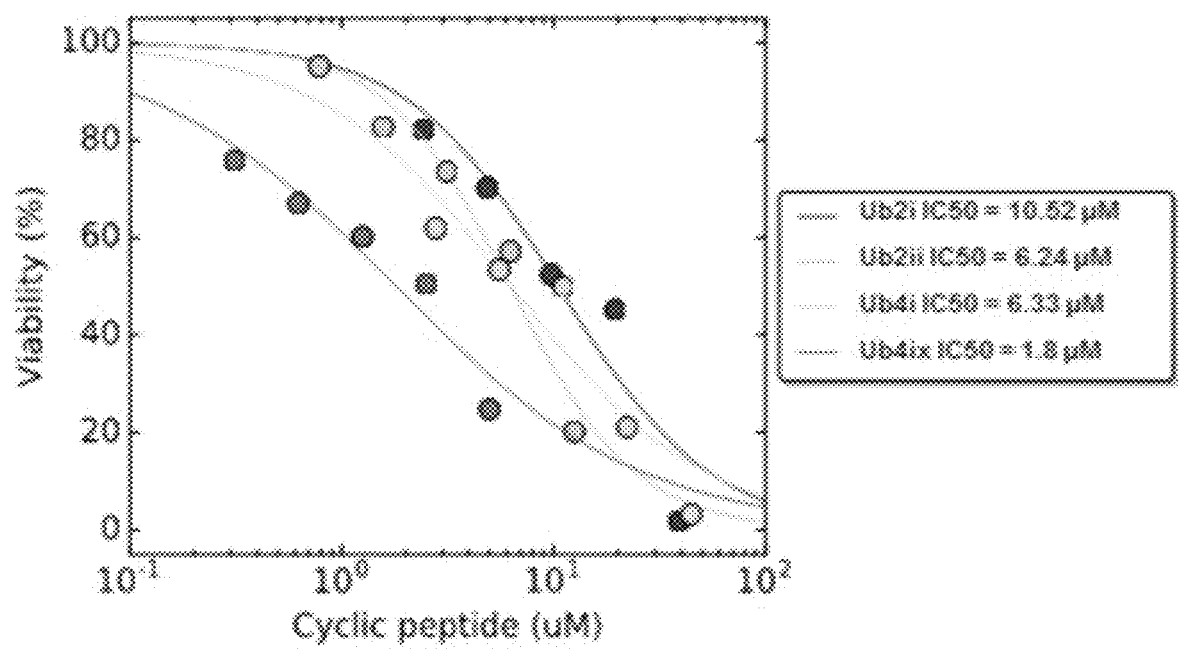
FIGS. 6A-6B are graphs demonstrating the effect of Ub4ix on HeLa cells. (6A) is a graph of the effect of cyclic peptides on HeLa cells viability, as measured by MTT. Ub4ix inhibits cell viability of Hela cells with an IC$_{50}$ of 1.8 μM after 48 h incubation, while the rest of the peptides incubate for 72 h. (6B) is a vertical bar graph of the effect of Ub4ix on HeLa cells apoptosis. Cells were exposed to the indicated Ub4ix cyclic peptide for 24 and 48 h, after which FACS was used to measure % apoptosis. L-Ub4ix—linear Ub4ix; C-Ub4ix—cyclic Ub4ix.
Figure 6B:
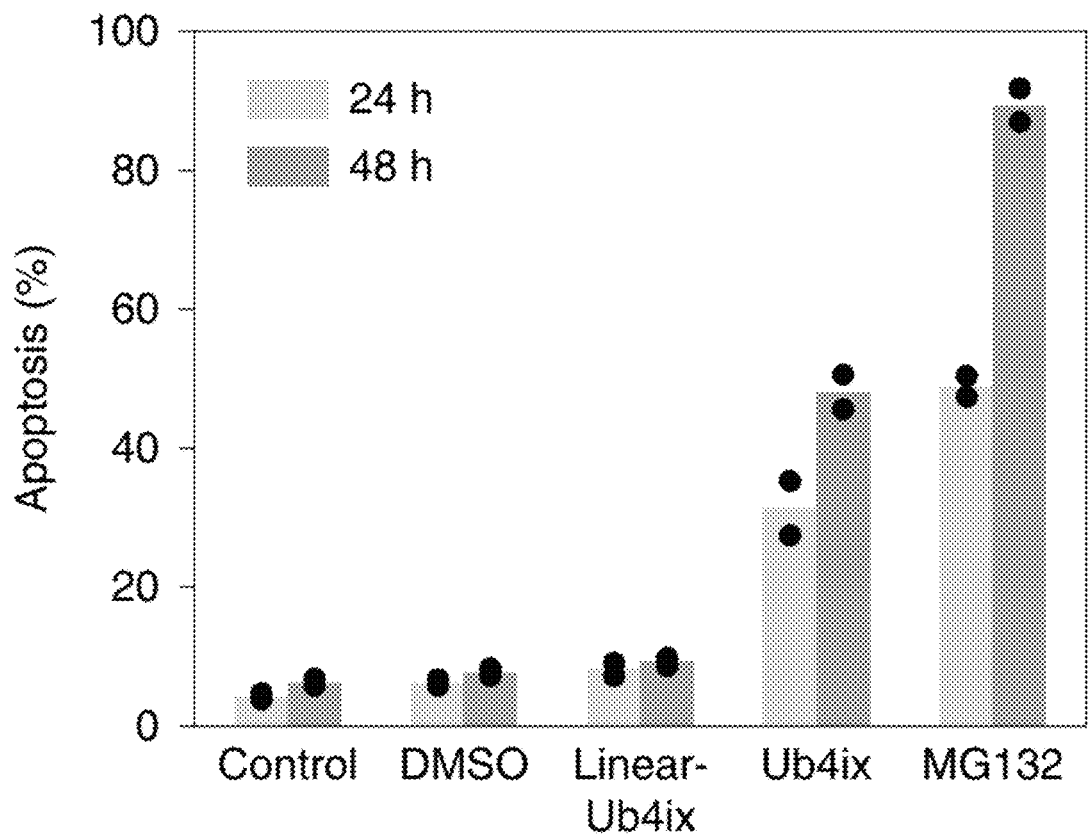

Given that Ub4ix has a pronounced inhibitory effect on the UPS system, the inventors further wanted to examine whether it inhibit cell growth and induce apoptosis in cancer cells. To test this, HeLa cells were treated with each cyclic peptide and cell growth was found to be dramatically suppressed when viability was assessed using an MTT assay. The inventors noted that Ub4ix was the most effective in suppressing growth (FIG. 6A). The effects of the cyclic peptides on apoptosis were evaluated using FACS analysis. Intriguingly, Ub4ix at 10 µM exhibited clear increase in apoptosis after 24 h and 48 h treatment, similar to the direct proteasome inhibitor MG132 (FIG. 6B).

Example 11

Two-Fold Strategy Yields Affinity Improved Cyclic Polypeptides

Figures 34A, 34B:
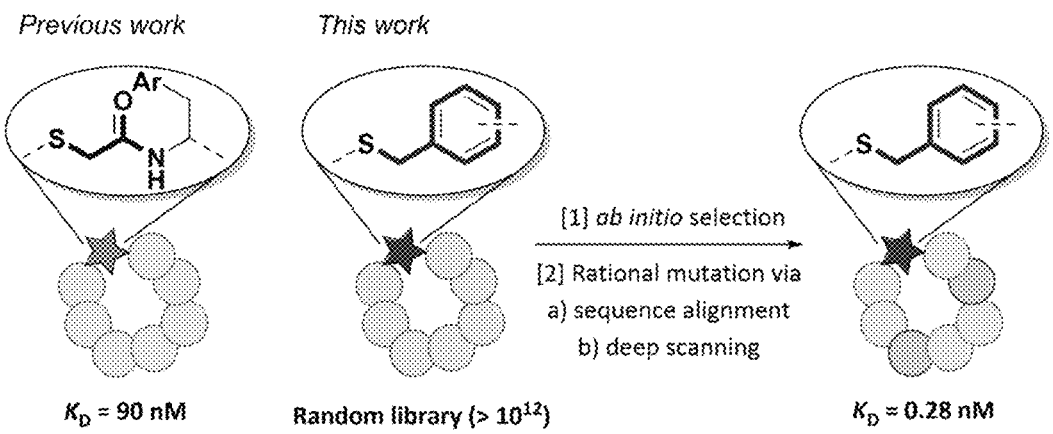
FIGS. 34A-34B are illustrations of a non-limiting strategy proposed to achieve affinity enhancement of an initial hit peptide from primary selection. (34A) macrocyclic peptide cyclized by the halide anchor, chloroacetyl D-Trp showed 90 nM binding affinity. (34B) A two-step strategy is proposed to achieve affinity enhancement. The strongest binder showed 0.28 nM binding affinity.
Figure 35A:
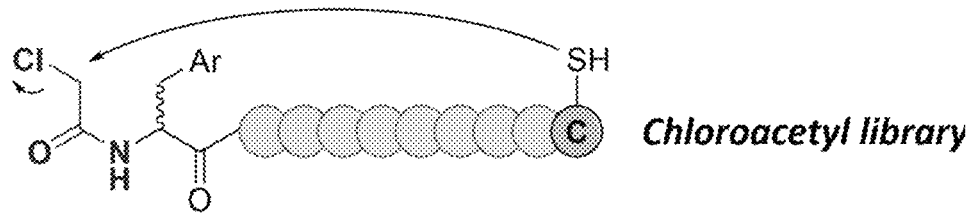
FIGS. 35A-35D are illustrations of a non-limiting scheme of library design for the RaPID selection of macrocyclic peptides. (35A) is an exemplary illustration of a Chloroacetyl library member. (35B) is an exemplary illustration of a Chlorobenzyl library member. (35C) is non-limiting examples of molecular structures of Chlorobenzyl type initiators applicable according to the disclosed invention. (35D) is an illustration of a non-limiting scheme of the RaPID selection platform which consists of seven steps in one round.
Figure 35B:
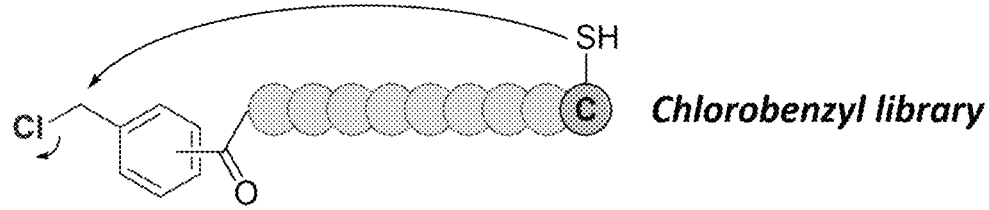
Figure 35C:
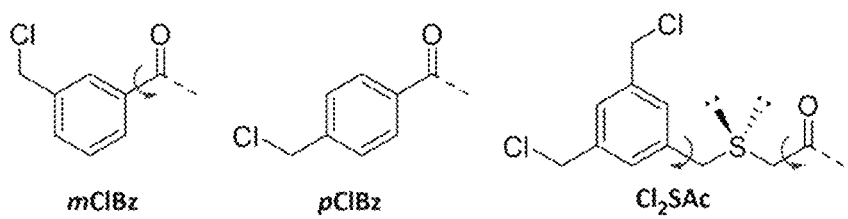
Figure 35D:
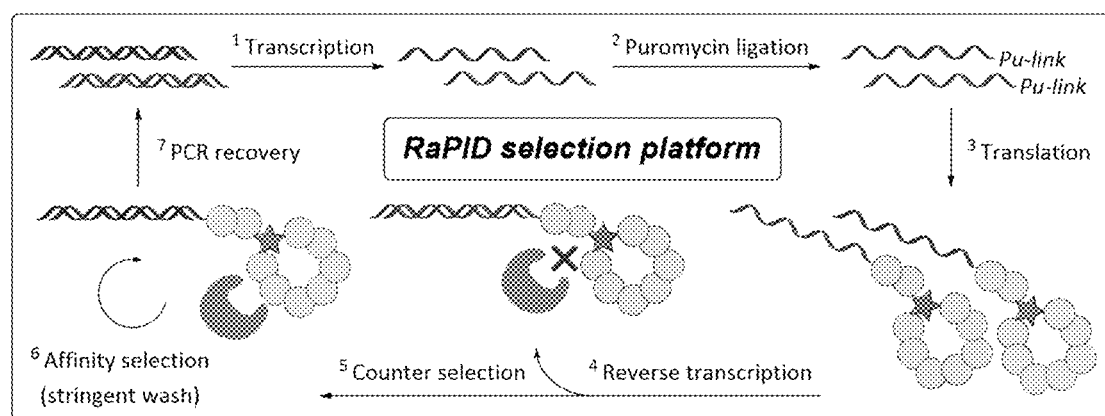

The inventors described a practical twofold strategy that combines 1) ab initio selections based on peptide libraries containing new thioether anchors, and 2) ration mutations based on sequence alignment and deep scanning, to improve peptide's binding affinities (FIG. 34B). Step 1 was carried out by in-parallel running a standard RaPID selection but using new peptide libraries with a change of the thioether anchor at N-terminus. Using Lys48-linked ubiquitin dimer or K48-Ub$_2$ as a model protein for this strategy, the inventors successfully obtained a primary hit peptide (cyclized through chlorobenzyl group) that showed 9-fold improvement over a previous peptide containing the same sequence yet different initiator (cyclized through chloroacetyl group), with K$_D$ reduced from 90 nM to 10 nM. Then step 2 was performed to introduce several key amino acid mutations. In the case of K48-Ub$_2$, by combining the twofold strategy, the inventors successfully achieved 320-fold increase (K$_D$ from 90 nM to 0.28 nM) in binding affinity.

Using MiSeq sequencing, the inventors isolated top 10 candidate sequences with a different combination of initiators, of which 6 unique peptides from mClBz and pClBz libraries were picked up for surface plasmon resonance (SPR) binding assays. Next, the inventors settled to check the in vitro binding affinity of the six candidate peptides obtained from primary selection by using SPR. Surprisingly, all of them showed high sequence similarity, but striking difference of binding affinity from what reported previously. As shown in Table 2, sequences of J01, J02 and J08 were found to be highly similar to U2ii, U2i and U4i. Regarding affinity, J01 mClBz/pClBz from chlorobenzyl library had higher KD than their analogue U2ii from chloroacetyl library, while J02_mClBz had improved affinity compared with their analogue U2i. Furthermore, J08_mClBz was found to have much greater avidity than U4i, a ClAc-DTrp-initiated analogue of J08. The inventors concluded that peptides selected out from different libraries may share highly conservative motifs as in this case against K48-Ub2. However, binding affinities of these peptides may span a wide range with up to 10-fold difference (J02_pClBz vs U2i and J08_mClBz vs U4i). Therefore, even delicate change in the initiator structure may cause a substantial change of the macrocycle conformation, which can further affect the affinity.

TABLE 2

Affinity enhancement through (Step 1) ab initio selection using chlorobenzyl library and (Step 2a) rational design of peptide mutants based on sequence alignment of three macrocycle sequence family members J01, J02 and J08.

| Names | | Sequence | M* | K$_D$ (nM) |
|---|---|---|---|---|
| Selection using chloro-acetyl library | U2i | M*GWFDNLYWYVTH-CG | ClAc-$^D$Trp | 40 |
| | U2ii | M*-WYDREYYYLGYGCG | ClAc-$^D$Trp | 33 |
| | U4i | M*GWFDDLYLFVAY-CG | ClAc-$^D$Trp | 90 |
| Step 1 Selection using chloro-benzyl library | J01 | M*-WYDREYYYLGYGCG | mClBz/pClBz | 141/141 |
| | J02 | M*GWFDNLYWYITH-CG | mClBz/pClBz | 16/48 |
| | J08 | M*GWFDDLYLFVAY-CG | mClBz/pClBz | 10/234 |
| Step 2a Mutation based on sequence alignment from J08 | L6E | M*GWFDDEYLFVAY-CG | mClBz | 5.0 |
| | L8W | M*GWFDDLYWFVAY-CG | mClBz | 1.2 |
| | V10Y | M*GWFDDLYLFYAY-CG | mClBz | 5.6 |
| | Above all | M*GWFDDEYWFYAY-CG | mClBz | 7.2 |

Starting from J08_mClBz, which already showed 9-fold improvement compared with U4i (K$_D$=90 nM→10 nM), the inventors moved to step 2 to carry out post-selection affinity enhancement. By looking deeper into the motifs from J01, J02 and J08, which all stood out from NNK12 library, the inventors were able to determine a 'WFDXXY' core motif that was conserved among almost all candidate sequences (Table 2). The inventors then examined whether exchanging single residues of J08 for their counterparts from J01 and J02, would boost the affinity of J08_mClBz. Surprisingly, this turned out to be the case. All three mutations showed favorable binding improvement especially two mutations L6E and L8W (FIG. 36), which produced J08_mClBz_L6E and J08_mClBz_L8W with 5.0 nM and 1.2 nM binding affinity respectively.

Figure 36:
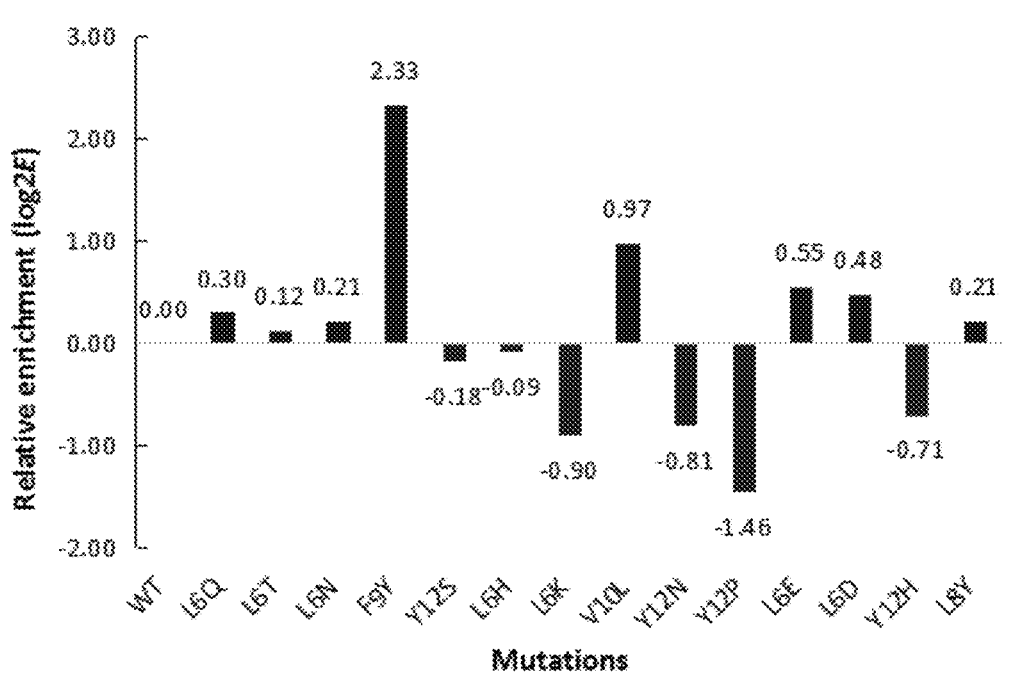
FIG. 36 is a bar graph showing relative enrichment (log$_2$ E) versus single mutations based on deep scanning (Step 2b in FIG. 34B). E=Positive fraction %/Input fraction % according MiSeq sequencing results. Bars of positive values and negative values indicate potentially favorable and unfavorable mutations, respectively.
Figure 37A:
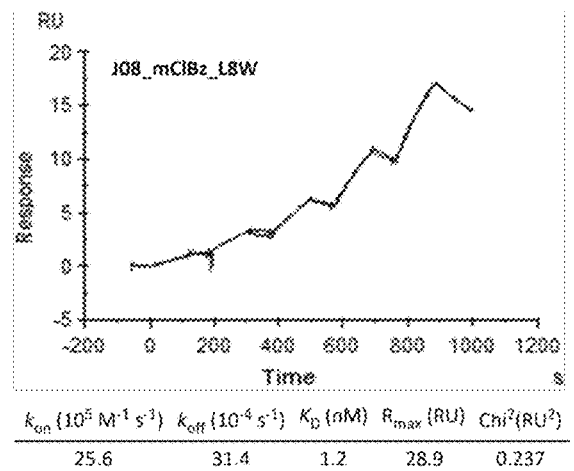
Figure 37B:
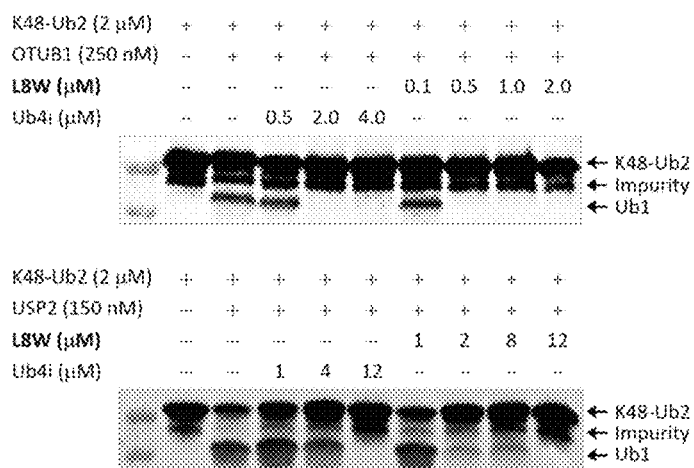
Figure 37C:
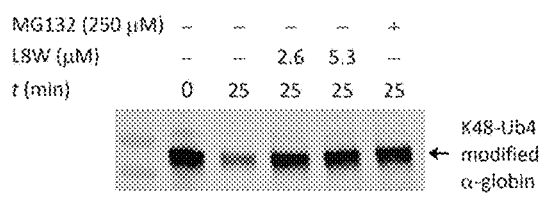
Figure 37D:
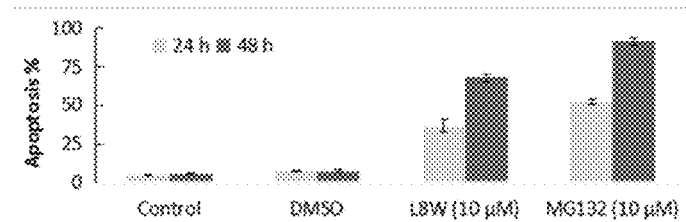

Thereafter, the inventors tested whether specifically induced single mutations would further increase affinity of the isolated polypeptide (i.e., J08). Deep mutational scanning results displayed several positive mutations as evidenced by higher enrichment of certain mutant peptides than the wildtype J08_mClBz (FIG. 36). Mutation of Leu6 seemed highly flexible which allowed its replacement by either nonpolar or polar residues. Meanwhile, F9Y showed a highly likely positive mutation according to a considerable relative enrichment ratio >5. Based on this information, the inventors prepared nine peptides containing F9Y mutations. As expected, J08_mClBz F9Y was confirmed to be a stronger binder (K$_D$=0.58 nM, 17-fold improvement from J08_mClBz), while double mutations or triple mutations provided similar affinity (for J08_mClBz_L8W_F9Y, K$_D$=0.69 nM; for J08_mClBz_L6E_L8W_F9Y, K$_D$=0.28 nM). Noteworthy is the fact that the best binder J08_mClBz_L6E_L8W_F9Y showed close k$_{on}$, k$_{off}$ and K$_D$ parameters to a K48-Ub2 specific antibody, yet has much lower molecular weight, which further demonstrates the great potential of using macrocyclic peptides to target protein targets.

TABLE 3

Summary of SPR-measured affinities of J08 analogue peptides.

| Sequence source | J08 peptide analogues (Anchor_Mutations) | $K_D$ (nM) |
| --- | --- | --- |
| Control ref. | ClAc-$^D$Trp | 90 |
| After Step 1 | mClBz | 10 |
|  | pClBz | 234 |
| After Step 2a | mClBz_L6E | 5.0 |
|  | mClBz_L8W | 1.2 |
|  | mClBz_V10Y | 5.6 |
|  | mClBz_L6E_L8W_V10Y | 7.6 |
| After Step 2b (with control) | mClBz_F9Y | 0.58 |
|  | mClBz_L8W_F9Y | 0.69 |
|  | pClBz_L8W_F9Y | 27 (~40x weaker) |
|  | Bz_L8W_F9Y | 2200 (~3200x weaker) |
| After Step 2a/b | mClBz_L6E_L8W_F9Y | 0.28 |
|  | mClBz_L6Q_L8W_F9Y | 0.37 |
|  | mClBz_L6N_L8W_F9Y | 0.48 |
|  | mClBz_L6H_L8W_F9Y | 0.37 |
|  | mClBz_L6K_L8W_F9Y | 0.35 |
| Control ref. | Anti-K48-Ub2 antibody | 0.28 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A cyclic polypeptide comprising the amino acid sequence FQX$_1$WOX$_2$AX$_3$X$_4$X$_5$CG (SEQ ID NO: 5), wherein X$_1$ is an amino acid selected from: Tyr or Leu, X$_2$ is an amino acid selected from: Tyr or His, X$_3$ is an amino acid selected from: Thr or Ile, X$_4$ is an amino acid selected from: Gly or Ala, and X$_5$ is an amino acid selected from: Val or Leu.

2. The cyclic polypeptide of claim 1, comprising an amino acid sequence selected from the group consisting of: FQYWOYATGVCG (SEQ ID NO: 35); and FQLWOHAIALCG (SEQ ID NO: 36).

3. The cyclic polypeptide of claim 2, wherein the amino acid residues at position 6, 8 or both, of SEQ ID Nos.: 35-36 are methylated.

4. The cyclic polypeptide of claim 1, wherein: (i) said polypeptide comprises not more than 16 amino acid residues; (ii) the amino acid at position one is a D amino acid; or a combination thereof.

5. The cyclic polypeptide of claim 1, wherein the amino acid at position one is conjugated to a cyclizing molecule, and optionally wherein said cyclizing molecule is selected from the group consisting of: chloracetyl chloride, 3-chlorobenzoyl (3-ClBz), 4-chlorobenzoyl (4-ClBz) or Cl$_2$SAc, or wherein said cyclic polypeptide is prepared using a cyclizing molecule comprising a halogen.

6. The cyclic polypeptide of claim 1, wherein said cyclic polypeptide is characterized as having: cell penetration capability, ubiquitin (Ub) binding capability, increased affinity to Ub compared to control, or a combination thereof, and optionally wherein said increased affinity is binding affinity K$_D$ of 0.05-100 nM.

7. A composition comprising the cyclic polypeptide of claim 1 and at least one acceptable carrier or diluent.

8. A method for ameliorating or treating cancer in a subject in need thereof, the method comprising administering to the subject a therapeutically effective amount of the cyclic polypeptide of claim 1.

9. The method of claim 8, wherein said cyclic polypeptide reduces cell viability with an IC$_{50}$ of 0.05-15 μM.

* * * * *